(12) United States Patent
Shirakawa

(10) Patent No.: US 11,685,788 B2
(45) Date of Patent: *Jun. 27, 2023

(54) ANTI-PRESEPSIN ANTIBODY

(71) Applicant: Mochida Pharmaceutical Co., Ltd., Tokyo (JP)

(72) Inventor: Kamon Shirakawa, Tokyo (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 344 days.

This patent is subject to a terminal disclaimer.

(21) Appl. No.: 16/864,673

(22) Filed: May 1, 2020

(65) Prior Publication Data

US 2021/0107990 A1 Apr. 15, 2021

Related U.S. Application Data

(62) Division of application No. 15/915,658, filed on Mar. 8, 2018, now Pat. No. 10,676,532, which is a division of application No. 14/631,668, filed on Feb. 25, 2015, now Pat. No. 9,951,142.

(60) Provisional application No. 61/944,674, filed on Feb. 26, 2014.

(51) Int. Cl.
*A61K 39/00* (2006.01)
*C07K 16/28* (2006.01)
*G01N 33/68* (2006.01)
*G01N 33/569* (2006.01)

(52) U.S. Cl.
CPC ..... *C07K 16/2896* (2013.01); *G01N 33/6893* (2013.01); *A61K 2039/505* (2013.01); *C07K 2317/14* (2013.01); *C07K 2317/33* (2013.01); *C07K 2317/34* (2013.01); *C07K 2317/565* (2013.01); *C07K 2317/76* (2013.01); *C07K 2317/92* (2013.01); *G01N 33/569* (2013.01); *G01N 2333/70596* (2013.01); *G01N 2800/26* (2013.01)

(58) Field of Classification Search
CPC .............................................. A61K 2039/505
See application file for complete search history.

(56) References Cited

U.S. PATENT DOCUMENTS

| | | | |
|---|---|---|---|
| 7,465,547 B2 | 12/2008 | Furusako et al. | |
| 7,608,684 B2 | 10/2009 | Furusako et al. | |
| 7,901,900 B2 | 3/2011 | Furusako et al. | |
| 8,124,722 B2 | 2/2012 | Furusako et al. | |
| 2006/0068445 A1 | 3/2006 | Furusako et al. | |
| 2007/0106067 A1 | 5/2007 | Furusako | |
| 2009/0029396 A1 | 1/2009 | Furusako et al. | |
| 2009/0203052 A1 | 8/2009 | Furusako et al. | |
| 2011/0086381 A1 | 4/2011 | Naito | |
| 2012/0309025 A1 | 12/2012 | Okamura et al. | |
| 2013/0337476 A1 | 12/2013 | Lee et al. | |
| 2018/0237537 A1 | 8/2018 | Shirakawa et al. | |

FOREIGN PATENT DOCUMENTS

| | | | | |
|---|---|---|---|---|
| JP | 2005-106694 A | 4/2005 | | |
| KR | 102360851 B1 * | 1/2017 | | |
| WO | WO 2004/044005 A1 | 5/2004 | | |
| WO | WO-2004044005 A1 * | 5/2004 | ....... | C07K 14/70596 |
| WO | WO 2005/108429 A1 | 11/2005 | | |
| WO | WO 2009/142303 A1 | 11/2009 | | |
| WO | WO 2011/093459 A1 | 8/2011 | | |
| WO | WO-2015/129774 A1 | 9/2015 | | |

OTHER PUBLICATIONS

Zou et al., "Presepsin as a novel sepsis biomarker," World J. Emerg. Med., 2014, 5(1):16-19.
Korean Office Action dated Jul. 19, 2021 in Korean Application No. 10-2016-7022978 with English machine translation.
Office Action dated Jun. 21, 2021 in Canadian Application No. 2,996,395.
Caldas et al., Mol. Immunol., May 2003, 39(15) :941-952.
Casset et al., "A peptide mimetic of an anti-CD4 monoclonal antibody by rational design," Biochemical and Biophysical Research Communications, 2003, 307:198-205.
Chien, N. C., et al., Proc. Natl. Acad. Sci. USA, 1989, vol. 84, No. 14, pp. 5532-5536.
De Pascalis et al., "Grafting of 'abbreviated' complementary-determining regions containing specificity-determining residues essentially for ligand contact to engineer a less immunogenic humanized monoclonal antibody," Journal of Immunology, 2002, 169:3076-3084.
Giusti et al., "Somatic diversification of S107 from an antiphosphocholine to an anti-DNA autoantibody is due to a single base change in its heavy chain variable region," Proceedings of the National Academy of Sciences, May 1987, vol. 84, pp. 2926-2930.
Gussow et al., "Humanization of Monoclonal Antibodies," Methods in Enzymology, 1991, 203:99-121.
Hayashi et al., "Increased Levels of Soluble CD14 in Sera of Periodontitis Patients," Infection and Immunity, Jan. 1999, 67(1):417-420.
Holm et al., "Functional mapping and single chain construction of the anti-cytokeratin 8 monoclonal antibody TS1," Molecular Immunology, 2007, 44:1075-1084.

(Continued)

*Primary Examiner* — Stephen L Rawlings
(74) *Attorney, Agent, or Firm* — Foley & Lardner LLP

(57) ABSTRACT

The present invention provides methods and compositions for determining sepsis in an individual. Specifically, the present invention provides for antibodies of fragments thereof that specifically bind to presepsin. The antibodies of the present invention may be monoclonal antibodies, and they may specifically bind to a particular epitope of presepsin. The present invention further provides methods of using such antibodies to determine whether an individual has sepsis, and kits comprising the disclosed antibodies.

2 Claims, 6 Drawing Sheets
Specification includes a Sequence Listing.

(56) References Cited

OTHER PUBLICATIONS

Juan et al., "Identification of a Lipopolysaccharide Binding Domain in CD14 between Amino Acids 57 and 64," The Journal of Biological Chemistry, Mar. 10, 1995, 270(10):5219-5224.

Lawn et al., "Elevated serum concentrations of soluble CD14 in HIV− and HIV+ patients with tuberculosis in Africa: prolonged elevation during anti-tuberculosis treatment," Clinical & Experimental Immunology, 2000, 120:483-487.

MacCallum et al., "Antibody-antigen Interactions: Contact Analysis and Binding Site Topography," J. Mol. Biol., 1996, 262:732-745.

Mariuzza et al., "The Structural Basis of Antigen-Antibody Recognition," Ann. Rev. Biophys. Biophys. Chem., 1987, 16:139-159.

Office Action dated Feb. 28, 2019, in corresponding Indonesian Patent Application No. P-00201605634, with English translation.

Okamura et al., "Development of a point-of-care assay system for measurement of presepsin (sCD14-ST)," Clinica Chimica Acta, 2011, vol. 412, pp. 2157-2161.

Popov et al., "SCD14-ST (Presepsin) Level Monitoring in Cardiac Surgical Patients During Perioperative Period," Anesthesiology and Renimatology, 2003, 3:23-35, with English abstract.

Prokhorova, A.M., Ed., The Great Encyclopedic Dictionary, 1993, p. 858, definition of "kit" with English translation.

Rudikoff et al., "Single amino acid substitution altering antigen-binding specificity," Proc. Natl. Acad. Sci. USA, Mar. 1982, 79:1979-1983.

S. Ozhegov, $4^{th}$ Ed., Dictionary of the Russian Language, 2006, p. 375, definition of "kit".

Shirakawa et al., "Presepsin (sCD14-ST): development and evaluation of one-step ELISA with a new standard that is similar to the form of presepsin in septic patients," Clinical Chemistry and Laboratory Medicine, 2011, vol. 49, pp. 937-939.

Vajdos et al., "Comprehensive Functional Maps of the Antigen-binding Site of an Anti-ErbB2 Antibody Obtained with Shotgun Scanning Mutanesis," J. Mol. Biol., Jul. 5, 2002, 320:415-428.

Velkov V.V., "Presepsin is a novel highly effective biomarker of sepsis," Pediatriya, 2013, vol. 92, pp. 128, with English translation.

Winkler et al., "Changing the Antigen Binding Specificity by Single Point Mutations of an Anti-p24 (HIV-1) Antibody," J. Immunol., Oct. 15, 2000, 265:4505-4514.

Wu et al., "Humanization of a murine monoclonal antibody by simultaneous optimization of framework and CFR residues," Journal of Molecular Biology, Nov. 19, 1999, 294:151-162.

Yaegashi et al., "Evaluation of a newly identified soluble CD14 subtype as a marker for sepsis," Journal of Infection and Chemotherapy, 2005, 11:234-238.

Yarilin, A.A., Principles of Immunology: Textbook, Moscow, Medicina, 1999, 172-174, with English translation.

Office Action dated Apr. 13, 2022, in CA 2,996,395.

\* cited by examiner

FIG. 2A

| Variant | VH | | | | | | VL | | | | | | rsCD14ST-Fc | Evaluation |
|---|---|---|---|---|---|---|---|---|---|---|---|---|---|---|
| | CDR1 | | CDR2 | | CDR3 | | CDR1 | | CDR2 | | CDR3 | | KD | |
| 5784 | RYTMG | (SEQ ID NO: 167) | IINSGATYYASWAKG | (SEQ ID NO: 169) | ADF | (SEQ ID No.93) | QASQSIGSNLA | (SEQ ID NO: 172) | KASKLAS | (SEQ ID NO: 173) | QCSYTAIGNYGHV | (SEQ ID NO: 174) | 3.73E-09 | ○ |
| 5793 | RYTMG | (SEQ ID NO: 167) | IINSGATYYASWAKG | (SEQ ID NO: 169) | GDA | (SEQ ID No.94) | QASQSIGSNLA | (SEQ ID NO: 172) | KASKLAS | (SEQ ID NO: 173) | QCSYTAIGNYGHV | (SEQ ID NO: 174) | 7.30E-10 | ◎ |
| 5795 | RYAMG | (SEQ ID No.96) | IINSGATYYASWAKG | (SEQ ID NO: 169) | GDF | (SEQ ID NO: 170) | QASQSIGSNLA | (SEQ ID NO: 172) | KASKLAS | (SEQ ID NO: 173) | QCSYTAIGNYGHV | (SEQ ID NO: 174) | 1.71E-09 | ○ |
| 5803 | SYTMG | (SEQ ID No.96) | IINSGATYYASWAKG | (SEQ ID No.97) | GDF | (SEQ ID NO: 170) | QASQSIGSNLA | (SEQ ID NO: 172) | KASKLAS | (SEQ ID NO: 173) | QCSYTAIGNYGHV | (SEQ ID NO: 174) | 4.20E-09 | ○ |
| 5810 | RYTMG | (SEQ ID NO: 167) | IIANSGATYYASWAKG | (SEQ ID NO: 169) | GDF | (SEQ ID NO: 170) | QASQSIGSNLA | (SEQ ID NO: 172) | KASKLAS | (SEQ ID NO: 173) | QCSYTAIGNYGHV | (SEQ ID NO: 174) | 6.52E-12 | ◎ |
| 5811 | AYTMG | (SEQ ID No.98) | IINSGATYYASWAKG | (SEQ ID NO: 169) | GDF | (SEQ ID NO: 170) | QASQSIGSNLA | (SEQ ID NO: 172) | KASKLAS | (SEQ ID NO: 173) | QCSYTAIGNAYGHV | (SEQ ID NO: 174) | 1.13E-08 | △ |
| 5844 | RYTMG | (SEQ ID NO: 167) | IINSGATYYASWAKG | (SEQ ID NO: 169) | GDF | (SEQ ID NO: 170) | QASQSAGSNLA | (SEQ ID No.100) | KASKLAS | (SEQ ID NO: 173) | QCSYTAIGNYGHV | (SEQ ID No.99) | 9.82E-09 | ○ |
| 5868 | RYTMG | (SEQ ID NO: 167) | IINSGATYYASWAKG | (SEQ ID NO: 169) | GDF | (SEQ ID NO: 170) | QASQSIGSNLA | (SEQ ID NO: 172) | KASKLAS | (SEQ ID NO: 173) | QCSYTAIGNYGHV | (SEQ ID NO: 174) | 9.04E-09 | ○ |
| 5874 | RYTMG | (SEQ ID NO: 167) | IINSGATYYASWAKG | (SEQ ID NO: 169) | GDF | (SEQ ID NO: 170) | QASQSIGSNLA | (SEQ ID NO: 172) | KASKLAS | (SEQ ID NO: 173) | QSSYTESITFGHV | (SEQ ID NO: 101) | 1.96E-08 | △ |
| 5875 | RYTMG | (SEQ ID NO: 167) | IINSGATYYASWAKG | (SEQ ID NO: 169) | GDF | (SEQ ID NO: 170) | QASQSIGSNLA | (SEQ ID NO: 172) | KTSTLES | (SEQ ID No.102) | QCSYTAIGNYGHV | (SEQ ID NO: 174) | 1.96E-08 | △ |
| 5878 | RYTMG | (SEQ ID NO: 167) | IINSGATYYASWAKG | (SEQ ID NO: 169) | GDF | (SEQ ID NO: 170) | QASQSIGNYLA | (SEQ ID No.103) | KASKLAS | (SEQ ID NO: 173) | QCSYTAIGNYGHV | (SEQ ID NO: 174) | 1.43E-08 | △ |
| 5884 | RYTMG | (SEQ ID NO: 167) | IINSGATYYASWAKG | (SEQ ID NO: 169) | GDF | (SEQ ID NO: 170) | QASEDISNLA | (SEQ ID No.122) | KASTLAS | (SEQ ID No.121) | QSSYTESITFGHV | (SEQ ID No.101) | 7.37E-09 | ○ |

FIG. 2B

| Variant | VH | | | | | | VL | | | | | | rsCD14ST-Fc | Evaluation |
|---|---|---|---|---|---|---|---|---|---|---|---|---|---|---|
| | CDR1 | | CDR2 | | CDR3 | | CDR1 | | CDR2 | CDR3 | | | OD ratio | |
| 5807 | RYTMG | (SEQ ID NO: 167) | IINSGATYYASAAKG | (SEQ ID No.104) | GDF | (SEQ ID NO: 170) | QASQSIGSNLA | (SEQ ID NO: 172) | KASKLAS | (SEQ ID NO: 173) | QCSYTAIGNYGHV | (SEQ ID NO: 174) | 4.3 | ○ |
| 5808 | RYTMG | (SEQ ID NO: 167) | IINSGATYYASWAAG | (SEQ ID No.105) | GDF | (SEQ ID NO: 170) | QASQSIGSNLA | (SEQ ID NO: 172) | KASKLAS | (SEQ ID NO: 173) | QCSYTAIGNYGHV | (SEQ ID NO: 174) | 5.3 | ○ |
| 5809 | RYTMG | (SEQ ID NO: 167) | IINSGATYYASWAKA | (SEQ ID No.106) | GDF | (SEQ ID NO: 170) | QASQSIGSNLA | (SEQ ID NO: 172) | KASKLAS | (SEQ ID NO: 173) | QCSYTAIGNYGHV | (SEQ ID NO: 174) | 5.1 | ○ |
| 5812 | RYTMG | (SEQ ID NO: 167) | IINSGATYYASWGKG | (SEQ ID No.107) | GDF | (SEQ ID NO: 170) | QASQSIGSNLA | (SEQ ID NO: 172) | KASKLAS | (SEQ ID NO: 173) | QCSYTAIGNYGHV | (SEQ ID NO: 174) | 4.5 | ○ |
| 5824 | RYTMG | (SEQ ID NO: 167) | IVSSDCGIYYASWAKG | (SEQ ID No.108) | GDF | (SEQ ID NO: 170) | QASQSIGSNLA | (SEQ ID NO: 172) | KASKLAS | (SEQ ID NO: 173) | QCSYTAIGNYGHV | (SEQ ID NO: 174) | 5.3 | ○ |
| 5826 | RYTMG | (SEQ ID NO: 167) | IYRNIKTYYATWAKG | (SEQ ID No.109) | GDF | (SEQ ID NO: 170) | QASQSIGSNLA | (SEQ ID NO: 172) | KASKLAS | (SEQ ID NO: 173) | QCSYTAIGNYGHV | (SEQ ID NO: 174) | 4.4 | ○ |
| 5827 | RYTMG | (SEQ ID NO: 167) | ISDDQIVYATWAKG | (SEQ ID No.110) | GDF | (SEQ ID NO: 170) | QASQSIGSNLA | (SEQ ID NO: 172) | KASKLAS | (SEQ ID NO: 173) | QCSYTAIGNYGHV | (SEQ ID NO: 174) | 4.2 | ○ |
| 5841 | RYTMG | (SEQ ID NO: 167) | ISDDDLFYASWAKG | (SEQ ID No.111) | GDF | (SEQ ID NO: 170) | QASQSIGSNLA | (SEQ ID NO: 172) | KASKLAS | (SEQ ID NO: 173) | QCSYTAIGNYGHV | (SEQ ID NO: 174) | 4.3 | ○ |
| 5842 | RYTMG | (SEQ ID NO: 167) | IINSGATYYASWAKG | (SEQ ID NO: 169) | GDF | (SEQ ID NO: 170) | QAAQSIGSNLA | (SEQ ID No.114) | KASKLAS | (SEQ ID NO: 173) | QCSYTAIGNYGHA | (SEQ ID No.112) | 4.7 | ○ |
| 5843 | RYTMG | (SEQ ID NO: 167) | IINSGATYYASWAKG | (SEQ ID NO: 169) | GDF | (SEQ ID NO: 170) | QGSQSIGSNLA | (SEQ ID No.115) | KASKLAS | (SEQ ID NO: 173) | QCSYTAIGNYAHV | (SEQ ID No.113) | 4.7 | ○ |
| 5859 | RYTMG | (SEQ ID NO: 167) | IINSGATYYASWAKG | (SEQ ID NO: 169) | GDF | (SEQ ID NO: 170) | QASQSIGSNLA | (SEQ ID NO: 172) | KASKLAS | (SEQ ID NO: 173) | QCSYTAIGNYGHV | (SEQ ID NO: 174) | 4.6 | ○ |
| 5860 | RYTMG | (SEQ ID NO: 167) | IINSGATYYASWAKG | (SEQ ID NO: 169) | GDF | (SEQ ID NO: 170) | QASQSIGSNLA | (SEQ ID NO: 172) | KASKLAS | (SEQ ID NO: 173) | QCSYTAIGNYGHV | (SEQ ID NO: 174) | 5.2 | ○ |
| 5861 | RYTMG | (SEQ ID NO: 167) | IINSGATYYASWAKG | (SEQ ID NO: 169) | GDF | (SEQ ID NO: 170) | QASQSIGSNLA | (SEQ ID NO: 172) | KASKLAS | (SEQ ID NO: 173) | ACSYTAIGNYGHV | (SEQ ID No.116) | 4.5 | ○ |

FIG. 2C

| Variant | VH | | | | | | VL | | | | | | rsCD14ST-Fc | Evaluation |
|---|---|---|---|---|---|---|---|---|---|---|---|---|---|---|
| | CDR1 | | CDR2 | | CDR3 | | CDR1 | | CDR2 | | CDR3 | | OD ratio | |
| 5862 | RYTMG | (SEQ ID No: 167) | IINSGATYYASWAKG | (SEQ ID NO: 169) | GDF | (SEQ ID No: 170) | QASQSIGSNLA | (SEQ ID No: 172) | KASKAAS | (SEQ ID No: 117) | QCSYTAIGNYGHV | (SEQ ID NO: 174) | 4.4 | ○ |
| 5863 | RYTMG | (SEQ ID No: 167) | IINSGATYYASWAKG | (SEQ ID NO: 169) | GDF | (SEQ ID No: 170) | QASQSIGSNLA | (SEQ ID No: 172) | KAAKLAS | (SEQ ID No: 118) | QCSYTAIGNYGHV | (SEQ ID NO: 174) | 5.2 | ○ |
| 5864 | RYTMG | (SEQ ID No: 167) | IINSGATYYASWAKG | (SEQ ID NO: 169) | GDF | (SEQ ID No: 170) | QASQSIGSNAA | (SEQ ID No.119) | KASKLAS | (SEQ ID No: 173) | QCSYTAIGNYGHV | (SEQ ID NO: 174) | 5.7 | ◎ |
| 5865 | RYTMG | (SEQ ID No: 167) | IINSGATYYASWAKG | (SEQ ID NO: 169) | GDF | (SEQ ID No: 170) | AASQSIGSNLA | (SEQ ID No.120) | KASKLAS | (SEQ ID No: 173) | QCSYTAIGNYGHV | (SEQ ID NO: 174) | 4.7 | ○ |
| 5877 | RYTMG | (SEQ ID No: 167) | IINSGATYYASWAKG | (SEQ ID NO: 169) | GDF | (SEQ ID No: 170) | QASEDISNLA | (SEQ ID No.122) | KASTLAS | (SEQ ID No: 121) | QCSYTAIGNYGHV | (SEQ ID NO: 174) | 4.6 | ○ |
| 5884 | RYTMG | (SEQ ID No: 167) | IINSGATYYASWAKG | (SEQ ID NO: 169) | GDF | (SEQ ID No: 170) | QASQNIGSDLS | (SEQ ID No.123) | KASKLAS | (SEQ ID No: 173) | QCSYTAIGNYGHV | (SEQ ID NO: 174) | 4.7 | ○ |
| 5910 | RYTMG | (SEQ ID No: 167) | IINSGATYYASWAKG | (SEQ ID NO: 168) | LDF | (SEQ ID No.124) | QASQSIGSNLA | (SEQ ID No: 172) | KASKLAS | (SEQ ID No: 173) | QCSYTAIGNYGHV | (SEQ ID NO: 174) | 4.2 | ○ |
| 5920 | RYTMG | (SEQ ID No: 167) | IINSGATYYASWAKG | (SEQ ID NO: 168) | SDF | (SEQ ID No.125) | QASQSIGSNLA | (SEQ ID No: 172) | KASKLAS | (SEQ ID No: 173) | QCSYTAIGNYGHV | (SEQ ID NO: 174) | 3.1 | |
| 5926 | RYTMG | (SEQ ID No: 167) | IINSGATYYASWAKG | (SEQ ID NO: 169) | GDF | (SEQ ID No: 170) | QASQSIGSNLA | (SEQ ID No: 172) | KASKLAS | (SEQ ID No: 173) | QCSYTAIGNYGHV | (SEQ ID NO: 174) | 4.4 | ○ |
| 5932 | MYTMG | (SEQ ID No.126) | IINSGATYYASWAKG | (SEQ ID NO: 169) | GDF | (SEQ ID No: 170) | QASQSIGSNLA | (SEQ ID No: 172) | KASKLAS | (SEQ ID No: 173) | QCSYTAIGNYGHV | (SEQ ID NO: 174) | 4.3 | ○ |
| 5933 | PYTMG | (SEQ ID No.127) | IINSGATYYASWAKG | (SEQ ID NO: 169) | GDF | (SEQ ID No: 170) | QASQSIGSNLA | (SEQ ID No: 172) | KASKLAS | (SEQ ID No: 173) | QCSYTAIGNYGHV | (SEQ ID NO: 174) | 4.8 | ○ |
| 5934 | VYTMG | (SEQ ID No.128) | IINSGATYYASWAKG | (SEQ ID NO: 169) | GDF | (SEQ ID No: 170) | QASQSIGSNLA | (SEQ ID No: 172) | KASKLAS | (SEQ ID No: 173) | QCSYTAIGNYGHV | (SEQ ID NO: 174) | 5.1 | ○ |
| 5935 | IYTMG | (SEQ ID No.129) | IINSGATYYASWAKG | (SEQ ID NO: 169) | GDF | (SEQ ID No: 170) | QASQSIGSNLA | (SEQ ID No: 172) | KASKLAS | (SEQ ID No: 173) | QCSYTAIGNYGHV | (SEQ ID NO: 174) | 5.0 | ○ |

FIG. 2D

| Variant | VH CDR1 | | VH CDR2 | VH CDR3 | | VL CDR1 | | VL CDR2 | VL CDR3 | | rsCD14ST-Fc OD ratio | Evaluation |
|---|---|---|---|---|---|---|---|---|---|---|---|---|
| 5937 | DYTMG | (SEQ ID No:130) | IINSGATYYASWAKG | GDF | (SEQ ID NO: 169) | QASQSIGSNLA | (SEQ ID NO: 172) | KASKLAS | QCSYTAIGNYGHV | (SEQ ID NO: 173) (SEQ ID NO: 174) | 4.5 | ○ |
| 5938 | EYTMG | (SEQ ID No:131) | IINSGATYYASWAKG | GDF | (SEQ ID NO: 169) | QASQSIGSNLA | (SEQ ID NO: 172) | KASKLAS | QCSYTAIGNYGHV | (SEQ ID NO: 173) (SEQ ID NO: 174) | 4.5 | ○ |
| 5939 | HYTMG | (SEQ ID No:132) | IINSGATYYASWAKG | GDF | (SEQ ID NO: 169) | QASQSIGSNLA | (SEQ ID NO: 172) | KASKLAS | QCSYTAIGNYGHV | (SEQ ID NO: 173) (SEQ ID NO: 174) | 5.0 | ○ |
| 5940 | IYTMG | (SEQ ID No:133) | IINSGATYYASWAKG | GDF | (SEQ ID NO: 169) | QASQSIGSNLA | (SEQ ID NO: 172) | KASKLAS | QCSYTAIGNYGHV | (SEQ ID NO: 173) (SEQ ID NO: 174) | 4.8 | ○ |
| 5941 | QYTMG | (SEQ ID No:134) | IINSGATYYASWAKG | GDF | (SEQ ID NO: 169) | QASQSIGSNLA | (SEQ ID NO: 172) | KASKLAS | QCSYTAIGNYGHV | (SEQ ID NO: 173) (SEQ ID NO: 174) | 4.0 | ○ |
| 5942 | YYTMG | (SEQ ID No:135) | IINSGATYYASWAKG | GDF | (SEQ ID NO: 169) | QASQSIGSNLA | (SEQ ID NO: 172) | KASKLAS | QCSYTAIGNYGHV | (SEQ ID NO: 173) (SEQ ID NO: 174) | 4.9 | ○ |
| 5943 | GYTMG | (SEQ ID No:136) | IINSGATYYASWAKG | GDF | (SEQ ID NO: 169) | QASQSIGSNLA | (SEQ ID NO: 172) | KASKLAS | QCSYTAIGNYGHV | (SEQ ID NO: 173) (SEQ ID NO: 174) | 4.6 | ○ |
| 5944 | KYTMG | (SEQ ID No:137) | IINSGATYYASWAKG | GDF | (SEQ ID NO: 169) | QASQSIGSNLA | (SEQ ID NO: 172) | KASKLAS | QCSYTAIGNYGHV | (SEQ ID NO: 173) (SEQ ID NO: 174) | 5.0 | ○ |
| 5945 | NYTMG | (SEQ ID No:138) | IINSGATYYASWAKG | GDF | (SEQ ID NO: 169) | QASQSIGSNLA | (SEQ ID NO: 172) | KASKLAS | QCSYTAIGNYGHV | (SEQ ID NO: 173) (SEQ ID NO: 174) | 4.1 | ○ |
| 5946 | WYTMG | (SEQ ID No:139) | IINSGATYYASWAKG | GDF | (SEQ ID NO: 169) | QASQSIGSNLA | (SEQ ID NO: 172) | KASKLAS | QCSYTAIGNYGHV | (SEQ ID NO: 173) (SEQ ID NO: 174) | 4.5 | ○ |
| 5976 | RYTMG | (SEQ ID NO: 167) | IINSGATYYASWAKG | GFF | (SEQ ID No.140) | QASQSIGSNLA | (SEQ ID NO: 172) | KASKLAS | QCSYTAIGNYGHV | (SEQ ID NO: 173) (SEQ ID NO: 174) | 4.7 | ○ |
| 5977 | RYTMG | (SEQ ID NO: 167) | IINSGATYYASWAKG | GSF | (SEQ ID No.141) | QASQSIGSNLA | (SEQ ID NO: 172) | KASKLAS | QCSYTAIGNYGHV | (SEQ ID NO: 173) (SEQ ID NO: 174) | 4.7 | ○ |
| 5978 | RYTMG | (SEQ ID NO: 167) | IINSGATYYASWAKG | GPF | (SEQ ID No.142) | QASQSIGSNLA | (SEQ ID NO: 172) | KASKLAS | QCSYTAIGNYGHV | (SEQ ID NO: 173) (SEQ ID NO: 174) | 4.6 | ○ |

FIG. 2E

| Variant | VH | | | | | | VL | | | | | | rsCD14ST-Fc | Evaluation |
|---|---|---|---|---|---|---|---|---|---|---|---|---|---|---|
| | CDR1 | | CDR2 | | CDR3 | | CDR1 | | CDR2 | | CDR3 | | OD ratio | |
| 5979 | RYTMG | (SEQ ID NO: 167) | IINSGATYYASWAKG | (SEQ ID NO: 169) | GHF | (SEQ ID No.143) | QASQSIGSNLA | (SEQ ID NO: 172) | KASKLAS | (SEQ ID NO: 173) | QCSYTAIGNYGHV | (SEQ ID NO: 174) | 5.5 | ◎ |
| 5980 | RYTMG | (SEQ ID NO: 167) | IINSGATYYASWAKG | (SEQ ID NO: 169) | GIF | (SEQ ID No.144) | QASQSIGSNLA | (SEQ ID NO: 172) | KASKLAS | (SEQ ID NO: 173) | QCSYTAIGNYGHV | (SEQ ID NO: 174) | 5.3 | ○ |
| 5981 | RYTMG | (SEQ ID NO: 167) | IINSGATYYASWAKG | (SEQ ID NO: 169) | GNF | (SEQ ID No.145) | QASQSIGSNLA | (SEQ ID NO: 172) | KASKLAS | (SEQ ID NO: 173) | QCSYTAIGNYGHV | (SEQ ID NO: 174) | 4.4 | ○ |
| 5982 | RYTMG | (SEQ ID NO: 167) | IINSGATYYASWAKG | (SEQ ID NO: 169) | GRF | (SEQ ID No.146) | QASQSIGSNLA | (SEQ ID NO: 172) | KASKLAS | (SEQ ID NO: 173) | QCSYTAIGNYGHV | (SEQ ID NO: 174) | 4.7 | ○ |
| 5983 | RYTMG | (SEQ ID NO: 167) | IINSGATYYASWAKG | (SEQ ID NO: 169) | GDS | (SEQ ID No.147) | QASQSIGSNLA | (SEQ ID NO: 172) | KASKLAS | (SEQ ID NO: 173) | QCSYTAIGNYGHV | (SEQ ID NO: 174) | 5.5 | ◎ |
| 5984 | RYTMG | (SEQ ID NO: 167) | IINSGATYYASWAKG | (SEQ ID NO: 169) | GDP | (SEQ ID No.148) | QASQSIGSNLA | (SEQ ID NO: 172) | KASKLAS | (SEQ ID NO: 173) | QCSYTAIGNYGHV | (SEQ ID NO: 174) | 5.1 | ○ |
| 5985 | RYTMG | (SEQ ID NO: 167) | IINSGATYYASWAKG | (SEQ ID NO: 169) | GDH | (SEQ ID No.149) | QASQSIGSNLA | (SEQ ID NO: 172) | KASKLAS | (SEQ ID NO: 173) | QCSYTAIGNYGHV | (SEQ ID NO: 174) | 4.9 | ○ |
| 5986 | RYTMG | (SEQ ID NO: 167) | IINSGATYYASWAKG | (SEQ ID NO: 169) | GDQ | (SEQ ID No.150) | QASQSIGSNLA | (SEQ ID NO: 172) | KASKLAS | (SEQ ID NO: 173) | QCSYTAIGNYGHV | (SEQ ID NO: 174) | 4.4 | ○ |
| 5987 | RYTMG | (SEQ ID NO: 167) | IINSGATYYASWAKG | (SEQ ID NO: 169) | GDI | (SEQ ID No.151) | QASQSIGSNLA | (SEQ ID NO: 172) | KASKLAS | (SEQ ID NO: 173) | QCSYTAIGNYGHV | (SEQ ID NO: 174) | 5.2 | ○ |
| 5988 | RYTMG | (SEQ ID NO: 167) | IINSGATYYASWAKG | (SEQ ID NO: 169) | GDN | (SEQ ID No.152) | QASQSIGSNLA | (SEQ ID NO: 172) | KASKLAS | (SEQ ID NO: 173) | QCSYTAIGNYGHV | (SEQ ID NO: 174) | 5.6 | ◎ |
| 5989 | RYTMG | (SEQ ID NO: 167) | IINSGATYYASWAKG | (SEQ ID NO: 169) | GDR | (SEQ ID No.153) | QASQSIGSNLA | (SEQ ID NO: 172) | KASKLAS | (SEQ ID NO: 173) | QCSYTAIGNYGHV | (SEQ ID NO: 174) | 4.5 | ○ |
| 6026 | RYTMG | (SEQ ID NO: 167) | IINSGATYYASWAKG | (SEQ ID NO: 169) | GVL | (SEQ ID No.154) | QASQSIGSNLA | (SEQ ID NO: 172) | KASKLAS | (SEQ ID NO: 173) | QCSYTAIGNYGHV | (SEQ ID NO: 174) | 4.6 | ○ |
| 6028 | RYTMG | (SEQ ID NO: 167) | IINSGATYYASWAKG | (SEQ ID NO: 169) | GGE | (SEQ ID No.155) | QASQSIGSNLA | (SEQ ID NO: 172) | KASKLAS | (SEQ ID NO: 173) | QCSYTAIGNYGHV | (SEQ ID NO: 174) | 5.5 | ◎ |
| 6029 | RYTMG | (SEQ ID NO: 167) | IINSGATYYASWAKG | (SEQ ID NO: 169) | GLH | (SEQ ID No.156) | QASQSIGSNLA | (SEQ ID NO: 172) | KASKLAS | (SEQ ID NO: 173) | QCSYTAIGNYGHV | (SEQ ID NO: 174) | 5.1 | ○ |

# ANTI-PRESEPSIN ANTIBODY

CROSS-REFERENCE TO RELATED APPLICATIONS

This application is a Divisional of U.S. application Ser. No. 15/915,658, filed on Mar. 3, 2018, now U.S. Pat. No. 10,676,532, which is a Divisional of U.S. application Ser. No. 14/631,668, filed Feb. 25, 2014, now U.S. Pat. No. 9,951,142, which claims priority from U.S. Provisional Application No. 61/944,674, filed Feb. 26, 2014.

SEQUENCE LISTING

The instant application contains a Sequence Listing which has been submitted electronically in ASCII format and is hereby incorporated by reference in its entirety. Said ASCII copy, created on May 1, 2020, is named sequence.txt and is 58,081 bytes in size.

FIELD OF INVENTION

The present invention relates to anti-presepsin antibodies or an antigen binding antibody fragments thereof, which are useful for measurement of presepsin in a sample.

BACKGROUND OF THE INVENTION

CD14 is a known glycoprotein expressed on the membrane surface of monocytic cells and functions as a receptor of LPS (lipopolysaccharide). There are 2 types of CD14 molecules. One type is the membrane binding-type CD14 (mCD14) expressed on the cell surface. Another type is soluble CD14 (sCD14). sCD14s that have a molecular weight of about 55 kDa to about 49 kDa (hereinafter, referred to as the "high molecular weight sCD14") are known in the art and these sCD14s are reported to show a high value in the blood of a patient with many diseases such as sepsis, acquired immune deficiency syndrome (AIDS), acute respiratory distress syndrome (ARDS) and systemic lupus erythematosus (SLE). For that reason, these high molecular weight sCD14s are not considered as disease-specific markers. See Hayashi, et al., Infection and Immunity, 67: 417-420, 1999; and Lawn, et al., Clinical & Experimental Immunology, 120: 483-487, 2000.

On the other hand, it has been reported that there is a new molecular species of sCD14, sCD14-ST (soluble CD14 antigen subtype, also referred to as presepsin), whose blood concentration is characteristically increased in sepsis patients.

sCD14-ST (presepsin) is characterized by being migrated to 13±2 kDa of the molecular weight in SDS-PAGE under non-reduction conditions of all sCD14s, and it comprises the N terminal part of CD14. sCD14-ST (presepsin) has an amino acid sequence in which the C terminal side is largely deleted compared to the amino acid sequences of high molecular weight sCD14, and unlike the high molecular weight sCD14, sCD14-ST (presepsin) does not have LPS binding ability. In addition, presepsin shows different immunogenicity from that of the high molecular weight sCD14, and therefore the molecules can be distinguished using the antibody. The blood concentration of presepsin specifically increases in sepsis patients (see WO 2005/108429 A1). Moreover, it is reported that the blood concentration of presepsin shows a higher value in the blood of sepsis patients compared to patients with systemic inflammatory response syndrome (SIRS), which is difficult to discriminate from sepsis. Thus, presepsin is considered a specific diagnosis marker of sepsis (Yaegashi, et al., Journal of Infection and Chemotherapy, 11: 234-238, 2005).

A rabbit-derived polyclonal antibody (S68 antibody) and a rat-derived monoclonal antibody (F1146-17-2), which specifically recognized presepsin, have been disclosed (see WO 2005/108429 A1 and WO 2004/044005 A1).

Presently, a measurement system using a rabbit-derived polyclonal antibody as a specific antibody to presepsin is practically used in the measurement of presepsin, and measurement kits to carry out the measurement system are on the market in Europe and Japan (PATHFAST™ Presepsin, Mitsubishi Chemical Medience Corporation).

Acquisition of an anti-human presepsin monoclonal antibody that can be practically used has been attempted, but an antibody having satisfactory performances has not been obtained.

SUMMARY OF THE INVENTION

According to the present invention, an antibody and an antigen-binding antibody fragment thereof that is excellent in the reactivity with presepsin and suitable for measuring presepsin in a sample are provided, whereby enhancement of the quality and the accuracy of presepsin measurement can be achieved. In one aspect, the present invention provides the ability to provide antibodies having high affinity for presepsin that are also adaptable for quantitation of a minor amount of presepsin at the level of a normal person (i.e. one without sepsis), and enables sensitivity improvement compared to measurement systems known in the art. In addition, the present invention provides the ability to provide an antibody which resists the influence of an interfering substance in a sample, which enables measurement in a sandwich ELISA system to avoid influence of an individual background factor of a serum sample and produce measurements with high precision. Such measurements, having high specificity, is possible only with an antibody that specifically binds to only presepsin, and does not specifically bind to high molecular weight sCD14, in the sandwich ELISA system.

Measurement of presepsin using polyclonal antibodies results in several problems, including insurance of the homogeneity between lots, production difficulty, cost, and the like. In one aspect of the present invention, these problems are resolved, whereby an antibody that is excellent in practicality can be provided. In one aspect, this problem may be solved with a monoclonal antibody, which can be produced at the low cost, stably and effectively, and uniform quality of such an antibody can be maintained.

In one aspect, the present invention provides a new monoclonal antibody or an antigen-binding antibody fragment thereof, which is excellent in the reactivity with presepsin and suitable for measuring presepsin in a sample.

In addition, another object of the present invention is to provide a monoclonal antibody or an antigen-binding antibody fragment thereof, which provides a presepsin measurement value that is favorably correlated with the measurement value by the S68 antibody (polyclonal antibody obtained by the immunization of a rabbit using the S68 peptide described in Example 1 of WO 2004/044005 A1).

In addition, another object of the present invention is to provide a monoclonal antibody or an antigen-binding antibody fragment thereof, which provides a presepsin measurement value and that is resistant to influence of an interfering substance (e.g. triglyceride) in a sample, and can make it possible to measure presepsin with high precision even in the case of a sample having a variety of background factors.

Specifically, the present invention may include, but is not limited to, the following embodiments:

(A). An anti-presepsin monoclonal antibody or an antigen-binding antibody fragment thereof, wherein the antibody or the fragment specifically recognizes an epitope consisting of an amino acid sequence of SEQ ID NO.: 1.

(B). The antibody or the antigen-binding antibody fragment thereof according to above (A), wherein the binding between the antibody or the fragment and presepsin is competitive-inhibited by 50% or more in a reaction system that an amino acid residue consisting of a sequence of SEQ ID NO.: 1 is subjected to competitive reaction (absorbance) so that the binding between the antibody or the fragment and presepsin is inhibited.

(C). The antibody or the antigen-binding antibody fragment thereof according to above (B), wherein the reaction system is sandwich ELISA using (a) the above antibody or the fragment and (b) F1106-13-3 antibody or F1031-8-3 antibody.

(D). The antibody or the antigen-binding antibody fragment according to above (A), wherein the competitive inhibition for the binding between the antibody or the fragment and presepsin by an amino acid residue is less than 20%, wherein the amino acid residue is consisting of a sequence in which the aspartic acid at position 8 in Sequence ID No. 1 is substituted with alanine.

(E). The antibody or the antigen-binding antibody fragment thereof according to above (A) or (B), wherein the antibody or the fragment binds to presepsin in less than $10^{-8}$M of an affinity (KD).

(F). The antibody or the antigen-binding antibody fragment thereof according to any one of above (A) to (C), wherein the antibody or the fragment is produced using a peptide according to SEQ ID NO.: 2 as an administration antigen.

(G). The antibody or the antigen-binding antibody fragment thereof according to above (A), wherein the antibody or the fragment does not specifically bind to high molecular weight soluble CD14.

(H). The antibody or the antigen-binding antibody fragment thereof according to any one of above (A) to (D), wherein binding activity of the antibody or the fragment with presepsin shows 10,000 folds or more improvement in the presepsin concentration ratio in comparison with binding activity of a rat derived anti-presepsin antibody (F1146-17-2) with presepsin.

(I). The antibody or the antigen-binding antibody fragment thereof according to above (A), wherein the ratio of the sample which exhibits the separation degree of the presepsin measurement value of ±20% or less at the time of having TG concentration of 20 mg/mL in a sample indicates 50% or more in TG interference test on multiple samples performed by using the above antibody or the fragment.

(J). The antibody or the antigen binding antibody fragment thereof described in any one of above (A) to (E), wherein the antibody or the fragment does not specifically bind to high molecular weight soluble CD14.

(K). The antibody or the antigen-binding antibody fragment thereof according to above (A), wherein the presepsin measurement value obtained by using the above antibody or the fragment exhibits 0.9 or more correlation coefficient with the measurement value obtained by using S68 antibody.

(L). An anti-presepsin antibody or an antigen-binding antibody fragment thereof comprising,
  (a) VH comprising heavy chain variable region (VH) complementarity determination region (CDR)1 consisting of an amino acid sequence of SEQ ID NO.: 4, VH CDR2 consisting of an amino acid sequence of SEQ ID NO.: 5, and VH CDR3 consisting of an amino acid sequence of SEQ ID NO.: 6, and VL comprising light chain variable region (VL) CDR1 consisting of an amino acid sequence of SEQ ID NO.: 19, VL CDR2 consisting of an amino acid sequence of SEQ ID NO.: 20, and VL CDR3 consisting of an amino acid sequence of SEQ ID NO.: 21;
  (b) VH comprising VH CDR1 consisting of an amino acid sequence of SEQ ID NO.: 7, VH CDR2 consisting of an amino acid sequence of SEQ ID NO.: 8, and VH CDR3 consisting of an amino acid sequence of SEQ ID NO.: 9, and VL comprising VL CDR1 consisting of an amino acid sequence of SEQ ID NO.: 22, VL CDR2 consisting of an amino acid sequence of SEQ ID NO.: 23, and VL CDR3 consisting of an amino acid sequence of SEQ ID NO.: 24; or
  (c) VH comprising VH CDR1 consisting of an amino acid sequence of SEQ ID NO.: 10, VH CDR2 consisting of an amino acid sequence of SEQ ID NO.: 11, and VH CDR3 consisting of an amino acid sequence of SEQ ID NO.: 12, and VL comprising VL CDR1 consisting of an amino acid sequence of SEQ ID NO.: 25, VL CDR2 consisting of an amino acid sequence of SEQ ID NO.: 26, and VL CDR3 consisting of an amino acid sequence of SEQ ID NO.: 27.
  (d) VH comprising VH CDR1 consisting of an amino acid sequence of SEQ ID NO.: 7, VH CDR2 consisting of an amino acid sequence of SEQ ID NO.: 97, and VH CDR3 consisting of an amino acid sequence of SEQ ID NO.: 9, and VL comprising VL CDR1 consisting of an amino acid sequence of SEQ ID NO.: 22, VL CDR2 consisting of an amino acid sequence of SEQ ID NO.: 23, and VL CDR3 consisting of an amino acid sequence of SEQ ID NO.: 24.
  (e) VH comprising VH CDR1 consisting of an amino acid sequence of SEQ ID NO.: 7, VH CDR2 consisting of an amino acid sequence of SEQ ID NO.: 8, and VH CDR3 consisting of an amino acid sequence of SEQ ID NO.: 94, and VL comprising VL CDR1 consisting of an amino acid sequence of SEQ ID NO.: 22, VL CDR2 consisting of an amino acid sequence of SEQ ID NO.: 23, and VL CDR3 consisting of an amino acid sequence of SEQ ID NO.: 24.

(M). The antigen-binding antibody fragment according to any one of above (A) to (L), wherein the fragment is an antigen-binding antibody fragment selected from the group consisting of Fab, Fab', F (ab')2, single-stranded antibody (scFv), dimerized V region (diabody), disulfide-stabilized V region (dsFv), sc (Fv)2, a polypeptide comprising CDR, a polypeptide comprising a heavy chain variable region and a polypeptide comprising a light chain variable region.

(N). A polynucleotide that encodes the antibody or the antigen-binding antibody fragment thereof according to any one of above (A) to (M).

(O). A recombinant vector comprising the polynucleotide according to above (N).

(P). A transformed strain obtained by introducing the recombinant vector according to above (O) to a host cell.

(Q). The transformed strain according to above (P), wherein the host cell is a CHO cell.

(R). A method of producing an antibody or an antigen-binding antibody fragment thereof, wherein the method comprises the step of culturing the transformed strain according to above (P) or (Q).

(S). A method of measuring presepsin, wherein the method comprises at least the step of contacting with the antibody or the antigen-binding antibody fragment according to any one of above (A) to (M) and a sample containing presepsin.

(T). A method of detecting sepsis or assisting detection/diagnosis of sepsis, comprising at least the steps as described below:

(a) step of measuring the presepsin concentration in a sample from a subject using the antibody or the fragment according to above (A) to (M), (b) step of determining whether the presepsin concentration is a high value in comparison with a cut-off value or not.

(U). A kit for measuring presepsin, wherein the kit comprises at least the antibody or the antigen-binding antibody fragment according to any one of above (A) to (M).

(V). The kit according to above (U), wherein the kit is a kit for detecting sepsis or assisting in the detection or diagnosis of sepsis.

(W). A method of screening an anti-presepsin antibody, wherein the method comprises at least the steps as described below:

1) a step obtaining a candidate anti-presepsin antibody; and 2) a step of selecting the antibody, in which the binding between the antibody and presepsin is competitively-inhibited by 50% or more in a reaction system wherein an amino acid residue consisting of SEQ ID NO.: 1 is introduced to create a competitive reaction so that the binding between said antibody and presepsin is inhibited.

(X). An anti-presepsin monoclonal antibody or an antigen-binding antibody fragment thereof, wherein the antibody or the antigen-binding antibody fragment specifically recognizes an epitope consisting of SEQ ID NO.: 1, wherein the antibody or the antigen-binding antibody fragment comprises, a VH comprising a VH CDR1 consisting of the sequence $X_1X_2X_3MX4$, a VH CDR2 consisting of the sequence $IX_5X_6X_7X_8YAX_9X_{10}X_{11}X_{12}X_{13}$, and a VH CDR3 consisting of the sequence $X_{14}X_{15}X_{16}$; and a VL comprising a VL CDR1 consisting of the sequence $X_{17}X_{18}X_{19}X_{20}X_{21}X_{22}X_{23}X_{24}$, a VL CDR2 consisting of the sequence $KX_{25}X_{26}X_{27}X_{28}X_{29}S$, and a VL CDR3 consisting of the sequence $X_{30}X_{31}X_{32}YX_{33}X_{34}X_{35}X_{36}X_{37}$; wherein $X_1$ is R, S, A, M, P, V, I, D, E, H, T, Q, Y, G, K, N, W, L, F or C; $X_2$ is Y or F; $X_3$ is A, W, or T; $X_4$ is G or S; $X_5$ is I or V; $X_6$ may be NSGA (SEQ ID NO: 157), YRNIK (SEQ ID NO: 158), ANSGA (SEQ ID NO: 159), SSDGG (SEQ ID NO: 160), SDIDQ (SEQ ID NO: 161), or SDIDD (SEQ ID NO: 162); $X_7$ is T, I or L; $X_8$ is Y, V or F; $X_9$ is S or T; $X_{10}$ is W or A; $X_{11}$ is A or G; $X_{12}$ is K or A; $X_{13}$ is G or A; $X_{14}$ is G, A, L, or S; $X_{15}$ is D, F, S, P, H, I, N, R, V, G or L; $X_{16}$ is F, A, S, P, H, D, I, N, R, L, E or H; $X_{17}$ is Q or A; $X_{18}$ is A or G; $X_{19}$ is S or A; $X_{20}$ is QS, ED, or QN; $X_{21}$ I or A; $X_{22}$ is GSN (SEQ ID NO: 182), ISN (SEQ ID NO: 183), GSD (SEQ ID NO: 184), or SNY (SEQ ID NO: 185); $X_{23}$ is L or A; $X_{24}$ is A or S; $X_{25}$ is A or T; $X_{26}$ is S or A; $X_{27}$ is K or T; $X_{28}$ is L or A; $X_{29}$ is A or E; and $X_{30}$ is Q or A; $X_{31}$ is C or S; $X_{32}$ is S or T; $X_{33}$ is T or Y; $X_{34}$ is AIGNY (SEQ ID NO: 163), ESTTF (SEQ ID NO: 164), AIGNAY (SEQ ID NO: 165), or RSTTTY (SEQ ID NO: 166); $X_{35}$ is G or A; $X_{36}$ is H or N; and $X_{37}$ is V, A, or T.

(Y). rsCD14ST-Fc comprising a sequence of Position 1 to Position 64 of Sequence ID NO: 3 (human full length soluble CD14), and a heavy chain Fc region of an antibody (Z). The rsCD14ST-Fc according to above (Y), wherein a sequence facilitating cutting is inserted between a sequence of Position 1 to Position 64 of Sequence ID NO: 3 (human full length soluble CD14), and a heavy chain Fc region of an antibody (AA). The rsCD14ST-Fc according to above (Z), wherein the sequence facilitating cutting is a thrombin recognizing sequence (BB). The rsCD14ST-Fc according to any one of above (Y) to (AA), wherein the heavy chain Fc region of an antibody is an Fc region of a human-derived IgG1 antibody heavy chain.

(CC). A process for producing rsCD14ST-Fc comprising a step of inserting a vector comprising a sequence of Position 1 to Position 64 of Sequence ID NO: 3 (human full length soluble CD14), and a heavy chain Fc region of an antibody into a host cell, and culturing the host cell.

(DD). A process for producing rsCD14-ST comprising a step of cutting the Fc region of rsCDST-Fc according to above (CC).

Hereinbelow, the present invention is described in more detail.

BRIEF DESCRIPTION OF FIGURES

FIG. 2A shows antibody variants obtained by the processes described in example 8 and example 12. FIG. 2B shows antibody variants obtained by the processes described in example 8 and example 12. FIG. 2C shows antibody variants obtained by the processes described in example 8 and example 12. FIG. 2D shows antibody variants obtained by the processes described in example 8 and example 12. FIG. 2E shows antibody variants obtained by the processes described in example 8 and example 12.

DETAILED DESCRIPTION OF THE INVENTION

Figure 1A:
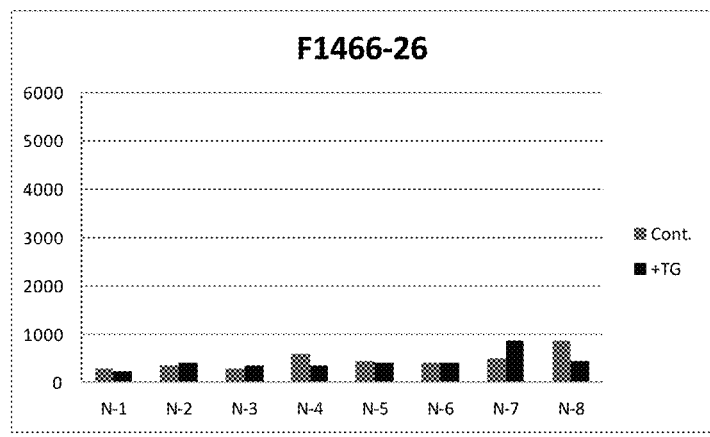
FIG. 1 shows the results from a series of TG interference tests of different antibodies. Panel (A) shows F1466-26, panel (B) shows F1466-5, and panel (C) shows F1466-19.

As provided herein, plurality of monoclonal antibodies were obtained from a plurality of hybridomas obtained by immunizing a rabbit with the S68 peptide via a plurality of selection steps, such as binding activity with the S68 peptide, and binding activity with presepsin. An ELISA system was constructed for measuring presepsin. As a result of investigating the reactivity with presepsin, antibodies were obtained, wherein the reactivity of the antibody with presepsin was improved by about 10,000 folds in comparison with an ELISA system using F1146-17-2 (monoclonal antibody obtained by the immunization of a rat with the S68 peptide described in Example 2 of WO 2004/044005 A1). The amino acid sequence of the CDR part of the F1146-17-2 variable region is described in SEQ ID NO.: 42 to SEQ ID NO.: 47.

Presepsin values in the blood of plural sepsis patients were measured in the ELISA system using each of these rabbit monoclonal antibodies, and analysis for correlation with the measurement values by the ELISA system using S68 antibody was performed. As a result, it was determined that there were some antibodies showing a high correlation and some antibodies showing low correlation. It was further determined that interference of triglyceride (TG) in a sample can be involved in the difference in correlation values. In order to obtain an antibody that is favorably correlated with the presepsin measurement value of the S68 antibody, that resists interference of TG in a sample, and that is suitable for measurement of presepsin in a sample, research was continued, and it was determined that a difference is generated in performance of an antibody depending on the epitope which is recognized by the antibody.

It was determined that an antibody showing preferable performance in presepsin measurement recognizes an amino acid sequence represented by SEQ ID NO.: 1 (krvdadadpr; or the region corresponding to Position 52 to Position 61 in Sequence No. 3 (human full length soluble CD14)). This is a novel epitope which was first discovered by the present invention, and is hereinafter referred to as P03 or SEQ ID NO.: 1.

An antibody recognizing this P03 sequence as an epitope was competitively-inhibited in a reaction between the antibody and presepsin by 50% or more. On the other hand, competition inhibition for a reaction between the antibody and presepsin by each amino acid residue consisting of SEQ ID NO: 35 to SEQ ID NO: 41 was less than 20%, which means the competition inhibition by an amino acid residue consisting of Sequence ID NO: 36 (corresponding to Position 49 to Position 58 of human full length soluble CD14: also referred to as P02 sequence), an amino acid residue consisting of Sequence ID NO: 37 (corresponding to Position 55 to Position 64 of human full length soluble CD14: also referred to as P04 sequence), or an amino acid residue consisting of Sequence ID NO: 38 (corresponding to Position 58 to Position 67 of human full length soluble CD14: also referred to as P05 sequence) was less than 20%. Thus, it was determined that an antibody recognizing the P03 sequence as an epitope has high specificity for the P03 sequence.

At the same time, it was also seen that, among antibodies obtained from hybridomas, antibodies recognizing the P04 sequence and the P05 sequence in presepsin are not suitable for measurement of presepsin, as these antibodies are susceptible to interference from TG in a sample at the time of presepsin measurement, and so on. In this way, it was unexpected that a slight difference in the position of the epitope recognized by an antibody influences performance of the antibody.

In addition, in an amino acid residue in which the position 8 aspartic acid of the P03 sequence (Sequence ID NO: 1) is substituted with alanine, competition inhibition for a reaction between the antibody and presepsin was less than 20%. On the other hand, it was discovered that an amino acid residue in which any of amino acids of position 2 to position 7, position 9 and position 10 of the P03 sequence (Sequence ID NO: 1) are substituted with alanine (or glycine) competitively-inhibits a reaction between the antibody and presepsin by 50% or more.

Further, in order to make an antibody having preferable performance for presepsin measurement, alterations of the CDR sequences were performed based on sequences of antibodies recognizing the P03 sequence as an epitope. In addition, antibodies were made using a phage display method. The resulting antibodies were selected based on a standard to obtain antibodies which are equal to or have better performance than that of antibodies obtained from hybridomas.

Antibodies recognizing the P03 sequence as an epitope, which were obtained from hybridomas, and selected altered antibodies were obtained and confirmed to have extremely high affinity for presepsin, and resist the influence of an interfering substance (particularly, triglyceride) in a sample. These antibodies are favorably correlated with a measurement system using the S68 antibody. These antibodies are suitable for measurement of presepsin in a sample, in for example, a sandwich ELISA assay for presepsin measurement.

It is to be understood that methods and compositions described herein are not limited to the particular embodiments described, and as such may, vary. It is also to be understood that the terminology used herein is for the purpose of describing particular embodiments only, and is not intended to be limiting. The scope of the present technology will be limited only by the appended claims.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

1. An Anti-Presepsin Antibody or an Antigen-Binding Antibody Fragment Thereof, Wherein the Antibody or the Fragment Specifically Recognizes an Epitope Consisting of an Amino Acid Sequence of SEQ ID NO.: 1.

In one embodiment, the present invention relates to an anti-presepsin antibody or an antigen binding antibody fragment thereof, wherein the antibody or the fragment specifically recognizes an amino acid sequence of SEQ ID NO.: 1 as a novel epitope of presepsin.

The expression "specifically recognizes an epitope consisting of an amino acid sequence of Sequence ID NO: 1" indicates that the antibody specifically recognizes, as an epitope, a sequence corresponding to an amino acid sequence of Sequence ID NO: 1 among the sequences of presepsin.

As used herein, the phrase "antigen-binding antibody fragment" indicates, among the partial fragments of an antibody specifically recognizing an epitope consisting of an amino acid sequence of Sequence ID NO: 1, a fragment having the same antigen binding property as the original antibody.

As used herein, "sequence identity" or "sequence homology" refers to a relationship between two or more polynucleotide sequences or amino acid sequences, namely a reference sequence and a given sequence to be compared with the reference sequence. Sequence identity or homology is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or the residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk A. N., ed., Oxford University Press, New York (1988); Biocomputing: Informatics and Genome Projects, Smith D. W., ed., Academic Press, New York (1993); Computer Analysis of Sequence Data, Part I, Griffin A. M., and Griffin H. G., eds., Humana Press, New Jersey (1994); Sequence Analysis in Molecular Biology, von Heinge G., Academic Press (1987); Sequence Analysis Primer, Gribskov M. and Devereux J., eds., M. Stockton Press, New York (1991); and Carillo H., and Lipman D., SIAM J. Applied Math., 48:1073 (1988). Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux et al., *Nuc. Ac. Res.,* 12(1):387 (1984)), BLASTP, BLASTN and FASTA (Altschul et al, *J. Molec. Biol,* 215:403-410 (1990)). The BLASTX program is publicly available from NCBI and other sources (BLAST Manual, Altschul et al., NCBI, NLM, NIH, Bethesda, Md. 20894; Altschul et al. *J. Molec. Biol,* 215:403-410 (1990)). These programs optimally align sequences using default gap weights in order to produce the highest level of sequence identity between the given and reference sequences.

The method for determining an epitope is not particularly limited in the present invention, for example the determination can be made by the method described in Example 6.

The antibody of the present invention may be characterized by competitive-inhibition of 50% or more for the binding between the antibody and presepsin according to a reaction system (preferably using absorbance) in which P03 peptide (an amino acid sequence represented by Sequence ID NO: 1) is used for competitive reaction to inhibit the binding between the antibody and presepsin. Preferably, the reaction system is sandwich ELISA. More preferably, the reaction system is sandwich ELISA using (a) the antibody or the fragment of the present invention and (b) F1106-13-3 antibody or F1031-8-3 antibody. The amino acid sequence represented by Sequence ID NO: 1 corresponds to position 52 to position 61 of the amino acid sequence (Sequence ID NO: 3) of human full length soluble CD14.

Preferably, the competitive-inhibition for the binding between the antibody of the present invention and presepsin is less than 20% by P01 peptide (the amino acid sequence represented by position 46 to position 55 of SEQ ID NO: 3), P02 peptide (the amino acid sequence represented by position 49 to position 58 of the same sequence), P05 peptide (the amino acid sequence represented by position 58 to position 67 of the same sequence), P06 peptide (the amino acid sequence represented by position 61 to position 70 of the same sequence), P07 peptide (the amino acid sequence represented by position 64 to position 73 of the same sequence), or P08 peptide (the amino acid sequence represented by position 67 to position 76 of the same sequence). Preferably, the competitive-inhibition for the binding between the antibody of the present invention and presepsin is less than 20% by P04 peptide (the amino acid sequence represented by position 55 to position 64 of SEQ ID NO: 3).

Alternatively, as one of the other methods of determining an epitope, it is also possible to see binding activity between a partial sequence (e.g. P03 peptide) of an objective antigen, and an antibody, as described in, for example, Example 9-(4). For instance, in one aspect the present invention provides an anti-presepsin antibody that will bind P03 or an amino acid sequence with 90% sequence identity or greater. The target epitope may share 90, 91, 92, 93, 94, 95, 96, 97, 98, 99, or 100% sequence identity with P03. In some embodiments, the anti-prespsin antibody specific for a sequence sharing 90% sequence identity or greater with P03 may be a monoclonal antibody.

In one aspect, an antibody of the present invention is an antibody which specifically recognizes presepsin.

Presepsin (sCD14-ST) is a soluble fragment of CD14 and indicates a substance having the following properties 1) to 3).

1) Molecular weight of 13±2 kDa according to SDS-PAGE under non-reducing conditions,
2) It has an amino acid sequence of position 1 to position 11 of Sequence ID NO: 3 at the N terminal sequence, and
3) It specifically binds to an antibody prepared by using a peptide consisting of 16 amino acid residues described in Sequence ID NO: 2 for the antigen.

As used herein, presepsin means human presepsin, unless particularly illustrated otherwise. In addition, in the present invention, presepsin may be a substance having the activity of presepsin, such as not only a presepsin standard (rsCD14-ST described in Example 16 of WO 2005/108429) but also rsCD14ST-Fc (as described in Example 9-(2) below), and the like.

As described herein, the "antibody specifically recognizing" means an antibody which immunologically recognizes a subject for specific recognition and/or an antibody which shows a typical antigen-antibody reaction with a subject for specific recognition. When the binding between the antibody and subject for specific recognition is expressed by affinity, the equilibrium dissociation constant (KD) is generally less than $10^{-7}$ M. An antibody of the present invention specifically recognizes presepsin only. The main soluble CD14 present in human blood is soluble CD14 of about 55 kDa and about 49 kDa (high molecular weight sCD14). An antibody of the present invention does not specifically bind to the high molecular weight sCD14. As for the high molecular weight sCD14, the human full length CD14 consisting of an amino acid sequence described in Sequence ID NO: 3 may be used or it may be prepared by affinity column adsorption using 3C10 antibody from body fluid of a normal human, for example (see, Example 23 of WO 2005/108429).

In one aspect, an antibody or its antigen binding antibody fragment of the present invention has excellent reactivity for presepsin, and therefore it is useful for measurement of presepsin in a sample. For example, presepsin in a sample may be measured by establishing a sandwich ELISA system by using an antibody or its antigen binding antibody fragment of the present invention.

Compared to F1146-17-2 (a monoclonal antibody derived from a rat, described in Example 2 of WO 2004/044005), an antibody or its antigen binding antibody fragment of the present invention is more suitable for detection of presepsin present in a trace amount in a sample, in view of the fact that the reactivity with presepsin is enhanced by about 10,000 times in a sandwich ELISA system (Example 4). In other words, compared to F1146-17-2, an antibody or its antigen binding antibody fragment of the present invention may be characterized by having reactivity with presepsin which is enhanced by 10,000 times or more in terms of ratio of presepsin concentration.

In a patient having sepsis, it has been reported that the blood concentration of presepsin is characteristically increased. An antibody or its antigen binding antibody fragment of the present invention is desirably used for detection of sepsis. An antibody of the present invention or an antigen-binding antibody fragment thereof is preferably an antibody or an antigen-binding antibody fragment thereof for which a difference in the presepsin measurement value is seen when sandwich ELISA is constructed using the present antibody, and a sepsis patient sample and a normal person sample are measured, as shown in Example 1.

An antibody or its antigen binding antibody fragment of the present invention is suitably an antibody which does not have a problem with the influence of an interfering substance in a sample when measurement of presepsin in a sample is performed by establishing a measurement system. For instance, an antibody of the present invention may resist interference from TG.

In the present invention, an interfering substance means a substance of which the presence potentially has an influence on the measurement value of presepsin (hereinbelow, also referred to as "interfering"). Examples thereof include triglyceride (also referred to as TG), bilirubin, hemoglobin, rheumatoid factor, and cholesterol. In the present invention, the preferred interfering substance for evaluation of an antibody is triglyceride (TG).

As one evaluation indicator of the interference test, the deviation of the presepsin measurement value at the time of adding a certain amount of an interfering substance to a sample from the presepsin measurement value from the same sample without adding any interfering substance can be expressed as a separation degree (%). Moreover the separation degree (%) can be used for an evaluation indicator of the interference test. The separation degree of a measurement value according to the addition of an interfering substance is expressed as follows:

Separation degree (%)={(Presepsin measurement value after adding an interfering substance)−(Presepsin measurement value without adding an interfering substance)}/(Presepsin measurement value without adding an interfering substance)×100.

The term "dissociation degree" is used interchangeably with "separation degree" in the specification.

As used herein, the expressions "resists interference" or "does not have a problem with the influence of an interfering substance" can be described as follows: in an interference test using multiple samples, for example, a ratio of the sample exhibiting the separation degree of ±20% or less, and more preferably ±10% or less is high, in which the separation degree indicates the value obtained from measurement of presepsin according to the addition of a certain amount of an interfering substance. The expression "a ratio of the sample is high" in multiple samples generally indicates 50% or more, preferably 60% or more, more preferably 70% or more, even more preferably 80% or more, and particularly preferably 90% or more of multiple samples.

With regard to TG interference test, for example, it is possible that the interference test is performed for multiple samples and those having a high ratio of the sample which exhibits a separation degree of the presepsin measurement value of ±20% or less, and more preferably ±10% or less, when the TG concentration is 20 mg/mL in a sample by adding TG, are used as one indicator. One preferred embodiment of the present invention is when the TG interference test is performed by using a measurement system using an antibody of the present invention, wherein the antibody exhibits a high ratio of a sample in which the separation degree of the presepsin measurement value is ±20% or less, and more preferably ±10% or less, when the TG concentration is 20 mg/mL.

Alternatively, for example, a separation degree of the presepsin measurement value when the concentration of TG in a sample is 20 mg/mL can be obtained in a plurality of samples, and it may be used as one index that an average of the separation degree is ±20% or less, and more preferably ±10% or less. One of preferable embodiments of an antibody of the present invention is an antibody in which an average of a separation degree of the presepsin measurement value at the concentration of TG in a sample of 20 mg/mL exhibits ±20% or less, and more preferably ±10% or less, when a TG interference test regarding a plurality of samples is performed by a measurement system using the antibody.

In NCEP-ATPIII which is a guideline for dyslipidemia in USA, it is described that less than TG150 mg/dL is normal, TG150 to 200 mg/dL is a borderline, TG200 to 499 mg/dL is a high value (high), and 500 mg/dL or more is a remarkable high value (very high). The TG concentration of 20 mg/mL (=2000 mg/dL) in a sample can be said to be in the state where the TG concentration is extremely high, in light of the aforementioned standard.

In a TG interference test of the present Example, a separation degree of the presepsin measurement value is measured at three points of the TG concentration of a sample of 6.7 mg/mL, 13.3 mg/mL, and 20 mg/mL. There was seen a tendency that a separation degree is also small at the TG concentration of a sample of 6.7 mg/mL and 13.3 mg/mL in an antibody in which a separation degree is small at the TG concentration of a sample of 20 mg/mL (measurement system) in comparison with an antibody in which the separation degree is large.

The TG interference test may be performed using normal person human serum. Since a sample of a normal person (i.e. a non-septic person) has a low presepsin concentration, when it undergoes TG interference, a separation degree of the measurement value easily becomes large. By the present test, if a minor amount of presepsin in a sample can be measured, it is indicative that the test has good precision. For example, a separation degree of the presepsin measurement value at the TG concentration in a sample is preferably ±100% or less, more preferably ±70% or less, further preferably ±50% or less, and particularly preferably ±20% or less. It is desirable to perform the test using a plurality of samples, as in the aforementioned test.

Further, an antibody or the antigen binding antibody fragment of the present invention may be also evaluated based on comparison between the separation degree of presepsin measurement value obtained by adding an interference substance for the antibody and the separation degree of S68 antibody under the same conditions. According to one preferred embodiment, an antibody of the present invention and a S68 antibody exhibit similar separation degrees.

With regard to the TG interference test, the evaluation may be also made by having a high ratio of the sample which exhibits 20% or less and more preferably 10% or less of a difference between the separation degree of the presepsin measurement value when the TG concentration is 20 mg/mL in a sample according to addition of TG in a measurement system using the antibody of the present invention and the separation degree of S68 antibody under the same conditions. With regard to the difference in separation degree, when the separation degree of the measurement value obtained from the antibody of the present invention is +5% and the separation degree of the measurement value obtained from S68 antibody is −10%, for example, the difference in separation degree was calculated as 15%. As the sample used in the interference test, the samples described in the second embodiment of the present invention can be used. In the case of a TG interference test, the sample is preferably serum or plasma.

As for an antibody or the antigen binding antibody fragment of the present invention, an antibody exhibiting good correlation with the measurement value obtained by using S68 antibody is preferable when presepsin in a sample is measured by establishing a measurement system. "Good correlation" means that the correlation coefficient is preferably 0.9 or more, and more preferably 0.95 or more.

An antibody or its antigen binding antibody fragment of the present invention may specifically bind to presepsin, and the affinity for presepsin (equilibrium dissociation constant, K D value) is preferably less than $10^{-7}$ M, more preferably less than $10^{-8}$M, even more preferably less than $10^{-9}$ M, particularly preferably less than $10^{-10}$ M, and most preferably less than $10^{-11}$ M. The equilibrium dissociation constant of an antibody or its antigen binding antibody fragment of the present invention for presepsin is preferably in the range of $10^{-7}$M to $10^{-14}$M, more preferably in the range of $10^{-8}$M to $10^{-13}$M. RsCD14ST-Fc can be used as Presepsin. Affinity (equilibrium dissociation constant, KD value) can be measured using, for example, BIACORE (GE Healthcare).

In one of preferable embodiments of the present invention, affinity (KD value) for presepsin of the antibody of the present invention or an antigen-binding antibody fragment thereof is excellent in comparison with affinity for presepsin of the S68 antibody. It is desirable that affinity (KD value) for rsCD14ST-Fc (described in Presepsin: Example 9-(2)) of an antibody of the present invention or an antigen-binding antibody fragment thereof exhibits a numerical value at the same level as, or lower than 1.08E-08 of affinity (KD value) for rsCD14ST-Fc for the S68 antibody, and it is desirable that the affinity exhibits preferably ½ of a KD value of the S68 antibody (5.40E-09) or less, and further preferably ⅒ of a KD value of the S68 antibody (1.08E-09) or less.

One of preferable embodiments of the present invention is excellent binding activity of an antibody of the present invention or an antigen-binding antibody fragment thereof with presepsin in comparison to the S68 antibody.

For example, rsCD14ST-Fc (presepsin) is fixed to a solid phase, and is reacted with an antibody, and binding activity of an antibody with presepsin may be evaluated by absorbance or the like, as described in Example 10-(2).

When a test is performed according to Example 10, and absorbance at a reaction of the S68 antibody and rsCD14ST-Fc is determined to be 1, a ratio of absorbance when the antibody of the present invention and rsCD14ST-Fc are reacted is preferably 1 or more, more preferably 2 or more, further preferably 4 or more, and particularly preferably 5.5 or more.

In one aspect, the present invention provides for an antibody described in any of the following way.

In one embodiment, the present invention provides an anti-presepsin antibody. Because the following antibody of (a), (b), or (c) and the antigen binding antibody fragment thereof specifically recognize an epitope consisting of an amino acid sequence of Sequence ID NO: 1 present on presepsin, they are preferred examples of a first embodiment. More preferable is an antibody of (a) or (b), or an antigen-binding antibody fragment thereof.

(a) an antibody or an antigen binding antibody fragment thereof comprising VH comprising VH CDR1 consisting of an amino acid sequence of SEQ ID NO: 4, VH CDR2 consisting of an amino acid sequence of SEQ ID NO: 5, and VH CDR3 consisting of an amino acid sequence of SEQ ID NO: 6, and VL comprising VL CDR1 consisting of an amino acid sequence of SEQ ID NO: 19, VL CDR2 consisting of an amino acid sequence of SEQ ID NO: 20, and VL CDR3 consisting of an amino acid sequence of SEQ ID NO: 21;

(b) an antibody or an antigen binding antibody fragment thereof comprising VH comprising VH CDR1 consisting of an amino acid sequence of SEQ ID NO: 7, VH CDR2 consisting of an amino acid sequence of SEQ ID NO: 8, and VH CDR3 consisting of an amino acid sequence of SEQ ID NO: 9, and VL comprising VL CDR1 consisting of an amino acid sequence of SEQ ID NO: 22, VL CDR2 consisting of an amino acid sequence of SEQ ID NO: 23, and VL CDR3 consisting of an amino acid sequence of SEQ ID NO: 24; or (c) an antibody or an antigen binding antibody fragment thereof comprising VH comprising VH CDR1 consisting of an amino acid sequence of SEQ ID NO: 10, VH CDR2 consisting of an amino acid sequence of SEQ ID NO: 11, and VH CDR3 consisting of an amino acid sequence of SEQ ID NO: 12, and VL comprising VL CDR1 consisting of an amino acid sequence of SEQ ID NO: 25, VL CDR2 consisting of an amino acid sequence of SEQ ID NO: 26, and VL CDR3 consisting of an amino acid sequence of SEQ ID NO: 27.

In one embodiment, the present invention also provides an antibody or an antigen binding antibody fragment thereof comprising an amino acid sequence of CDR region described in FIGS. 2A-2E. These antibodies also specifically recognize an etitope consisting of an amino acid sequence of Sequence ID NO: 1 present on presepsin. More preferable is an antibody comprising the CDR amino acid sequence of 5793, 5810, 5864, 5979, 5983, 5988, or 6028, or an antigen-binding antibody fragment thereof.

In another aspect, the present invention provides a polypeptide comprising CDR described in any of the followings. More preferable is a polypeptide of (i), (ii), (iv) or (v).

(i) a polypeptide comprising VH CDR1 consisting of a sequence of SEQ ID NO: 4, VH CDR2 consisting of a sequence of SEQ ID NO: 5, and VH CDR3 consisting of a sequence of SEQ ID NO: 6

(ii) a polypeptide comprising VH CDR1 consisting of a sequence of SEQ ID NO: 7, VH CDR2 consisting of a sequence of SEQ ID NO: 8, and VH CDR3 consisting of a sequence of SEQ ID NO: 9

(iii) a polypeptide comprising VH CDR1 consisting of a sequence of SEQ ID NO: 10, VH CDR2 consisting of a sequence of SEQ ID NO: 11, and VH CDR3 consisting of a sequence of SEQ ID NO: 12

(iv) a polypeptide comprising VL CDR1 consisting of a sequence of SEQ ID NO: 19, VL CDR2 consisting of a sequence of SEQ ID NO: 20, and VL CDR3 consisting of a sequence of SEQ ID NO: 21

(v) a polypeptide comprising VL CDR1 consisting of a sequence of SEQ ID NO: 22, VL CDR2 consisting of a sequence of SEQ ID NO: 23, and VL CDR3 consisting of a sequence of SEQ ID NO: 24

(vi) a polypeptide comprising VL CDR1 consisting of a sequence of SEQ ID NO: 25, VL CDR2 consisting of a sequence of SEQ ID NO: 26, and VL CDR3 consisting of a sequence of SEQ ID NO: 27.

In one embodiment, the present invention provides a polypeptide comprising VH CDR1, VH CDR2, and VH CDR3 consisting of each amino acid sequence described in FIGS. 2A-2E. In the embodiment, the present invention provides a polypeptide comprising VL CDR1, VL CDR2, and VL CDR3 consisting of each amino acid sequence described in FIGS. 2A-2E. More preferable is (vii) a polypeptide comprising VH CDR1 consisting of a sequence of SEQ ID NO: 7, VH CDR2 consisting of a sequence of SEQ ID NO: 8, and VH CDR3 consisting of a sequence of SEQ ID NO: 94, or (viiiviii) a polypeptide comprising VH CDR1 consisting of a sequence of SEQ ID NO: 7, VH CDR2 consisting of a sequence of SEQ ID NO: 97, and VH CDR3 consisting of a sequence of SEQ ID NO: 9.

In another aspect, the present invention provides a polypeptide comprising the variable region described in any of the followings. More preferable is a polypeptide of (i), (ii), (iv) or (v).

(i) a heavy chain variable region (VH) comprising CDR1 consisting of a sequence of SEQ ID NO: 4, CDR2 consisting of a sequence of SEQ ID NO: 5, CDR3 consisting of a sequence of SEQ ID NO: 6

(ii) a VH comprising CDR1 consisting of a sequence of SEQ ID NO: 7, CDR2 consisting of a sequence of SEQ ID NO: 8, CDR3 consisting of a sequence of SEQ ID NO: 9

(iii) a VH comprising CDR1 consisting of a sequence of SEQ ID NO: 10, CDR2 consisting of a sequence of SEQ ID NO: 11, CDR3 consisting of a sequence of SEQ ID NO: 12

(iv) a light chain variable region (VL) comprising CDR1 consisting of a sequence of SEQ ID NO: 19, CDR2 consisting of a sequence of SEQ ID NO: 20, CDR3 consisting of a sequence of SEQ ID NO: 21

(v) a VL comprising CDR1 consisting of a sequence of SEQ ID NO: 22, CDR2 consisting of a sequence of SEQ ID NO: 23, CDR3 consisting of a sequence of SEQ ID NO: 24

(vi) a VL comprising CDR1 consisting of a sequence of SEQ ID NO: 25, CDR2 consisting of a sequence of SEQ ID NO: 26, CDR3 consisting of a sequence of SEQ ID NO: 27.

In one embodiment, the present invention provides a polypeptide comprising a VH comprising VH CDR1, VH CDR2, and VH CDR3 consisting of each amino acid sequence described in FIGS. 2A-2E. In the embodiment, the present invention provides a polypeptide comprising a VL comprising VL CDR1, VL CDR2, and VL CDR3 consisting of each amino acid sequence described in FIGS. 2A-2E.

In one aspect of the present invention, the polypeptide is preferably an antigen binding substance which has a binding activity for presepsin.

The above antibody or polypeptide may have a substitution, a deletion, an addition, and/or an insertion (referred to as a substitution or the like) of one or more amino acids in the CDR sequence. The antibody or polypeptide after substitution or the like of one or more amino acids preferably has the same activity or performance as that before performing substitution or the like, in terms of binding activity for an antigen, characteristics at the time of measuring presepsin, or the like. As described herein, the antibody or polypeptide after substitution or the like, which has the same activity or performance or better as that before performing substitution or the like, includes both a variant obtained by artificial modification based on a known genetic engineering method and a variant occurring naturally (so-called allele variant). A multiple number of the amino acid substitutions is not particularly limited and substitution may include 1 or higher. However, it is preferably three or less amino acids, more preferably two or less amino acid, and even more preferably one amino acid in one CDR. In one embodiment, an antibody or a polypeptide of the present invention may have a CDR amino acid sequence with 90% identity or higher to the amino acid sequence of CDR designated by SEQ ID NO. as described above. The sequence identity may be 92% or higher, 95% or higher, 97% or higher, or 99% or higher. Such the antibody or polypeptide preferably has the same level of activity or performance as the antibody or polypeptide designated by SEQ ID NO.

In another aspect, the present invention provides for an anti-presepsin antibody or an antigen-binding antibody fragment thereof, wherein the antibody or the antigen-binding antibody fragment specifically recognizes an epitope consisting of an amino acid sequence of Sequence ID No. 1, and wherein the antibody or the antigen-binding antibody fragment comprises, VH and VL regions. In some embodiments, VH CDR1 may consist of the sequence $X_1X_2X_3MX4$; VH CDR2 may consist of the sequence $IX_5X_6X_7X_8YAX_9X_{10}X_{11}X_{12}X_{13}$; and VH CDR3 may consist of the sequence $X_{14}X_{15}X_{16}$; while VL CDR1 may consist of the sequence $X_{17}X_{18}X_{19}X_{20}X_{21}X_{22}X_{23}X_{24}$; VL CDR2 may consist of the sequence $KX_{25}X_{26}X_{27}X_{28}X_{29}S$; and VL CDR3 may consist of the sequence $X_{30}X_{31}X_{32}YX_{33}X_{34}X_{35}X_{36}X_{37}$, wherein $X_1$ through $X_{37}$ are defined in Table 1 to Table 6.

TABLE 1

| | VH CDR1 | | | | |
|---|---|---|---|---|---|
| Basic sequence | X1 | X2 | X3 | M | X4 |
| Option | R, S, A, M, P, V, I, D, E, H, T, Q, Y, G, K, N, W, L, F or C | Y or F | T, A or W | | G or S |

TABLE 2

| | | | | | | | | | | | |
|---|---|---|---|---|---|---|---|---|---|---|---|
| | | | VH CDR2 | | | | | | | | |
| Basic sequence | I | X5 | X6 | X7 | X8 | Y | A | X9 | X10 | X11 | X12 | X13 |
| Option | I or V | I or V | NSGA (SEQ ID NO: 157), YRNIK (SEQ ID NO: 158), ANSGA (SEQ ID NO: 159), SSDGG (SEQ ID NO: 160), SDIDQ (SEQ ID NO: 161), or SDIDD (SEQ ID NO: 162) | T, I or L | Y, V or F | | | S or T | W or A | A or G | K or A | G or A |

TABLE 3

| | VH CDR3 | | |
|---|---|---|---|
| Basic sequence | X14 | X15 | X16 |
| Option | G, A, L or S | D, F, S, P, H, I, N, R, V, G or L | F, A, S, P, H, D, I, N, R, L, E or H |

TABLE 4

| | VL CDR1 | | | | | | | |
|---|---|---|---|---|---|---|---|---|
| Basic sequence | X17 | X18 | X19 | X20 | X21 | X22 | X23 | X24 |
| Option | Q or A | A or G | S or A | QS, ED, or QN | I or A | GSN (SEQ ID NO: 182), ISN (SEQ ID NO: 183), | L or A | A or S |

TABLE 4-continued

| | VL CDR1 | | | | | | | |
|---|---|---|---|---|---|---|---|---|
| Basic sequence | X17 | X18 | X19 | X20 | X21 | X22 | X23 | X24 |
| | | | | | | GSD (SEQ ID NO: 184), or SNY (SEQ ID NO: 185), | | |

TABLE 5

| | VL CDR2 | | | | | | |
|---|---|---|---|---|---|---|---|
| Basic sequence | K | X25 | X26 | X27 | X28 | X29 | S |
| Option | | A or T | S or A | K or T | L or A | A or E | |

TABLE 6

| | VL CDR3 | | | | | | | | |
|---|---|---|---|---|---|---|---|---|---|
| Basic sequence | X30 | X31 | X32 | Y | X33 | X34 | X35 | X36 | X37 |
| Option | Q or A | C or S | S or T | | T or Y | AIGNY (SEQ ID NO: 163), ESTTF (SEQ ID NO: 164), AIGNAY (SEQ ID NO: 165) or RSTTTY (SEQ ID NO: 166) | G or A | H or N | V, A or T |

In another aspect, the antibody or the antigen-binding antibody fragment of the present invention may comprise VH CDR1, VH CDR2 and VH CDR3, and VL CDR1, VL CDR2, and VL CDR3, wherein VH CDR1, VH CDR2 and VH CDR3 are selected from Table 7 and VL CDR1, VL CDR2, and VL CDR3 are selected from Table 8.

TABLE 7

| | | $V_H$ | | | |
|---|---|---|---|---|---|
| CDR1 | SEQ ID NO: | CDR2 | SEQ ID NO: | CDR3 | SEQ ID NO: |
| RYAMG | 95 | IIANSGATYYASWAKG | 97 | GDF | 170 |
| RYTMG | 167 | IINSGATYYASAAKG | 104 | GGL | 171 |
| SFWMS | 168 | IINSGATYYASWAAG | 105 | ADF | 93 |
| SYTMG | 96 | IINSGATYYASWAKA | 106 | GDA | 94 |
| AYTMG | 98 | IINSGATYYASWGKG | 107 | LDF | 124 |
| MYTMG | 126 | IIYRNIKTYYATWAKG | 109 | SDF | 125 |
| PYTMG | 127 | IINSGATYYASWAKG | 169 | GFF | 140 |

TABLE 7-continued

| | | $V_H$ | | | |
|---|---|---|---|---|---|
| CDR1 | SEQ ID NO: | CDR2 | SEQ ID NO: | CDR3 | SEQ ID NO: |
| VYTMG | 128 | IVSSDGGIYYASWAKG | 108 | GSF | 141 |
| IYTMG | 129 | IISDIDQIVYATWAKG | 110 | GPF | 142 |
| DYTMG | 130 | IISDIDDLFYASWAKG | 111 | GHF | 143 |
| EYTMG | 131 | | | GIF | 144 |
| HYTMG | 132 | | | GNF | 145 |
| TYTMG | 133 | | | GRF | 146 |
| QYTMG | 134 | | | GDS | 147 |
| YYTMG | 135 | | | GDP | 148 |
| GYTMG | 136 | | | GDH | 149 |
| KYTMG | 137 | | | GDD | 150 |
| NYTMG | 138 | | | GDI | 151 |
| WYTMG | 139 | | | GDN | 152 |
| | | | | GDR | 153 |
| | | | | GVL | 154 |
| | | | | GGE | 155 |
| | | | | GLH | 156 |

TABLE 8

| | | $V_L$ | | | |
|---|---|---|---|---|---|
| CDR1 | SEQ ID NO: | CDR2 | SEQ ID NO: | CDR3 | SEQ ID NO: |
| QASEDIISNLA | 122 | KASTLAS | 121 | QSSYTESTTFGHV | 101 |
| QASQSIGSNLA | 172 | KASKLAS | 173 | QCSYTAIGNYGHV | 174 |
| QASQSAGSNLA | 100 | KTSTLES | 102 | QCSYTAIGNAYGHV | 99 |
| QASQSISNYLA | 103 | KASKAAS | 117 | QCSYTAIGNYGHA | 112 |
| QAAQSIGSNLA | 114 | KAAKLAS | 118 | QCSYTAIGNYAHV | 113 |
| QGSQSIGSNLA | 115 | | | ACSYTAIGNYGHV | 116 |
| QASQSIGSNAA | 119 | | | QSTYYRSTTTYGNT | 175 |
| AASQSIGSNLA | 120 | | | | |
| QASQNIGSDLS | 123 | | | | |

In yet another aspect, the antibody or the antigen-binding antibody fragment of the present invention may be chosen from the antibodies listed in Table 9.

TABLE 9

| Antibody | V_H CDR1 | SEQ ID NO: | CDR2 | SEQ ID NO: | CDR3 | SEQ ID NO: | V_L CDR1 | SEQ ID NO: | CDR2 | SEQ ID NO: | CDR3 | SEQ ID NO: |
|---|---|---|---|---|---|---|---|---|---|---|---|---|
| 5810 | RYTMG | 167 | IIANSGATYYASWAKG | 97 | GDF | 169 | QASQSIGSNLA | 170 | KASKLAS | 172 | QCSYTAIGNYGHV | 174 |
| 5844 | RYTMG | 167 | IINSGATYYASWAKG | 167 | GDF | 169 | QASQSIGSNLA | 170 | KASKLAS | 172 | QCSYTAIGNAYGHV | 99 |
| 5858 | RYTMG | 167 | IINSGATYYASWAKG | 167 | GDF | 169 | QASQSAGSNLA | 100 | KASKLAS | 172 | QCSYTAIGNYGHV | 174 |
| 5875 | RYTMG | 167 | IINSGATYYASWAKG | 167 | GDF | 169 | QASQSIGSNLA | 170 | KTSTLES | 102 | QCSYTAIGNYGHV | 174 |
| 5878 | RYTMG | 167 | IINSGATYYASWAKG | 167 | GDF | 169 | QASQSISNYLA | 103 | KASKLAS | 172 | QCSYTAIGNYGHV | 174 |
| 5807 | RYTMG | 167 | IINSGATYYASAAKG | 104 | GDF | 169 | QASQSIGSNLA | 170 | KASKLAS | 172 | QCSYTAIGNYGHV | 174 |
| 5808 | RYTMG | 167 | IINSGATYYASWAAG | 105 | GDF | 169 | QASQSIGSNLA | 170 | KASKLAS | 172 | QCSYTAIGNYGHV | 174 |
| 5809 | RYTMG | 167 | IINSGATYYASWAKA | 106 | GDF | 169 | QASQSIGSNLA | 170 | KASKLAS | 172 | QCSYTAIGNYGHV | 174 |
| 5812 | RYTMG | 167 | IINSGATYYASWGKG | 107 | GDF | 169 | QASQSIGSNLA | 170 | KASKLAS | 172 | QCSYTAIGNYGHA | 112 |
| 5842 | RYTMG | 167 | IINSGATYYASWAKG | 167 | GDF | 169 | QAAQSIGSNLA | 114 | KASKLAS | 172 | QCSYTAIGNYGHV | 113 |
| 5843 | RYTMG | 167 | IINSGATYYASWAKG | 167 | GDF | 169 | QGSQSIGSNLA | 115 | KASKLAS | 172 | QCSYTAIGNYGHV | 174 |
| 5859 | RYTMG | 167 | IINSGATYYASWAKG | 167 | GDF | 169 | QASQSIGSNLA | 170 | KASKLAS | 172 | ACSYTAIGNYGHV | 116 |
| 5860 | RYTMG | 167 | IINSGATYYASWAKG | 167 | GDF | 169 | QASQSIGSNLA | 170 | KASKAAS | 117 | QCSYTAIGNYGHV | 174 |
| 5861 | RYTMG | 167 | IINSGATYYASWAKG | 167 | GDF | 169 | QASQSIGSNLA | 170 | KAAKLAS | 118 | QCSYTAIGNYGHV | 174 |
| 5862 | RYTMG | 167 | IINSGATYYASWAKG | 167 | GDF | 169 | QASQSIGSNLA | 170 | KASKLAS | 172 | QCSYTAIGNYGHV | 174 |
| 5863 | RYTMG | 167 | IINSGATYYASWAKG | 167 | GDF | 169 | QASQSIGSNAA | 119 | KASKLAS | 172 | QCSYTAIGNYGHV | 174 |
| 5864 | RYTMG | 167 | IINSGATYYASWAKG | 167 | GDF | 169 | AASQSIGSNLA | 120 | KASKLAS | 172 | QCSYTAIGNYGHV | 174 |
| 5865 | RYTMG | 167 | IINSGATYYASWAKG | 167 | ADF | 93 | QASQSIGSNLA | 170 | KASKLAS | 172 | QCSYTAIGNYGHV | 174 |
| 5784 | RYTMG | 167 | IINSGATYYASWAKG | 167 | GDA | 94 | QASQSIGSNLA | 170 | KASKLAS | 172 | QCSYTAIGNYGHV | 174 |
| 5793 | RYAMG | 95 | IINSGATYYASWAKG | 167 | GDF | 169 | QASQSIGSNLA | 170 | KASKLAS | 172 | QCSYTAIGNYGHV | 174 |
| 5795 | SYTMG | 96 | IINSGATYYASWAKG | 167 | GDF | 169 | QASQSIGSNLA | 170 | KASKLAS | 172 | QCSYTAIGNYGHV | 174 |
| 5803 | RYTMG | 167 | IINSGATYYASWAKG | 167 | GDF | 169 | QASQSIGSNLA | 170 | KASKLAS | 172 | QCSYTAIGNYGHV | 174 |
| 5826 | RYTMG | 167 | IIYRNIKTYYATWAKG | 167 | GDF | 169 | QASQSIGSNLA | 170 | KASKLAS | 172 | QCSYTAIGNYGHV | 174 |

TABLE 9-continued

| Antibody | V_H | | | | | | | V_L | | | | | |
|---|---|---|---|---|---|---|---|---|---|---|---|---|---|
| | CDR1 | SEQ ID NO: | CDR2 | SEQ ID NO: | CDR3 | SEQ ID NO: | CDR1 | SEQ ID NO: | CDR2 | SEQ ID NO: | CDR3 | SEQ ID NO: |
| 5811 | AYTMG | 98 | IINSGATYYASWAKG | 169 | GDF | 170 | QASQSIGSNLA | 172 | KASKLAS | 173 | QCSYTAIGNYGHV | 174 |
| 5874 | RYTMG | 167 | IINSGATYYASWAKG | 169 | GDF | 170 | QASQSIGSNLA | 172 | KASKLAS | 173 | QSSYTESTFGHV | 101 |
| 5684 | RYTMG | 167 | IINSGATYYASWAKG | 169 | GDF | 170 | QASEDIISNLA | 172 | KASTLAS | 121 | QSSYTESTTFGHV | 101 |
| 5877 | RYTMG | 167 | IINSGATYYASWAKG | 169 | GDF | 170 | QASEDIISNLA | 172 | KASTLAS | 122 | QCSYTAIGNYGHV | 174 |
| 5884 | RYTMG | 167 | IINSGATYYASWAKG | 169 | GDF | 170 | QASQSIGSNLA | 172 | KASKLAS | 173 | QCSYTAIGNYGHV | 174 |
| 5920 | RYTMG | 167 | IINSGATYYASWAKG | 169 | LDF | 124 | QASQSIGSNLA | 172 | KASKLAS | 173 | QCSYTAIGNYGHV | 174 |
| 5926 | MYTMG | 126 | IINSGATYYASWAKG | 169 | SDF | 125 | QASQSIGSNLA | 172 | KASKLAS | 173 | QCSYTAIGNYGHV | 174 |
| 5932 | PYTMG | 127 | IINSGATYYASWAKG | 169 | GDF | 170 | QASQSIGSNLA | 172 | KASKLAS | 173 | QCSYTAIGNYGHV | 174 |
| 5933 | VYTMG | 128 | IINSGATYYASWAKG | 169 | GDF | 170 | QASQSIGSNLA | 172 | KASKLAS | 173 | QCSYTAIGNYGHV | 174 |
| 5934 | IYTMG | 129 | IINSGATYYASWAKG | 169 | GDF | 170 | QASQSIGSNLA | 172 | KASKLAS | 173 | QCSYTAIGNYGHV | 174 |
| 5935 | DYTMG | 130 | IINSGATYYASWAKG | 169 | GDF | 170 | QASQSIGSNLA | 172 | KASKLAS | 173 | QCSYTAIGNYGHV | 174 |
| 5937 | EYTMG | 131 | IINSGATYYASWAKG | 169 | GDF | 170 | QASQSIGSNLA | 172 | KASKLAS | 173 | QCSYTAIGNYGHV | 174 |
| 5938 | HYTMG | 132 | IINSGATYYASWAKG | 169 | GDF | 170 | QASQSIGSNLA | 172 | KASKLAS | 173 | QCSYTAIGNYGHV | 174 |
| 5939 | TYTMG | 133 | IINSGATYYASWAKG | 169 | GDF | 170 | QASQSIGSNLA | 172 | KASKLAS | 173 | QCSYTAIGNYGHV | 174 |
| 5940 | QYTMG | 134 | IINSGATYYASWAKG | 169 | GDF | 170 | QASQSIGSNLA | 172 | KASKLAS | 173 | QCSYTAIGNYGHV | 174 |
| 5941 | YYTMG | 135 | IINSGATYYASWAKG | 169 | GDF | 170 | QASQSIGSNLA | 172 | KASKLAS | 173 | QCSYTAIGNYGHV | 174 |
| 5942 | GYTMG | 136 | IINSGATYYASWAKG | 169 | GDF | 170 | QASQSIGSNLA | 172 | KASKLAS | 173 | QCSYTAIGNYGHV | 174 |
| 5943 | KYTMG | 137 | IINSGATYYASWAKG | 169 | GDF | 170 | QASQSIGSNLA | 172 | KASKLAS | 173 | QCSYTAIGNYGHV | 174 |
| 5944 | NYTMG | 138 | IINSGATYYASWAKG | 169 | GDF | 170 | QASQSIGSNLA | 172 | KASKLAS | 173 | QCSYTAIGNYGHV | 174 |
| 5945 | WYTMG | 139 | IINSGATYYASWAKG | 169 | GDF | 170 | QASQSIGSNLA | 172 | KASKLAS | 173 | QCSYTAIGNYGHV | 174 |
| 5946 | RYTMG | 167 | IINSGATYYASWAKG | 169 | GFF | 140 | QASQSIGSNLA | 172 | KASKLAS | 173 | QCSYTAIGNYGHV | 174 |
| 5976 | RYTMG | 167 | IINSGATYYASWAKG | 169 | GSF | 141 | QASQSIGSNLA | 172 | KASKLAS | 173 | QCSYTAIGNYGHV | 174 |
| 5977 | RYTMG | 167 | IINSGATYYASWAKG | 169 | GPF | 142 | QASQSIGSNLA | 172 | KASKLAS | 173 | QCSYTAIGNYGHV | 174 |
| 5978 | RYTMG | 167 | IINSGATYYASWAKG | 169 | GPF | 142 | QASQSIGSNLA | 172 | KASKLAS | 173 | QCSYTAIGNYGHV | 174 |

TABLE 9-continued

| Antibody | VH CDR1 | SEQ ID NO: | CDR2 | SEQ ID NO: | CDR3 | SEQ ID NO: | VL CDR1 | SEQ ID NO: | CDR2 | SEQ ID NO: | CDR3 | SEQ ID NO: |
|---|---|---|---|---|---|---|---|---|---|---|---|---|
| 5979 | RYTMG | 167 | IINSGATYYASWAKG | 169 | GHF | 143 | QASQSIGSNLA | 172 | KASKLAS | 173 | QCSYTAIGNYGHV | 174 |
| 5980 | RYTMG | 167 | IINSGATYYASWAKG | 169 | GIF | 144 | QASQSIGSNLA | 172 | KASKLAS | 173 | QCSYTAIGNYGHV | 174 |
| 5981 | RYTMG | 167 | IINSGATYYASWAKG | 169 | GNF | 145 | QASQSIGSNLA | 172 | KASKLAS | 173 | QCSYTAIGNYGHV | 174 |
| 5982 | RYTMG | 167 | IINSGATYYASWAKG | 169 | GRF | 146 | QASQSIGSNLA | 172 | KASKLAS | 173 | QCSYTAIGNYGHV | 174 |
| 5983 | RYTMG | 167 | IINSGATYYASWAKG | 169 | GDS | 147 | QASQSIGSNLA | 172 | KASKLAS | 173 | QCSYTAIGNYGHV | 174 |
| 5984 | RYTMG | 167 | IINSGATYYASWAKG | 169 | GDP | 148 | QASQSIGSNLA | 172 | KASKLAS | 173 | QCSYTAIGNYGHV | 174 |
| 5985 | RYTMG | 167 | IINSGATYYASWAKG | 169 | GDH | 149 | QASQSIGSNLA | 172 | KASKLAS | 173 | QCSYTAIGNYGHV | 174 |
| 5986 | RYTMG | 167 | IINSGATYYASWAKG | 169 | GDD | 150 | QASQSIGSNLA | 172 | KASKLAS | 173 | QCSYTAIGNYGHV | 174 |
| 5987 | RYTMG | 167 | IINSGATYYASWAKG | 169 | GDI | 151 | QASQSIGSNLA | 172 | KASKLAS | 173 | QCSYTAIGNYGHV | 174 |
| 5988 | RYTMG | 167 | IINSGATYYASWAKG | 169 | GDN | 152 | QASQSIGSNLA | 172 | KASKLAS | 173 | QCSYTAIGNYGHV | 174 |
| 5989 | RYTMG | 167 | IINSGATYYASWAKG | 169 | GDR | 153 | QASQSIGSNLA | 172 | KASKLAS | 173 | QCSYTAIGNYGHV | 174 |
| 6026 | RYTMG | 167 | IINSGATYYASWAKG | 169 | GVL | 154 | QASQSIGSNLA | 172 | KASKLAS | 173 | QCSYTAIGNYGHV | 174 |
| 6028 | RYTMG | 167 | IINSGATYYASWAKG | 169 | GGE | 155 | QASQSIGSNLA | 172 | KASKLAS | 173 | QCSYTAIGNYGHV | 174 |
| 6029 | RYTMG | 167 | IINSGATYYASWAKG | 169 | GLH | 156 | QASQSIGSNLA | 172 | KASKLAS | 173 | QCSYTAIGNYGHV | 174 |
| 5824 | RYTMG | 167 | IVSSDGGIYYASWAKG | 108 | GDF | 170 | QASQSIGSNLA | 172 | KASKLAS | 173 | QCSYTAIGNYGHV | 174 |
| 5827 | RYTMG | 167 | IISDIDQIVYATWAKG | 110 | GDF | 170 | QASQSIGSNLA | 172 | KASKLAS | 173 | QCSYTAIGNYGHV | 174 |
| 5841 | RYTMG | 167 | IISDIDDLFYASWAKG | 111 | GDF | 170 | QASQSIGSNLA | 172 | KASKLAS | 173 | QCSYTAIGNYGHV | 174 |
| 5910 | RYTMG | 167 | IINSGATYYASWAKG | 169 | GDF | 170 | QASQNIGSDLS | 123 | KASKLAS | 173 | QCSYTAIGNYGHV | 174 |
| F1466-5 | RYAMG | 95 | IIYRNIKTYYATWAKG | 109 | GDF | 170 | QASEDIISNLA | 122 | KASTLAS | 121 | QSSYTESTTFGHV | 101 |
| F1466-26 | RYTMG | 167 | IINSGATYYASWAKG | 169 | GDF | 170 | QASQSIGSNLA | 172 | KASKLAS | 173 | QCSYTAIGNYGHV | 174 |
| F1466-16 | SFWMS | 168 | IISDIDDLFYASWAKG | 111 | GGL | 171 | QASQSISNVLA | 103 | KITSTLES | 102 | QSTYYRSTTTYGNT | 175 |

The framework region (FR) of the antibody to be conjugated to CDR is selected such that the CDRs form a good antigen binding site. The FR used for the variable region of the present invention is not particularly limited, and any FR can be used. If necessary, one or more amino acids of FR may be substituted, deleted, added, and/or inserted so that CDR can form an appropriate antigen binding site. For example, according to measurement and evaluation of the binding activity of an antibody using FR with substituted amino acid for an antigen, a variant FR sequence having a desired property may be also selected. In one embodiment, FR may be an amino acid sequence which has identity of 80% or higher to the sequence designated by SEQ ID NO. The sequence identity may be 85% or higher, 90% or higher, 95% or higher, 97% or higher, or 99% or higher.

For example, well-known FR amino acid sequences that can be obtained from a database (GenBank) and may be used as the framework region. (e.g.AAO06511.1, AAT02391.1, AAG13973.1 and AGT29816.1 are exemplified as amino acid sequence. AY596429.1, AY171772.1, KC020056.1 and AF294966.1 are exemplified as polynucleotide sequence.) SEQ ID NOs.: 48 to 84 are suitable for use in certain embodiments of the present invention. Framework regions may be derived from various animals, although rabbit is preferably used in some embodiments the present invention. Preferred FR regions of the antibodies of the present invention include those shown in SEQ ID NOs.: 64-84, or more preferrably SEQ ID NOs.: 65, 66, 68, 69, 71, 72, 73, 75, 76, 78, 79, 81, 82, 83, or 84.

In one embodiment, preferable examples of the variable regions of the antibody of the present invention are as follows:

(1) a VH comprising VH CDRs of the variant described in FIGS. 2A-2E (e.g. the amino acid sequence of VH CDR1, VH CDR2 and VH CDR3 of the antibody5810) and FR of the sequence of SEQ ID NO: 64, SEQ ID NO: 67, SEQ ID NO: 70, and SEQ ID NO: 73; and a VL comprising VL CDRs of the variant described in FIGS. 2A-2E (e.g. the amino acid sequence of VL CDR1, VL CDR2 and VL CDR3 of the antibody5810) and FR of the sequence of SEQ ID NO: 74, SEQ ID NO: 77, SEQ ID NO: 80, and SEQ ID NO: 84.

(2) a VH comprising VH CDRs of F1466-5, F1466-26 or F1466-16 (e.g. the amino acid sequence of VH CDR1, VH CDR2 and VH CDR3 of F1466-26) and FR of the sequence of SEQ ID NO: 64, SEQ ID NO: 67, SEQ ID NO: 70, and SEQ ID NO: 73; and a VL comprising VL CDRs of F1466-5, F1466-26 or F1466-16 (e.g. the amino acid sequence of VL CDR1, VL CDR2 and VL CDR3 of F1466-26) and FR of the sequence of SEQ ID NO: 74, SEQ ID NO: 77, SEQ ID NO: 80, and SEQ ID NO: 84.

(3) a VH comprising VH CDRs of the variant described in FIGS. 2A-2E (e.g. the amino acid sequence of VH CDR1, VH CDR2 and VH CDR3 of the antibody5810) and FR of the sequence of SEQ ID NO: 65 (or 66), SEQ ID NO: 68 (or 69), SEQ ID NO: 71 (or 72), and SEQ ID NO: 73; and a VL comprising VL CDRs of the variant described in FIGS. 2A-2E (e.g. the amino acid sequence of VL CDR1, VL CDR2 and VL CDR3 of the antibody5810) and FR of the sequence of SEQ ID NO: 75 (or 76), SEQ ID NO: 78 (or 79), SEQ ID NO: 81 (or 82 or 83), and SEQ ID NO: 84.

(4) a VH comprising VH CDRs of F1466-5, F1466-26 or F1466-16 (e.g. the amino acid sequence of VH CDR1, VH CDR2 and VH CDR3 of F1466-26) and FR of the sequence of SEQ ID NO: 65 (or 66), SEQ ID NO: 68 (or 69), SEQ ID NO: 71 (or 72), and SEQ ID NO: 73; and a VL comprising VL CDRs of F1466-5, F1466-26 or F1466-16 (e.g. the amino acid sequence of VL CDR1, VL CDR2 and VL CDR3 of the antibody5810) and FR of the sequence of SEQ ID NO: 75 (or 76), SEQ ID NO: 78 (or 79), SEQ ID NO: 81 (or 82 or 83), and SEQ ID NO: 84.

In the variable region, one or more amino acids (for example, five or less amino acids, and preferably three or less amino acids) may be substituted, deleted, added, and/or inserted. The antibody or polypeptide after substitution or the like of one or more amino acids preferably has the same activity or performance as that before performing substitution or the like, in terms of binding activity for an antigen, characteristics at the time of measuring presepsin, or the like. In one embodiment, when a variable region is specified by the sequence as described above, the variable region may have an amino acid sequence with 80% identity or higher to the sequence designated by the amino acid sequence as shown SEQ ID NO. The sequence identity may be 85% or higher, 90% or higher, 95% or higher, 97% or higher, or 99% or higher. Such the variable region preferably has the same level of activity or performance as the variable region designated by the amino acid sequence as shown SEQ ID NO.

The constant region used for an antibody of the present invention is not particularly limited, and any constant region can be used. Preferred examples of the constant region that is used for the antibody of the present invention include a constant region of IgG derived from a mouse, a rat, a rabbit, or a human. The constant region may have one or more amino acids that are substituted, deleted, added, and/or inserted within a range in which the binding activity for an antigen, characteristics at the time of measuring presepsin, and the like are not affected by them.

The antibody of the present invention is preferably a monoclonal antibody, that is, an anti-presepsin monoclonal antibody. The monoclonal antibody is an antibody secreted from an antibody-producing cell of a monoclone. Compared to a polyclonal antibody, the monoclonal antibody has a characteristic in that an antibody with a high titer and homogenous antigen specificity, or the like may be obtained. Theoretically, the monoclonal antibody has an advantage that it has lower antibody weight required for an antigen measurement compared to a polyclonal antibody. As described herein, the term "antibody" may be used with a meaning of "antibody or an antigen binding antibody fragment thereof."

In one aspect, a monoclonal antibody of the present invention may be preferably produced by using S68 peptide, described by SEQ ID NO: 2, as an antigen for administration.

A monoclonal antibody of the present invention can be obtained by, for example, immunizing an animal with S68 peptide, producing a hybridoma using antibody-producing cells of an immunized animal and myeloma cells, selecting and culturing the hybridoma prepared as a single cell, and purifying a culture supernatant.

The animal species from which the antibody is derived is not particularly limited, and examples thereof include a mouse, a rat, a hamster, and a rabbit. It is preferably a rabbit. In other words, an antibody of the present invention may be an anti-presepsin monoclonal antibody derived from a rabbit (also referred to as a rabbit anti-presepsin monoclonal antibody).

As myeloma cells, various known cells can be used. Examples thereof include SKO-007 derived from a human, SHM-D33 of human-mouse hetero myeloma, P3, NS-1, P3U1, and SP2/0 derived from a mouse, and YB2/0 and Y3-Ag1, 2, 3 derived from a rat. It is also possible to use immortalized B lymphocytes or the like derived from a rabbit.

According to the present invention, it is also preferable that a rabbit-rabbit hybridoma is produced by fusion between rabbit spleen cells and immortalized B lymphocytes or the like derived from a rabbit or a rabbit-mouse hybridoma is produced by fusion with cells derived from immortalized mouse cell line.

The fusion between antibody-producing cells and myeloma cells can be performed by a known method, and examples of an agent for promoting fusion which can be used include polyethylene glycol (PEG) and Sendai virus. With regard to a culture solution used for cell fusion, RPMI1640 culture solution, MEM culture solution, or the like can be used.

The hybridoma formed by fusion is cultured for several days to three weeks or so. Further, by using a selection medium such as a medium containing hypoxanthine, thymidine and aminopterin (HAT medium), for example, fused hybridomas may be separated from non-fused cells. The obtained hybridoma is further selected based on an antibody produced by it. According to preparation of the selected hybridoma as a single clone according to a known limiting dilution, it is established as an antibody-producing hybridoma.

Purification of an antibody can be performed by a known method such as ion exchange chromatography, affinity chromatography (Protein A column, Protein G column, or the like), a salting-out method, alcohol precipitation, isoelectric focusing, electrophoresis, centrifuge, or gel filtration.

An antibody or its antigen binding antibody fragment of the present invention can be also produced by a genetic recombination technique which can be used by a person skilled in the art. For example, based on a sequence of the anti-presepsin antibody obtained, a polynucleotide encoding the antibody or a part of the antibody is prepared and expressed in a suitable host after introduction to an expression vector.

Preparation of the polynucleotide encoding the antibody or a part of the antibody can be performed by, for example, extracting mRNA from a hybridoma producing the antibody of the present invention and synthesizing a cDNA. It can be performed by using a commercially available kit or the like.

Alternatively, an antibody in which a part of a sequence thereof is altered can be also made based on a sequence of an anti-presepsin antibody using the gene recombination technique which can be used by a person skilled in the art. A vector comprising an objective sequence can be prepared, and expressed in a suitable host.

The vector used for the present invention is not particularly limited. However, it is preferably a vector and/or expression vector suitable for expression of the antibody gene. Examples thereof include, but are not limited to, a vector containing EF-1α promoter and/or CMV enhancer.

Examples of the vector which can be used also include, but are not limited to, plasmid derived from *E. coli* (for example, pBR322, pBR325, pUC12, and pUC13), plasmid derived from *Bacillus subtilis* (for example, pUB110, pTP5, and pC194), plasmid derived from yeast (for example, pSH19 and pSH15), bacteriophage such as λ phage, and virus such as retrovirus, vaccinia virus, and baculovirus.

The promoter used in the present invention can be any promoter that is suitable for the host used for gene expression. For example, when the host is an animal cell, a promoter derived from SV40, a promoter of retrovirus, a heat shock promoter, a cytomegalovirus promoter, EF1α promoter, or the like can be used.

If required, the vector may contain an enhancer, a splicing signal, a signal for poly A addition, a selection marker, and an origin for SV40 replication.

Examples of the selection marker which can be used include, but are not limited to, dehydrofolate reductase (dhfr), methotrexate (MTX) resistant gene, and ampicillin resistant gene.

The host cell used for the present invention is not particularly limited. For example, bacterial cells (*E. coli* or the like), yeast, amphibian cells (*Xenopus laevis* oocyte cell or the like), an insect or insect cell (sf9 or the like), an animal cell, and the like are used. Examples of the animal cell which can be used include COS-1 cell, COS-7 cell, CHO cell, DHFR gene depleted CHO cell (dhfr-CHO cell), mouse 3T3 cell, human HEK293 cell, and myeloma cell.

A method for introducing an expression vector to a host cell can be performed by a known method, and examples thereof include, but are not limited to, a lipofection method, a calcium phosphate method, an electroporation method, and a microinjection method.

After introduction of an expression vector to a host cell, cells are cultured in a culture medium suitable for each host cell. For example, in the case of animal cell, a medium for culturing animal cells such as RPMI1640 medium and GIT medium or those media added with various additives such as FCS can be used. By culturing obtained transformed cells in a medium, the antibody can be expressed and accumulated in culture supernatant. For purification of an antibody in culture supernatant, the method described above can be used. Further, the expression amount of an antibody and antigen antibody activity can be measured by ELISA or the like.

An antibody of the present invention or an antigen-binding antibody fragment thereof may be made by a phage display method. Obtaining of an antibody by the phage display method can be carried out by the technique which can be used by a person skilled in the art. (see CARLOS F. BARBAS et al., Phage Display: A Laboratory Manual (Cold Spring Harbor Laboratory Press) etc.) For example, a gene is obtained from splenic lymphocyte obtained by immunizing an animal with the S68 peptide, and is ligated with a phagemid vector or the like, and so on, and thereafter, the conventional method is performed to obtain an antibody.

In addition, in order to make an altered antibody in which only a particular sequence of CDR (e.g. VH CDR3) is changed, it is also possible to use the phage display method. This can be also carried out using the technique which can be used by a person skilled in the art, employing a plasmid comprising a heavy chain and a light chain of an antibody as a template, and particular primers.

Examples of the antigen binding antibody fragment of the present invention include Fab, Fab', F(ab')2, a single strand antibody (scFv), dimerized V region (diabody), disulfide stabilized V region (dsFv), sc(Fv)2, and a polypeptide containing CDR, a polypeptide containing a heavy chain variable region, and a polypeptide containing a light chain variable region. Any of those antibody fragments has an antigen binding property which is the same as the antibody of the present invention for recognizing an epitope consisting of an amino acid sequence of Sequence ID NO: 1.

Those antibody fragments can be prepared by using genetic recombination techniques known to a person skilled in the art.

Fab indicates, among the fragments obtained by treating IgG with protease papain, an antibody fragment having an antigen binding property in which about half of the N terminal side of H chain and the entire L chain are linked via a disulfide bond.

F(ab')2 indicates, among the fragments obtained by treating IgG with protease pepsin, those obtained by linking Fab with a disulfide bond of a hinge region.

Fab' indicates an antibody fragment having an antigen binding activity, which is obtained by digesting the disulfide bond of a hinge region of F(ab')2. Fab' can be obtained by a treatment of F(ab')2 with a reducing reagent, dithiothreitol.

scFv is a polypeptide in which one VH and one VL are linked to each other via a suitable peptide linker, and it is an antibody fragment having an antigen binding activity.

The diabody indicates an antibody fragment having a divalent antigen binding activity as obtained by dimerization of scFv.

dsFv indicates a polypeptide having a substitution of one amino acid residue from each of VH and VL with a cysteine residue, which is linked via a disulfide bond.

sc(Fv)2 indicates an antigen fragment obtained as a single strand based on linking of two VH and two VL via a linker or the like. sc(Fv)2 can be produced by linking scFv via a linker, for example.

In some embodiments, a polypeptide comprising a CDR is the same as those described above, and it is a fragment having an antigen binding activity. A peptide comprising multiple CDRs can be linked directly or via a suitable linker.

The polypeptide comprising a heavy chain variable region and polypeptide comprising a light chain variable region are as described above.

In the present invention, any peptide linker introducible by genetic engineering can be used as a linker. The linker preferred in the present invention is a peptide linker. The length of the peptide linker is not particularly limited, and it can be suitably selected depending on the purpose. However, it is generally 1 to 100 amino acids, preferably 3 to 50 amino acids, and more preferably 5 to 20 amino acids. When four antibody variable regions are linked, three linkers are generally needed. The multiple linkers may be the same or different linkers may be used.

In one aspect, an antibody of the present invention includes a chimeric antibody and a humanized antibody.

A chimeric antibody is an antibody molecule produced by combining a part of antibody molecules from two or more different species. The chimeric antibody preferred in the present invention is an antibody having a variable region derived from a rabbit monoclonal antibody and a constant region of other species (for example, human); however, other chimeric combinations known in the art are contemplated herein.

A humanized antibody is an antibody obtained by transplanting CDR from non-human species to a human antibody.

Chimeric antibodies and humanized antibodies can be produced by general methods that are known in the art.

In one aspect, the present invention comprises an antibody in which one or more amino acid residues are added to the amino acid sequence of the present invention. An antibody of the present invention may also comprise a fusion protein in which the antibody is fused to another peptide or polypeptide. Production of a fusion protein can be performed by using a method known to a person skilled in the art. For example, after linking a polynucleotide encoding the antibody of the present invention to a polynucleotide encoding other peptide or polypeptide such that they have an overlapping frame, and introducing it to an expression vector, expression in a host cell can be performed. Other peptides or polypeptides used for binding with the antibody of the present invention are not particularly limited. Examples thereof include, but are not limited to, FLAG, 6× His consisting of six His (histidine) residues (SEQ ID NO: 176), polyhistidine segment, influenza hemagglutinin (HA), T7-tag, HSV-tag, GST (glutathione-S-transferase), immunoglobulin constant region (Fc region), β-galactosidase, and maltose-binding protein.

2. Method for Measuring Presepsin

In a second embodiment of the present invention, this disclosure provides a method for immunological measurement of presepsin by using at least an antibody or its antigen binding antibody fragment of the present invention, and it includes a step of contacting the antibody or its antigen binding antibody fragment of the present invention with a sample containing presepsin. In the present invention, the term "measure" can be interchangeably used with terms like "detect", "quantify", "assay" or the like, and it is used as a meaning which includes quantitative and qualitative determination. Measurement of presepsin is preferably performed in vitro.

Since presepsin is known as a marker used for detection of sepsis, it can be said that the above method is a method for detecting sepsis including a step of contacting the antibody or its antigen binding antibody fragment of the present invention with a sample containing presepsin.

In another aspect, the present invention can be also said to be a method of detecting sepsis, or a method for assisting detection of sepsis, comprising at least 1) a step of measuring the presepsin concentration in a sample from a subject using an antibody of the present invention, and 2) a step of determining whether the presepsin concentration is a high value in comparison with a cut-off value or not. The cut-off value may be 314 to 600 pg/mL, preferably 400 to 580 pg/mL, more preferably 450 to 550 pg/mL, and further preferably about 500 pg/mL.

As used herein, "detection of disease", may be used interchangeably with "assisting detection of disease" or "assisting diagnosis of disease."

In addition, the antibody or the antigen-binding antibody fragment can be used for detection or evaluation of at least one disease including, but not limited to, discrimination between sepsis and systemic inflammatory response syndrome (SIRS), risk assessment of severity of sepsis, prognostic prediction of sepsis (mortality prediction), the assessment of the degree of septic severity, detection of surgical site infections, detection of disseminated intravascular coagulation (DIC), detection of infectious DIC, detection of heart disease, detection of respiratory infections associated with bacterial infection, detection of inflammatory bowel disease (Crohn's disease, ulcerative colitis), detection of febrile neutropenia (FN), detection of hemophagocytic syndrome (HPS) and evaluating the function of phagocyte.

The term "surgical site infections" as used herein means infectious diseases which are caused after surgery, and includes all infections due to surgery and adjunctive therapy needed therefor. The surgical site infections include all diseases diagnosed as surgical site infections in the basis of Guideline for prevention of surgical site infection, 1999 (CDC).

Heart disease includes, but is not limited to, acute coronary syndrome (ACS), acute heart failure, acute decompensated heart failure (ADHF), chronic heart failure, coronary artery disease, angina pectoris, myocardial infarction, ischemic stroke, hemorrhagic stroke and transient cerebral ischemia attack, and the like.

A respiratory infection associated with a bacterial infection can include lower respiratory tract infections or pneumonia. The lower respiratory tract infections include acute lower respiratory tract infections and chronic lower respiratory tract infections. The acute lower respiratory tract infections include acute tracheitis, acute bronchitis and acute bronchiolitis. Most of them are developed by virus infections of the upper respiratory tract that spread to the lower respiratory tract, and in some of these diseases, secondary infection by bacteria then takes place. Antibiotic administration may be adapted if signs of bacterial secondary infection are observed. The chronic lower respiratory tract infection is a pathologic condition in which persistent bacterial infection has been found in the lower respiratory tract having organic disorders caused by bronchiectasis or chronic obstructive pulmonary disease, and it includes persistent infection and acute exacerbation. Diseases causing organic disorders to the lower respiratory tract include bronchiectasis, chronic obstructive pulmonary disease, chronic bronchitis, diffuse panbronchiolitis, obsolete pulmonary tuberculosis, pneumoconiosis, nontuberculous mycobacterial infection, allergic bronchopulmonary aspergillosis, lung fibrosis, and chronic bronchial asthma. In both cases of persistent infection and acute exacerbation, administration of antibiotics is applied. Pneumonia includes community-acquired pneumonia and hospital-acquired pneumonia. Preferably pneumonia is community-acquired pneumonia.

Evaluating the function of the phagocytic cells means (a) measurement of phagocytic activity of neutrophils, granulocytes and/or white blood cells, (b) evaluation of immune function by measuring phagocytic activity of neutrophils, granulocytes and/or white blood cells, (c) quality assessment of implantable cells upon autologous cell transplantation or allogeneic cell transplantation, and (d) detection of diseases related phagocytosis by phagocytic cells. The diseases related to phagocytosis by phagocytic cells includes such as autoimmune diseases, rheumatoid arthritis, mastitis, gout, glomerulonephritis, ulcerative colitis, Mediterranean fever, otitis media, rhinitis, pneumonia, tuberculosis, cystitis, amniotic fluid infection disease, and pyosemia. The sample used in detecting the diseases related to phagocytosis by phagocytic cells is tissue fluid, lymph, synovial fluid, milk, cerebrospinal fluid, pus, saliva, tears, mucus, nasal discharge, sputum, urine, ascites, amniotic fluid, body fluids such as semen, and as well as lavage fluid obtained after washing nasal cavity, bronchus, lung, skin, peritoneal cavity, various organs, joint, bone, and the like.

Examples of the method for immunological measurement of presepsin by using an antibody or its antigen binding antibody fragment of the present invention include enzyme immunoassay (hereinbelow, also described as ELISA or EIA), chemiluminescence enzyme immunoassay (CLEIA), chemiluminescence immunoassay (CLIA), fluorescence antibody test (FAT), fluorescence enzyme immunoassay (FEIA), electro chemiluminescence immunoassay (ECLIA), radioimmunoassay (RIA), immunochromatography, an agglutination method, and a competition method, but not limited thereto. In the present invention, any of a direct method and an indirect method can be used. A sensitization method involving forming and detecting a biotin-avidin (streptoavidin) complex may be also used.

ELISA is one example of an immunoassay using an enzyme labeled antibody, and examples thereof include a direct method and an indirect method. Preferred examples thereof include ELISA (enzyme-linked immunosorbent assay).

Sandwich ELISA is a method in which the measurement is performed by using two or more antibodies with a different antigen recognition site. One antibody is immobilized in advance on a solid phase and by forming an antibody-antigen-antibody complex with an antigen, detection of said antigen, which is positioned between two kinds of antibody, is possible.

The chemiluminescence enzyme immunoassay (CLEIA) is a method in which an antibody immobilized onto magnetic particles or beads is reacted with an antigen in a sample followed by a reaction with an enzyme labeled antibody and washing (B/F separation), an enzyme reaction is performed by adding a chemiluminescent substrate, and luminescence intensity is measured.

For example, it is possible that an antibody conjugated with biotin is reacted with an antigen in a sample in a liquid phase, the antibody is trapped by magnetic particles linked with streptoavidin, enzyme labeled antibody is reacted after washing (B/F separation), and the same treatment as above is performed.

When an alkali phosphatase (ALP) is used as a labeling enzyme, it is preferable to use CDP-Star™, AMPPD®, or CSPD® as a chemiluminescent substrate. When the labeling enzyme is HRP, luminol is preferably used as a chemiluminescent substrate.

It is generally believed that the detection sensitivity is high in the order of chemiluminescence>fluorescence>absorption (color generation), and the measurement method can be selected depending on desired sensitivity.

The chemiluminescence immunoassay (CLIA) is a method in which an antibody immobilized onto magnetic particles or the like is reacted with an antigen in a sample, the antibody labeled with a chemiluminescent substrate is reacted with it followed by washing (B/F separation), and luminescence intensity is measured. As a labeling substance, acridinium or the like is used.

The fluorescent enzyme immunoassay (FEIA) is a method in which an immobilized antibody is reacted with an antigen in a sample followed by reaction with an enzyme labeled antibody and washing (B/F separation), an enzyme reaction is performed by adding a fluorescent substrate, and the fluorescence intensity is measured. As a labeling enzyme, HRP or ALP or the like is used. When the labeling enzyme is HRP, Amplex®Red is used as a florescent substrate. When the labeling enzyme is ALP, 4-MUP (4-Methylumbelliphenyl phosphate), AttoPhos®, and the like are preferably used.

The electro chemiluminescence immunoassay (ECLIA) is a method in which an antibody immobilized onto magnetic particles, an antigen in a sample, and an antibody labeled with an electro chemiluminescent substance are reacted with one another followed by washing (B/F separation), and the luminescence intensity originating from electric energy is measured. As a labeling substance, ruthenium or the like is used. As a labeling substance, Ru(bpy)3 or the like is used. According to oxidation based on charging on an electrode and reducing reaction by tripropylamine (TPA), excitation luminescence is repeated.

The radioimmunoassay (RIA) is a measurement method in which a labeling body of a radioactive isotope is used. For example, by reacting an antigen in a sample and an antibody immobilized on beads or the like and by reacting it with an antibody labeled with a radioisotope (1251 or the like) followed by washing (B/F separation), the radioactivity of 1251 can be measured.

The immunochromatography is an immunological measurement method in which a capillary phenomenon resulting from migration of a test material along with the dissolution of a reagent on a test strip is applied. Specifically, an immunocomplex is formed among three substances, that is, the antigen in a sample, a labeled antibody on a test strip, and a capturing antibody, and color of the labeled product is determined. For labeling of an antibody, gold colloid, an enzyme, a fluorescent substance, or the like is used. When an enzyme labeled antibody is used, color generation is caused by applying an enzyme substrate on a test strip.

The flow through method is a method in which an antigen as a test substance forms, with a solution in a sample, an antibody-antigen-antibody complex on a membrane as an insoluble membrane. At that time, a substance not immobilized on the membrane generally passes through in perpendicular direction from the surface to back surface of the membrane, and it is removed.

The agglutination method is a method in which an antigen in a sample is reacted with an antibody in a reagent and agglutination is observed. Examples thereof include a method in which no solid phase is used, a particle agglutination (PA) method in which artificially prepared particles are used as a solid phase, and a latex agglutination (LA) method in which latex particles are used among PA.

According to the competition method, for example, an antibody is bound to a solid phase and a sample for test and a certain amount of a labeled antigen are reacted simultaneously, and thus an amount of antigen in the sample can be measured from the amount of bound labeled product.

In one aspect, an antibody of the present invention may be used in any of the above disclosed detection methods for use in a method of detecting presepsin in a sample or diagnosing an individual suspected of having sepsis.

The sample used for presepsin measurement is not particularly limited. However, it is preferably an aqueous sample. Examples thereof include body fluid such as blood (whole blood, blood plasma, blood serum, or the like), urine, tissue fluid, lymph fluid, joint fluid, milk, cerebrospinal fluid, pus, saliva, tear fluid, mucous fluid, nasal discharge, sputum, abdominal fluid, used fluid, or semen, washing liquid after washing nasal cavity, bronchial tubes, lung, skin, abdominal cavity, various organs, joint, bone or the like, cell culture supernatant, and column eluent. Those samples can be used for the measurement either directly or after dilution or extraction with various buffers followed by concentration.

Furthermore, in case of using whole blood as a sample, the whole blood sample may be analyzed within 72 hours, within 48 hours, within 24 hours, within 12 hours, within 6 hours, or within 4 hour after the whole blood sample is collected. Collecting whole blood sample may be performed by using EDTA blood collection tube or heparin blood collection tubes. Preferably, the whole blood sample is analyzed within 6 hours after it is collected into EDTA blood collection tubes, or within 4 hours after it is collected into heparin blood collection tube.

3. Kit for Measurement of sCD14-ST

In a third embodiment of the present invention, this disclosure provides a kit for measuring presepsin which has an antibody or its antigen binding antibody fragment of the first embodiment as an essential constitutional element.

The measurement kit of the present invention preferably includes an auxiliary reagent for presepsin measurement.

Examples of the auxiliary reagent include a primary antibody, a secondary antibody, a labeled antibody, a labeling enzyme, a labeling substance such as gold colloid, a chromogenic substrate, a fluorescent substrate (Amplex® Red, AttoPhos®, 4-MUP, or the like), a chemiluminescent substrate (Luminol, CDP-Star™, AMPPD®, CSPD®, or the like), a specific binding substance such as biotin-streptoavidin, an insoluble carrier, a blocking agent, a diluting solution, a washing liquid, and a reference material, but they are not limited thereto.

In one embodiment, the auxiliary reagent may be used in suitable combination depending on the method for measuring presepsin of the second embodiment.

The primary antibody is preferably an antibody which binds to presepsin. More preferably, it is an antibody recognizing an epitope that is different from the antibody of the present invention. Examples thereof include F1106-13-3 antibody and F1031-8-3 antibody that are described in Example 3 of WO 2004/044005.

Any of the antibodies of the present invention and primary antibody may be used as a labeled antibody. When none of the antibody of the present invention and primary antibody is labeled, a labeled secondary antibody may be also used.

Examples of the insoluble carriers include, but are not limited to, magnetic particles, beads, glass, cellulose, nitrocellulose, a porous synthetic polymer, glass fiber, polyacrylamide, nylon, polystyrene, polyvinyl chloride, polypropylene, plastic plate, latex particles, non-woven fabric, filter paper, and so on.

For labeling of an antibody, an enzyme such as peroxidase (HRP), alkali phosphatase (ALP), and β-galactosidase, gold colloid and the like are preferably used, but it is not limited thereto.

When HRP is used, for example, 3,3',5,5'-tetramethyl benzidine (TMB), o-phenylene diamine (OPD), or the like can be mentioned as a chromogenic substrate. When ALP is used, p-nitrophenyl phosphate (pNPP) or the like can be mentioned as a chromogenic substrate. When β-galactosidase is used, o-nitrophenyl-β-D-galactopyranoside (ONPD) or the like is exemplified as a chromogenic substrate.

In one embodiment, the kit may comprise a measurement kit for sandwich ELISA, which may include, for example, the antibody of the present invention and a primary antibody (any antibody may be labeled with an enzyme), a chromogenic substrate, a diluting solution, a reference material, or the like. When none of the antibody of the present invention and primary antibody is labeled, a labeled secondary antibody may be also included.

In one embodiment, the kit may comprise a measurement kit for chemiluminescence enzyme immunoassay (CLEIA) may include, for example, an antibody immobilized onto magnetic particles, an enzyme labeled antibody, a chemiluminescent substrate, a diluting solution, a washing liquid, or the like.

In one embodiment, the kit may comprise a measurement kit for fluorescence enzyme immunoassay (FEIA) may include, for example, an antibody immobilized onto magnetic particles, an enzyme labeled antibody, a fluorescent substrate, a diluting solution, a washing liquid, or the like.

In one embodiment, the kit may comprise a measurement kit for electro chemiluminescence enzyme immunoassay (ECLIA) may include, for example, a biotinylate antibody, an antibody labeled with Ru(bpy)3, magnetic particles coated with streptoavidin, tripropylamine, or the like.

In one embodiment, the kit may comprise a measurement kit based on immunochromatography is a test strip on which a sample addition part, a reagent part, a detection part, and an absorption part are arranged such that a liquid sample added to the addition part for test undergoes migration in the above order.

For example, it is possible to provide an insoluble carrier binding with the primary antibody in the detection part by impregnating the labeled secondary antibody in the reagent part.

As for the test strip, use of a porous carrier or the like is exemplified. Examples of the porous carrier include, but are not limited to, nitrocellulose, cellulose, cellulose derivatives, nylon, nylon fiber, glass fiber, and a porous synthetic polymer. Examples of the absorption part include, but are not limited to, an absorbing polymer such as sponge composed of a water absorbing material, cellulose filter paper, filter paper, and so on.

Since it has been reported that the presepsin blood concentration is characteristically increased in a sepsis patient, a kit for measuring presepsin of the third embodiment of the present invention can be used as a kit for detecting sepsis, or a kit for assisting detection or diagnosis of sepsis. Also a kit for measuring presepsin of the third embodiment of the present invention can be used as a diagnostic agent for sepsis or an adjunctive agent for sepsis diagnosis.

When used for the purpose of detecting sepsis or assisting diagnosis, it is determined that a subject has a possibility of sepsis when the presepsin concentration in a sample of a subject measured using the antibody of the present invention is a value higher than a cut-off value, and this can assist detection or diagnosis. In one aspect, the cut-off value may be 314 to 600 pg/mL, preferably 400 to 580 pg/mL, more preferably 450 to 550 pg/mL, and further preferably about 500 pg/mL.

In addition, a kit for measuring presepsin can be used for detection or evaluation of at least one disease selected from such as, discrimination between sepsis and systemic inflammatory response syndrome (SIRS), risk assessment of severity of sepsis, prognostic prediction of sepsis (mortality prediction), the assessment of the degree of septic severity, detection of surgical site infections, detection of disseminated intravascular coagulation (DIC), detection of infectious DIC, detection of heart disease, detection of respiratory infections associated with bacterial infection, detection of inflammatory bowel disease (Crohn's disease, ulcerative colitis), detection of febrile neutropenia (FN), detection of hemophagocytic syndrome (HPS) and evaluating the function of phagocyte. The kit for measuring presepsin may be a kit for detection or evaluation of at least one disease described above.

4. Polynucleotide Encoding the Antibody or the Antigen Binding Antibody Fragment Thereof Described in the First Embodiment In a fourth embodiment of the present invention, the disclosure provides a polynucleotide or a nucleic acid encoding the antibody or its antigen binding antibody fragment of the first embodiment of the present invention. The polynucleotide includes DNA (genomic DNA, cDNA, synthetic DNA, or the like) and RNA (mRNA or the like). The polynucleotide can be any of a single strand (coding or anti-sense) and a double strand. For example, it is possible that mRNA is extracted from a hybridoma producing the antibody of the present invention by using a commercially available kit and cDNA is synthesized. A target gene may be amplified by PCR method or the like.

In one embodiment, the antibody of the present invention may have identity of at least 80% or higher to the nucleotide sequence which encodes the heavy chain or light chain of the variable region. With regard to the CDR sequence, it may have identity of at least 80% or higher to the nucleotide sequence which encodes the entire CDR of an antibody (VH CDR1 to 3 and VL CDR1 to 3). From the viewpoint of detection sensitivity, it may exhibit the identity of 85% or higher, the identity of 90% or higher, the identity of 95% or higher, the identity of 96% or higher, the identity of 97% or higher, the identity of 98% or higher, or the identity of 99% or higher.

Further, according to a certain embodiment, an antibody encoded by a nucleotide sequence which hybridizes, under stringent conditions, to a complementary sequence of the nucleotide sequence encoding the heavy chain or light chain is also included in the antibody of the present invention.

The hybridization can be performed by a known method or a method based on it, for example, a method described in Molecular Cloning $3^{rd}$ (J. Sambrook et al., Cold Spring Harbor Lab. Press, 2001).

The stringent conditions indicate conditions at which a specific hybrid is formed while a non-specific hybrid is not formed. Typical stringent conditions include, for example, performing hybridization at potassium concentration of about 25 mM to about 50 mM and magnesium concentration of about 1.0 mM to about 5.0 mM. A person skilled in the art can easily select the conditions by modifying the hybridization reaction or salt concentration of a reaction solution for hybridization.

5. Recombinant Vector Containing Polynucleotide Described in the Fourth Embodiment In a fifth embodiment, the present invention provides a vector introduced with a polynucleotide which encodes the amino acid of an antibody or the antibody binding antigen fragment of the present invention. The vector is preferably a vector and/or an expression vector suitable for expression of the antibody gene which is described in the first embodiment. It can be produced by a technique that is employable by a person skilled in the art.

6. Cells Producing the Antibody or the Antibody Binding Antigen Fragment Described in the First Embodiment In a sixth embodiment of the present invention, the disclosure provides cells producing the antibody or its antigen binding antibody fragment of the present invention. Examples of the cells include a hybridoma, a transformant, and genetic recombinant cells introduced with the gene of the antibody of the present invention.

Specific examples of the hybridoma for producing an antibody include a clone described in Example 1.

A transformant can be obtained by introducing a vector introduced with the polynucleotide encoding the amino acid of the above antibody or its antibody binding antigen fragment of the present invention to the host cell described in the first embodiment (for example, COS-1 cells and CHO cells).

The method for producing a hybridoma or a transformant may be the same as those described for the first embodiment.

7. Method for Producing the Antibody or the Antigen Binding Antibody Fragment Using a Transformant In a seventh embodiment of the present invention, the disclosure provides a method of producing an antibody or an antigen binding antibody fragment including a step of culturing a transformant containing a vector introduced with a nucleotide which encodes the antibody or the antigen binding antibody fragment of the first embodiment.

An antibody or the antigen binding antibody fragment of the first embodiment is produced in a culture of the transformant and an antibody or its antigen binding antibody fragment of the first embodiment is collected from the culture. The methods used may be the same as those described in the first embodiment.

8. Method for Screening Anti-Presepsin Antibody

In an eighth embodiment of the present invention, the disclosure provides a method for screening an antibody to obtain an anti-presepsin antibody useful for measurement of presepsin in a sample, in which the method includes at least the following steps;

1) step of constructing a presepsin measurement system using an antibody of a candidate, 2) step of determining an influence of TG concentration in a sample on a presepsin measurement value by using the measurement system In other words, the method is characterized in that a TG interference test is performed with a measurement system which uses an antibody. The method for obtaining a candidate antibody (preferably, anti-presepsin antibody) may be the same as those described in the first embodiment or the seventh embodiment. In some embodiments, the system for measuring presepsin is a measurement system allowing the measurement of presepsin value in a sample, and it is not particularly limited. Examples thereof include, but are not limited to, the measurement system described in the second embodiment, and for example, sandwich ELISA or the like can be used.

With regard to the step of determining the influence of TG concentration in a sample on a measurement value of presepsin, the influence can be determined in view of separation between the two measurement values, that is, based on the comparison between the measurement value of presepsin in a sample without TG and the measurement value of presepsin in the same sample with a certain amount of TG added. For example, when the TG interference test is performed by using multiple samples, and the ratio of a sample which exhibits the separation degree of the measurement value of presepsin at the time of having TG concentration of 20 mg/mL in a sample compared to the measurement value of presepsin at the time of not adding any TG is ±20% or less and more preferably ±10% or less is high, it may be determined that the influence of TG in a sample on the measurement value of presepsin is small, and it can be also determined, as being unlikely to be influenced by TG interference, the antibody is useful for measurement of presepsin.

Alternatively, as another evaluation method, the evaluation can be made by comparing the separation degree after performing TG interference test using a candidate antibody and S68 antibody. As one preferred embodiment, when separation of the measurement value of presepsin at the time of performing a TG interference test by using a candidate antibody is similar to the separation degree of S68 antibody under the same conditions, the antibody can be found as an antibody useful for measuring presepsin in a sample. As an example, for a measurement system in which the TG interference test is performed by using multiple samples and a candidate antibody is used, a difference between the separation degree by having TG concentration of 20 mg/mL in a sample after adding TG and the separation degree of the measurement system using S68 antibody under the same conditions is determined, and if the ratio of a sample exhibiting the difference in separation degree of 20% or less, and preferably 10% or less is high, it can be determined that the antibody is an antibody useful for measuring presepsin in a sample.

The screening method of the present invention may optionally include a step of determining the binding activity between a candidate antibody and S68 peptide or presepsin. Further, the screening method of the present invention may optionally include a step of measuring a sample from a normal person (i.e. a person that is not septic) and a patient having sepsis by using the presepsin measurement system using a candidate antibody and comparing a difference in the measure values. In one embodiment, screening can be performed according to the descriptions of Example 1.

One preferable embodiment of the screening method is a method comprising at least the following steps:

1) a step of obtaining a candidate anti-presepsin antibody using the production process and the like described in the first embodiment of the present invention, and 2) a step of constructing a presepsin measuring system using the candidate antibody, and selecting the antibody having a detection ratio of 50% or more, showing a separation degree of the presepsin measurement value of ±20% or less, when the TG concentration is adjusted to be 20 mg/mL by addition of TG In this method, the TG concentration (herein, 20 mg/mL) in a sample, a separation degree of the presepsin measurement value (herein, ±20%), and a sample ratio can be appropriately changed. Alternatively, step (2) can be also performed by replacing it with other TG interference tests and/or evaluation methods, described in the first embodiment of the present invention.

Another preferable embodiment is a method of screening the antibody of the present invention comprising at least the following steps:

1) a step of obtaining a candidate anti-presepsin antibody, and 2) a step of determining whether the antibody specifically recognizes an amino acid sequence of Sequence ID NO: 1 as an epitope or not In this method, step (2) can be a method of determining an epitope and the like described in the first embodiment of the present invention can be used, without any limitation.

For example, step (2) may further comprise the following step:

a step of selecting the antibody, in which the binding between the antibody and presepsin is competitively-inhibited by 50% or more in a reaction system that an amino acid residue consisting of Sequence ID NO: 1 is subjected to a competitive reaction (preferably, absorbance) so that the binding between said antibody and presepsin is inhibited.

The following step (3) may be optionally added to the method of determining an epitope:

3) a step of selecting the antibody in which completion-inhibition of the binding between said antibody and presepsin due to at least one of amino acid residues consisting of Sequence ID Nos.: 35, 36, 37, 38, 39, 40 and 41 is less than 20%, in a reaction system that an amino acid residue is subjected to a competitive reaction (preferably, absorbance) so that the binding between said antibody and presepsin is inhibited In addition, another preferable embodiment is a method of screening the antibody of the present invention comprising at least the following steps:

1) a step of obtaining a candidate anti-presepsin antibody using the production process and the like described in the first embodiment of the present invention, and 2) a step of selecting said antibody in which a correlation coefficient with the presepsin measurement value in a sample using the S68 antibody exhibits 0.9 or more This method can be carried out according to the descriptions of the first embodiment of the present invention, and Example 5. A correlation coefficient can also be appropriately changed.

In addition, another preferable embodiment is a method of screening the antibody of the present invention comprising at least the following steps:
1) a step of obtaining a candidate anti-presepsin antibody, and
2) a step of selecting an antibody binding with presepsin in affinity (equilibrium dissociation constant, KD value) of less than $10^{-8}$M Alternatively, step (2) may be replaced with the following step:
2) a step of selecting an antibody in which binding activity of the antibody with presepsin is excellent in comparison with binding activity of the S68 antibody with presepsin It is possible to carry out measurement of affinity (equilibrium dissociation constant, KD value) and binding activity according to the description of the first embodiment of the present invention. Binding activity may be evaluated by an absorbance ratio. Preferably, a ratio of absorbance when the antibody of the present invention and presepsin are reacted is 2 or more, when absorbance of the S68 antibody and presepsin is found to be 1.

The method of screening the antibody of the present invention as described above may be carried out by combining respective steps. A preferable combination is, for example, as follows:

A method of screening an anti-presepsin antibody comprising at least the following steps:
1) a step of obtaining a candidate anti-presepsin antibody,
2) a step of selecting the antibody in which the binding between said antibody and presepsin is competitive-inhibited by 50% or more in a reaction system (preferably, absorbance) that an amino acid residue consisting of Sequence ID NO: 1 is subjected to a competitive reaction so that the binding between said antibody and presepsin is inhibited, and
3) a step of selecting an antibody in which binding activity of the antibody with presepsin is excellent in comparison with binding activity of the S68 antibody with presepsin.

9. Method of Treating Sepsis Patient

In a ninth embodiment of the present invention, the disclosure provides a method of treating a sepsis patient comprising performing sepsis treatment on a subject who has been subjected to a method for assisting detection of sepsis using an antibody of the first embodiment of the present invention or an antigen-binding antibody fragment thereof.

The method for assisting detection of sepsis may be the same as described in the second embodiment of the present invention. Sepsis treatment is not particularly limited to, but includes administration of an antibacterial agent or a steroid, a vasopressor, a replenisher solution, oxygen administration, artificial respiration management, sustained blood filtration dialysis, and plasma exchange.

10. Method of Screening Test Drug (or Therapeutic)

In a tenth embodiment of the present invention, the disclosure provides a method of screening a test drug (or therapeutic), comprising a step of determining the presepsin concentration in a sample of a subject to whom a test drug (or therapeutic) has been administered, using an antibody of the first embodiment of the present invention or an antigen-binding antibody fragment thereof, or a kit of the third embodiment. A disease to which a test drug is directed is not particularly limited so long as it is a disease in which the presepsin concentration in a sample of a subject is increased. Preferably, the presepsin concentration in a sample of a subject is compared between before and after test drug administration to determine whether the presepsin concentration after test drug administration is reduced in comparison with before administration or not. Alternatively, whether the presepsin concentration in a sample of a subject after test drug administration is reduced compared to a normal person that has not received the test drug may be determined.

In one embodiment, the present invention provides a method of screening a test drug comprising the following step:
1) a step of determining the presepsin concentration in a sample of a subject to whom a test drug has been administered 11. rsCD14ST-Fc rsCD14ST-Fc has a structure comprising a sequence of Position 1 to Position 64 of Sequence ID NO: 3 (human full length soluble CD14), and an Fc region of an antibody heavy chain.

rsCD14ST-Fc can be obtained, for example, by transfecting a plasmid for transient expression which expresses rsCD14ST-Fc, having a sequence having a thrombin recognizing sequence downstream of a sequence of Position 1 to Position 64 of human sCD14, and a sequence of an Fc region of a human-derived IgG1 antibody heavy chain, into a host cell such as a COS-1 cell, culturing the host cell, and recovering and purifying the resulting culturing supernatant.

It is desirable that a sequence facilitating cutting is inserted between a sequence of Position 1 to Position 64 of human sCD14 and Fc, and in addition to a thrombin recognizing sequence, for example, a Factor Xa recognizing sequence, a PreScission Protease recognizing sequence and the like may be used without particular limitation. It is not essential that rsCD14ST-Fc has a sequence facilitating cutting.

The Fc region of an antibody heavy chain in rsCD14ST-Fc is not limited. In addition to an Fc region derived from a human-derived IgGI antibody, Fc regions of all other known antibodies can be used. The host cell is also not particularly limited.

Since rsCD14ST-Fc is obtained by culturing a host cell such as a COS-1 cell and the like, expression is easy, and since Fc specifically binds to Protein A, and a Protein A column can be used for purification, it has an advantage in production that purification is also easy. Purification after cutting of an Fc region is possible using the conventional method in addition to the Protein A column, and purification may be performed, for example, using the method described in Example 13 of WO 2005/108429 or the like.

rsCD14ST-Fc can be also used as rsCD14-ST by cutting an Fc region, or can be used as rsCD14ST-Fc without cutting the Fc region, and both of them specifically bind to an anti-presepsin antibody.

rsCD14ST-Fc made in Example 9-(2) has the same thrombin sequence as that of a rsCD14-ST standard, which is inserted between rsCD14ST and Fc. rsCD14ST obtained by cutting an Fc region with thrombin has the same sequence as that of a rsCD14ST standard, and has the equivalent properties (see WO 2005/108429).

In preparation of rsCD14 from rsCD14ST-Fc, after cutting of Fc, only Fc can be easily removed by passing this through a Protein A column, and the preparation is also easy. A means for cutting an Fc region of rsCD14ST-Fc can be appropriately selected in conformity with an inserted sequence facilitating cutting.

Since rsCD14ST-Fc has the activity of rsCD14-ST without cutting the Fc region, it can be utilized as an antigen.

The previous rsCD14-ST standard is obtained by expressing rsCD14 in which a thrombin recognizing site is inserted between Position 64 and Position 65 of human sCD14, in a host cell, and cutting the rsCD14 at a thrombin recognizing site. A structure of rsCD14 comprises rsCD14-ST, but it shows little reactivity as rsCD14-ST. Only after cutting and purification does rsCD14-ST obtain an activity that becomes usable. On the other hand, since rsCD14ST-Fc can be used like rsCD14-ST or a standard regardless of whether the Fc region is cut. Thus, the labor of cutting can be saved, and it can be used simply.

EXAMPLES

Example 1: Production of Monoclonal Antibody Against Synthetic Peptide as Antigen 1-(1) Immunization of Rabbit The production of an administration antigen and the immunization of a rabbit were performed in accordance with the method described in Example 1 of WO 2004/044005 A1. Specifically, the peptide was produced by the peptide in which cysteine was inserted into the N terminal of a peptide (hereinafter, described as S68 peptide) consisting of the sequence described in SEQ ID NO.: 2 (corresponding to the sequence of Position 53 to Position 68 described in SEQ ID NO.: 3). This peptide was bonded to KLH (PIERCE) and it was used as an administration antigen (hereinafter, described as S68 peptide-KLH).

100 μg of S68 peptide-KLH was mixed with the same amount of Freund's complete adjuvant (DIFCO) and administered intradermally to the back of a New Zealand white rabbit (three month-old).

Two weeks thereafter and also one week after that, 100 μg of S68 peptide-KLH was mixed with the same amount of Freund's incomplete adjuvant (DIFCO) and administered intradermally to the back. Further, 20 μg of S68 peptide-KLH was administered twice to ear vein.

One week after completion of the administration, blood was sampled from ear vein and antiserum was separated according to a standard method, and the antibody titer and reactivity for presepsin were determined by using sandwich ELISA. Specifically, F1106-13-3 was immobilized to an immunoplate (MAXISORP, C96, 430341, manufactured by Nunc) and blocked. Each antiserum from rabbit was diluted with D-PBS (pH 7.4) and subjected to square serial dilution from ×1/1000 to ×1/32000 times (8 points). The reference standard of presepsin (rsCD14-ST described in Example 16 of WO 2005/108429) was diluted with a diluting solution (0.1% BSA/D-PBS) to prepare a standard solution of 3 ng/mL. After adding the antiserum dilution series to a plate, a standard solution of 3 ng/mL was subsequently added thereto. The plate reaction was occurred for an hour and, subsequently, the plate was washed five times with physiological saline containing 0.05% Tween20. Next, 100 μL of a solution obtained by diluting anti-rabbit Igs-HRP (DAKO, P448) was added and the reaction was occured for an hour at 25° C. After washing similarly the plate five times, a solution of tetramethyl benzidine (TMB, manufactured by BioFix) was added and reacted for 10 minutes at room temperature. Once the reaction is completed, the reaction was terminated with 1 M sulfuric acid solution. The absorbance at 450/650 nm was measured by using Multiskan JX (manufactured by Thermolab Systems). Based on the absorbance measurement result, a piece with high antibody titer was selected.

Four days before collecting a spleen, 400 μg of S68 peptide-KLH was administered to ear vein. After aseptic collection of the spleen, the lymphocytes were recovered.

1-(2) Cell Fusion and Cloning

According to the method described in U.S. Pat. No. 7,429,487, $2 \times 10^8$ cells of the lymphocytes and the $1 \times 10^8$ cells of immortalized B lymphocytes derived from a rabbit for the fusion partner were admixed with each other, and cell fusion was performed two divided times. The fused cells were sown on a 96-hole plate, and cultured according to a general method.

With regard to the culture supernatant of the obtained 286 clones, the binding activity for the administered antigen was determined by using S68 peptide-BSA, and 72 clones with confirmed binding activity were selected.

With regard to the 72 clones having confirmed binding activity for the administered antigen, the binding activity for a reference standard of presepsin was determined by the sandwich ELISA system, which is the same as 1-(1), and clones with confirmed binding activity were selected.

With regard to the clones with confirmed binding activity for a reference standard of presepsin, specificity for presepsin in blood of a patient was determined. Specifically, three examples of the serum from a normal person (manufactured by ProMedDx) and three examples of the serum form a patient having sepsis (manufactured by Bioreclamation) were diluted five times with a diluting solution and determined by the sandwich ELISA system, which is the same as 1-(1). As a result, five clones in which the reactivity with a reference standard of presepsin is good, absorbance does not increase in a sample from the normal person, and absorbance increases in a sample from the patient having sepsis were selected. Each clone was cloned by limiting dilution and each frozen ampule was prepared.

1-(3) Analysis for Binding Mode by BIACORE

In order to determine the binding mode between each antibody which has been obtained from the selected clone and presepsin, analysis was performed by using BIACORE3000 (manufactured by GE Health Care). On a CM5 chip (manufactured by GE Health Care), F1106-13-3 antibody was immobilized by a standard method and it was further added with a reference standard of presepsin (1 μg/ml). Diluted culture supernatant (0.5 μg/ml) was further added thereto and a sensorgram was plotted. All clones exhibited good binding mode from which no dissociation is observed in dissociation phase.

1-(4) Preparation of Rabbit Monoclonal Antibody

By using the obtained hybridoma producing a rabbit anti-presepsin monoclonal antibody, a rabbit monoclonal antibody was produced. Specifically, according to a standard method, the frozen ampule was thawed, and the cells were collected after culturing in RPMI1640 (manufactured by SIGMA™) containing 10% fetal bovine serum and 8% supplement A (manufactured by ABCAM®), and the cells were cultured using IS-MAB-CD medium (manufactured by Irvine) according to the protocol of CELLINE™ (manufactured by Integra Bioscience), and the culture supernatant containing the antibody was collected. Next, from the obtained culture supernatant, the antibody was purified by using rmp-Protein A SEPHAROSE™ FF (manufactured by GE Health Care). The elution solution containing the purified antibody was concentrated and subsequently dialyzed against D-PBS (pH 7.4). The protein concentration of the antibody was measured by Bradford method using bovine IgG (manufactured by BioRad) as a reference material. The obtained antibody was analyzed by SDS-PAGE, and as a result, a single band with a molecular weight of about 150 kDa was identified. Further, as a result of reduction, a heavy chain of about 50 kDa and a light chain of about 25 kDa were identified.

Example 2: Production of Recombinant Antibody

2-(1) Construction of Plasmid for Expression and Determination of Amino Acid Sequence in Variable Region of Rabbit Monoclonal Antibody From each hybridoma obtained from Example 1, total RNA was extracted by using RNEASY® Mini Kit (manufactured by Quiagen) and a single strand cDNA was synthesized by using SUPERSCRIPT™ VILO™ cDNA Synthesis Kit (manufactured by Invitrogen). By using the Rabbit Ig-Primer Set (Rader C, et al. JBC 2000; 275: 13668-76, and Lang I, et al. Gene 1996; 172: 295-8) which uses the obtained single strand cDNA as a template, the variable region was amplified by PCR and nucleotide sequence of the each variable region of the heavy chain and light chain was determined by a standard method.

A database search was performed with regard to the sequence information other than the variable region and the 5' side primer and 3' side primer were designed. By using those primers, PCR was performed to amplify each of the full length heavy chain and the full length light chain, which were then cloned into pTK-2433 having EF-1α promoter and CMV enhancer, that is, a vector for transient expression in mammalian cells. According to a standard method, the nucleotide sequence of each of the full length heavy chain and the full length light chain and the amino acid sequence encoded by them were determined. The amino acid sequences of the CDR part of the antibody variable region are illustrated in Table 10 (Heavy Chain) and Table 11 (Light Chain).

TABLE 10

| Antibody name | Heavy chain | | |
|---|---|---|---|
| | CDR1 | CDR2 | CDR3 |
| F1466-5 | RYAMG SEQ ID NO.: 4 | IIYRNIKT YYATWAKG SEQ ID NO.: 5 | GDF SEQ ID NO.: 6 |
| F1466-26 | RYTMG SEQ ID NO.: 7 | IINSGATY YASWAKG SEQ ID NO.: 8 | GDF SEQ ID NO.: 9 |
| F1466-16 | SFWMS SEQ ID NO.: 10 | IISDIDDL FYASWAKG SEQ ID NO.: 11 | GGL SEQ ID NO.: 12 |
| F1466-12 | SYDMI SEQ ID NO.: 13 | YIGSPGTT YYGSWAKG SEQ ID NO.: 14 | SGDIT NRFNL SEQ ID NO.: 15 |
| F1466-19 | NYDMI SEQ ID NO.: 16 | YIGSPGTT YYASWAKG SEQ ID NO.: 17 | SGDIT NRFNL SEQ ID NO.: 18 |

TABLE 11

| Antibody name | Light chain | | |
|---|---|---|---|
| | CDR1 | CDR2 | CDR3 |
| F1466-5 | QASEDIISNLA SEQ ID NO.: 19 | KASTLAS SEQ ID NO.: 20 | QSSYTESTTFGHV SEQ ID NO.: 21 |

TABLE 11-continued

| Antibody name | Light chain | | |
|---|---|---|---|
| | CDR1 | CDR2 | CDR3 |
| F1466-26 | QASQSIGSNLA SEQ ID NO.: 22 | KASKLAS SEQ ID NO.: 23 | QCSYTAIGNYGHV SEQ ID NO.: 24 |
| F1466-16 | QASQSISNYLA SEQ ID NO.: 25 | KTSTLES SEQ ID NO.: 26 | QSTYYRSTTTYGNT SEQ ID NO.: 27 |
| F1466-12 | QASERIRNWLS SEQ ID NO.: 28 | RASTLES SEQ ID NO.: 29 | QCSAGGNAGNA SEQ ID NO.: 30 |
| F1466-19 | QASERIRNWLS SEQ ID NO.: 31 | RASTLES SEQ ID NO.: 32 | QCSAGGNAGNG SEQ ID NO.: 33 |

2-(2) Preparation of Recombinant Antibody for Transient Expression

The plasmids for transient expression which have been produced in 2-(1) above (the expression plasmid containing the heavy chain sequence and the expression plasmid containing the light chain sequence) were admixed with each other in the same amount and COS-1 cells (ATCC: CRL-1650) were transfected with the mixture. Specifically, after mixing the transfection reagent at 2 μL/mL and the plasmid at 4 μL/mL and adding them to the medium, COS-1 cells were added thereto and cultured at 37° C. Seventy-two hours later, the culture supernatant was collected and added again to a fresh medium. Ninety-six hours later, the culture supernatant was collected and the fractions obtained by two collections were mixed and filtered through a 0.22 μm filter (STERIVAC™, manufactured by MILLIPORE®). The obtained culture supernatant was purified by the method described in 1-(4) above, and as a result of analysis by SDS-PAGE, a recombinant antibody showing a single band at about 150 kDa was identified.

2-(3) Construction of Plasmid for Stable Expression of Recombinant Antibody

By using a restriction enzyme, the gene fragment encoding the heavy chain and the gene fragment encoding the light chain were digested from the plasmids for transient expression which have been produced in 2-(2) above, and linked to the plasmid (pTK-2577; described in JP 2007-215546 A) containing EF-1α promoter and mouse DHFR expression unit [SV40 promoter as a promoter (not containing an enhancer region), polyA signal derived from SV40] to produce a plasmid for stable expression in mammalian animal cells.

Example 3: Manufacture of Antibody by CHO Cell

3-(1) Preparation of Recombinant Antibody-Production CHO Cell of Rabbit Monoclonal Antibody DHFR gene deficient CHO cells (CHO DXB11) were transfected with the plasmid for stable expression which has been constructed in 2-(3) above, and transformed CHO cells producing a rabbit antibody were established. Specifically, CHO DXB11 which has been acclimated and cultured with EX-CELL® 302 PF CHO (manufactured by JRH Bioscience) containing HT media Supplement (50×) HYBRI-MAX™ (manufactured by SIGMA™; used at 1× final concentration) and 200 mM L-Glutamine (manufactured by SIGMA™; used at final concentration of 4 mM) was centrifuged on the transfection day and inoculated to a flask at the concentration of 8×10⁶ cells/150 cm² Roux. By using 125 μl of FuGENEFUGEN® 6 (manufactured by PROMEGA®), 12.5 μg of the expression plasmid was prepared according to the protocol attached to FUGENE® 6 and then introduced to the CHO DXB11. After culturing for two days at 37° C., 5% CO₂, the cells were collected and washed twice with HT-free EX-CELL® 302 PF CHO medium containing 4 mM L-glutamine (hereinbelow, described as EX-CELL® (HT-)), and re-suspended in EX-CELL® (HT-). Next, the cells were sown again to a 96 well-plate at 12,500 to 50,000 cells/well and continuously cultured at 37° C., 5% CO₂. The half volume of the medium was replaced with fresh EX-CELL® (HT-) every three or four days. After continuing the culture for about two weeks, the cells within a well having an occurrence of a colony were transferred to a new plate.

The antibody in the culture supernatant of CHO cells was screened by the ELISA method which uses S68 peptide antigen as a solid phase, and then five kinds of CHO cells producing an antibody binding to S68 peptide were selected.

3-(2) Gene Amplification Using Methotrexate

By performing a gene amplification process that the transformed CHO cells for expressing the recombinant antibody obtained from 3-(1) were selected and cultured in EX-CELL® (HT-) medium containing methotrexate (hereinbelow, described as MTX), clones in which the production amount of a target recombinant antibody is increased were selected. Specifically, the transformed cells obtained from Example 3-(1) were suspended in EX-CELL® (HT-) medium containing 30 nM MTX and then spread on a 96 well-plate. The half volume of the medium was replaced every three or four days with fresh EX-CELL® (HT-) containing 30 nM MTX and the culture was continued at 37° C., 5% CO₂ until a colony is generated. IgG concentration in the culture supernatant of the obtained colony was determined by the ELISA method and clones exhibiting increased production amount were selected. As a result, the transformant exhibiting the production amount increased by two to ten times was obtained. Meanwhile, by subjecting the transformant with amplified gene to repeated selection and culture in a medium in which the MTX concentration is increased by three to ten times, it was possible to obtain the clones having further increased production amount.

3-(3) Production of Recombinant Antibody by CHO Cell

The clones obtained from 3-(2) were inoculated to CHO-SFM (HT-) medium (manufactured by GIBCO) containing 30 nM MTX to have 1×10⁵ cells/ml and cultured for seven days at 37° C. The obtained culture supernatant was used for purifying the antibody. The antibody was purified from the culture supernatant by using Protein A column (PROSEP®-A, manufactured by MILLIPORE®). As a result of analyzing the purified recombinant antibody by SDS-PAGE, an antibody showing the same molecular weight as the antibody derived from the hybridoma was identified.

Example 4: Evaluation of Reactivity of Each Antibody in Sandwich ELISA System

The reactivity with presepsin was evaluated for 5 kinds of the rabbit monoclonal antibodies prepared in Example 2, S68 antibody described in Example 1 of WO 2004/044005 A1 (polyclonal antibody obtained by the immunization of a rabbit with S68 peptide) and F1146-17-2 described in Example 2 of WO 2004/044005 A1 (monoclonal antibody obtained by the immunization of a rat with S68 peptide).

Specifically, each antibody was diluted to 5 μg/mL with PBS (pH 7.4) and 50 μL, thereof was added to each well of an immunoplate (MAXISORP™, manufactured by NUNC). After the overnight reaction at 4° C., washing with ion exchange water was performed five times and blocking was performed by adding to each well 200 μL, of PBS containing 0.1% STABILGUARD™ (manufactured by SurModics, Inc) and 0.1% TWEEN®20 (manufactured by Wako Pure Chemical Industries, Ltd.). Next, the reference standard of presepsin was diluted to 1,000 ng/mL using a diluting solution and subsequently diluted at the ratio of three times to prepare a serial dilution of the reference material. The serial dilution of the reference standard was added in an amount of 50 μL, per well and reacted for an hour at 25° C. Once the reaction is completed, it was washed five times with physiological saline containing 0.05% TWEEN®20, and 50 μL of peroxidase-labeled F1106-13-3 antibody which has been diluted to 0.25 μg/mL was added to each well. After the reaction for two hours at 25° C., washing was performed five times in the same manner as above, and a TMB solution was added to each well. After reaction for 20 minutes at room temperature, the reaction was terminated using 0.5 M sulfuric acid solution and the absorbance at 450 nm (sub-wavelength of 650 nm) was measured by using a plate spectrophotometer (manufactured by MOLECULAR DEVICES®).

The measurement results are shown in Table 12. Any measurement system using each rabbit monoclonal antibody prepared in Example 2 was excellent in the reactivity with the reference standard of presepsin, and showed nearly equivalent reactivity with that of the measurement system using S68 antibody.

On the other hand, the measurement system using F1146-17-2 showed low reactivity and 0.368 of the absorbance when the concentration of presepsin was 1000 ng/mL. This absorbance was nearly equivalent to the absorbance shown when the concentration of presepsin was 0.03 to 0.1 ng/mL in the measurement system using the rabbit monoclonal antibody. As stated the above, it was revealed that the measurement system using the rabbit monoclonal antibody improved the reactivity by about 10,000 folds in comparison with the measurement system using F1146-17-2. Since the presepsin concentration of a normal person sample is usually about 50 to 300 pg/mL, it was shown that measurement is impossible in a measurement system using F1146-17-2.

TABLE 12

| Presepsin concentration (ng/mL) | S68 antibody | F1466-5 | F1466-26 | F1466-16 | F1466-12 | F1466-19 | F1146-17-2 |
|---|---|---|---|---|---|---|---|
| 0 | 0.022 | 0.019 | 0.025 | 0.021 | 0.013 | 0.014 | 0.02 |
| 0.03 | 0.316 | 0.253 | 0.472 | 0.112 | 0.144 | 0.27 | 0.022 |
| 0.1 | 0.723 | 0.684 | 1.197 | 0.321 | 0.465 | 0.791 | 0.022 |
| 3 | 1.897 | 2.326 | 2.292 | 1.598 | 1.915 | 2.12 | 0.021 |
| 30 | 2.026 | 2.217 | 2.34 | 1.743 | 1.99 | 2.319 | 0.03 |
| 1000 | 1.697 | 2.155 | 2.274 | 1.69 | 1.869 | 1.985 | 0.368 |

Example 5: Measurement of Sample from Patient and Interference Test

The presepsin values in blood samples from 30 sepsis patients were measured by Sandwich ELISA system described in Example 4 using each antibody manufactured in Example 2, and it was analyzed for correlation with the measurement values by Sandwich ELISA system using S68 antibody.

As a result, in each ELISA system using the rabbit monoclonal antibody, there were two types of systems, one system showing good correlation with the measurement value by the ELISA system using S68 antibody and another system showing poor correlation. The results showed that the correlation coefficient of F1466-12 and F1466-19 to the rabbit monoclonal antibody was worse in comparison with the others. The correlation coefficients of respective antibodies were F1466–12=0.89, F1466–19=0.93 and F1466–26=0.98.

Next, the influences of interference substances in the blood (bilirubin F, bilirubin C, hemoglobin, rheumatism factor and triglyceride) on the presepsin measurement value were investigated in Sandwich ELISA systems manufactured using each of the rabbit monoclonal antibodies and S68 antibody, respectively. Each of the interference substances in stepwise concentrations was added into the serum of healthy volunteers contained with a fixed amount of presepsin and the concentration of presepsin was measured, and the influence of each of the interference substances on the measurement value was evaluated on the basis of the measurement value when the interference substance was not added.

As a result, the interference of bilirubin F, bilirubin C, hemoglobin and the rheumatism factor was not a problematic level in the measurement systems using any antibody.

On the other hand, triglyceride (TG) had an influence on the measurement system using some antibodies. The TG interference test was carried out as described below. Human serum of healthy volunteers to which a certain amount of presepsin was added, was used as a sample. Samples diluted in series to 20 mg/mL of TG concentration in the samples were produced using 20% INTRALIPID® transfusion (Fresenius SE & Co. KGaA). TG originally contained in the serum of the sample is not considered in this TG concentration. The diluted samples were diluted by 20 folds with a sample dilution solution, and the presepsin value was measured by ELISA. This TG interference test was carried out for plural samples.

As a result, TG addition had an influence on the measurement value of presepsin in the measurement system using F1466-12 and F1466-19 antibodies, and the ratio of the sample showing greater than ±20% of the separation degree of the presepsin measurement value was high when the TG concentration in the sample was 20 mg/mL.

In addition, a separation degree of the presepsin measurement value at the TG concentration in a sample of 20 mg/mL was obtained in a plurality of samples, and an average of the separation degree was calculated for each antibody. As a result, an average of the separation degree exhibits ±20% or less in a measurement system using the S68 antibody, F1466-5, and F1466-26. On the other hand, in a measurement system using antibodies of F1466-12, F1466-19, and F1466-16, the result was that an average of the separation degree exceeds ±20%.

Furthermore the dissociation degrees of the presepsin measurement values by TG addition were compared between an assay system using each rabbit monoclonal antibody and an assay system using S68 antibody. Thus, when TG concentration in the sample was 20 mg/mL by TG addition, the samples showing greater than 20% over-represent in both the difference between the dissociation degree of the measurement system of F1466-12 and the dissociation degree of the measurement system of S68 antibody, and the difference between the dissociation degree of the measurement system of F1466-19 and the dissociation degree of the measurement system of S68 antibody, high This suggests the possibility that the difference in the performances of the antibodies in the TG interference test has an influence on the correlation analysis as described above.

The interference substance test was attempted for F1146-17-2, but the data was not obtained due to low reactivity.

Example 6: Specificity of Antibody; Analysis for Epitope

The epitopes of each of the rabbit monoclonal antibodies and F1146-17-2 manufactured in Example 2 (monoclonal antibody obtained by the immunization of a rat with S68 peptide) was analyzed. 8 kinds of peptides consisting of 10 amino acids containing the partial fragment of the peptide sequence of SEQ ID NO.: 2, which was used as the administration antigen in Example 1, were synthesized (see Table 13). The epitope sequence was investigated by observing the competition-inhibition reaction with a presepsin reference standard by Sandwich ELISA system described in Example 4. Specifically, immobilization plates of each antibody were prepared in accordance with the method described in Example 4. Next, 400 pg/mL of the presepsin reference standard and 20 μg/mL of the synthetic peptides shown in Table 13 (P01 to P08) were added in 25 μL, respectively to the plates, and reacted. No addition of the peptide (described as PBS) and a peptide for a negative control (described as NC: Sequence CGDKTTATDIKGKE (SEQ ID NO.: 34)) were used as a negative control. In addition, S68 peptide was used as a positive control. The reaction system was color-developed with TMB after the reaction was comleted. If the synthetic peptide reacted with the antibody, the absorbance decreased because binding of the presepsin reference standard to the antibody was inhibited. The inhibition rate of each peptide was calculated when the absorbance of PBS was assumed 100%. As results thereof, an antibody recognizing P03 only, an antibody recognizing P03 to P04, and an antibody recognizing P04 to P05 were confirmed as shown in Table 14. In addition, it was revealed that F1146-17-2 recognized P04 to P05.

As results thereof, it was revealed that a monoclonal antibody recognizing the location of P03 as the epitope was obtained. It was found out that F1466-12 and F1466-19, which showed worse results in the TG interference test and the correlation with the measurement system using S68 antibody in Example 5, recognized P04 to P05 and did not recognize P03 as the epitope similarly to the rat monoclonal antibody (F1146-17-2). The other antibodies recognized P03 as the epitope. This suggests that there is the relationship between the suitable ability for presepsin measurement of the antibody and the epitope which the antibody recognizes. In addition, presepsin has an amino acid sequence which is greatly deficient in a C end portion of high molecular weight sCD14, and it is supposed that the length of an amino acid thereof has variation. It is possible that a difference in specificity of an antibody influenced correlation with the measurement value using the S68 antibody in Example 5.

TABLE 13

| | Location of amino acid in SEQ ID NO.: 3 | Amino acid sequence | SEQ ID NO.: |
|---|---|---|---|
| S68 peptide | Position 53 to Position 68 | rvdadadprqyadtvk | 2 |
| P01 | Position 46 to Position 55 | nlepflkrvd | 35 |
| P02 | Position 49 to Position 58 | pflkrvdada | 36 |
| P03 | Position 52 to Position 61 | krvdadadpr | 1 |
| P04 | Position 55 to Position 64 | dadadprqya | 37 |
| P05 | Position 58 to Position 67 | adprqyadtv | 38 |
| P06 | Position 61 to Position 70 | rqyadtvkal | 39 |
| P07 | Position 64 to Position 73 | adtvkalrvr | 40 |
| P08 | Position 67 to Position 76 | vkalrvrrlt | 41 |

TABLE 14

| | F1466-5 | F1466-26 | F1466-16 | F1466-12 | F1466-19 | F1146-17-2 |
|---|---|---|---|---|---|---|
| P01 | − | − | − | − | − | − |
| P02 | − | − | − | − | − | − |
| P03 | ++ | ++ | ++ | − | − | − |
| P04 | − | − | ++ | ++ | ++ | ++ |
| P05 | − | − | − | ++ | ++ | ++ |
| P06 | − | − | − | − | − | − |
| P07 | − | − | − | − | − | − |
| P08 | − | − | − | − | − | − |
| S68 | ++ | ++ | ++ | ++ | ++ | ++ |

Residual reactivity (%)
−: 80% or more, +: 50% or more and less than 80%, ++ less than 50%

Example 7: Detailed Analysis for Epitope

With respect to the rabbit monoclonal antibody recognizing P03 peptide, the reactivity with peptides obtained by modifying P03 peptide for one amino acid was investigated. Peptides (P031 to P039 peptides) obtained by substituting the amino acids at Position 53 to Position 61 with alanine (glycine when the original amino acid is alanine) for one amino acid in P03 peptide (corresponding to the amino acid sequence of SEQ ID NO.: 1, and the amino acid sequence consisting of the sequence of Position 52 to Position 61 of SEQ ID NO.: 3), were synthesized, and the reactivities between P031 to P039 peptides and the antibody were confirmed by Sandwich ELISA system in accordance with the description of Example 4.

As a result, the binding activity with the antibody was lost when the aspartic acid at Position 59 of SEQ ID NO.: 3 in P03 peptide (corresponding to Position 8 of SEQ ID NO.: 1) was substituted with alanine.

The binding activity with the antibody was maintained when the amino acids at Position 53 to Position 58 of SEQ ID NO.: 3 (corresponding to the amino acids of Position 2 to Position 7 of SEQ ID NO.: 1), Position 60 and Position 61 of SEQ ID NO.: 3 in P03 peptide (corresponding to Position 9 and Position 10 of SEQ ID NO.: 1) were substituted with alanine (or glycine).

As described above, it is confirmed that the antibody recognizing P03 peptide as an epitope recognizes peptides as an epitope which the peptides were obtained by substituting the amino acids at Position 53 to Position 58, Position 60, and Position 61 described in SEQ ID NO.: 3 in P03 peptide with alanine (or glycine) for one amino acid.

Example 8: Preparation of Variant of Anti Presepsin Monoclonal Antibody Derived from Rabbit Based on the sequence of an anti presepsin monoclonal antibodies derived from rabbit described in Example 1, variants were prepared.

8-(1) Analyzing of CDR Sequence

As a result of analyzing CDR sequence of five kinds of the anti presepsin antibodies which have been obtained from Example 1, it was presumed that the sequence of each antibody has a sequence affecting the antibody activity and a sequence not affecting the antibody activity. Thus, by using as a base the CDR sequence of F1466-26 antibody, which is one of the antibodies clearly shown to recognize the sequence of P03 (SEQ ID NO: 1) as an epitope in Example 6, amino acid modification of each CDR sequence was performed to prepare a variant and the activity of the variant was evaluated. About 100 variants were prepared. The amino acid modification was performed by substitution, insertion or deletion of an amino acid, or substitution of a sequence with several amino acids.

A variant containing the entire length of heavy chain of F1466-26 antibody and the entire length of light chain of F1466-5 antibody was also prepared and evaluated in the same manner as above.

8-(2) Preparation of Plasmid for Preparing Heavy Chain Modified Product

A plasmid for a heavy chain modified product was prepared as follows. Although descriptions are given for plasmid pTK-5793, other plasmids were also constructed according to the same method. By using as a template the plasmid for transient expression of a heavy chain (pTK-5605) containing the entire length of the heavy chain of F1466-26 obtained from Example 2 and a pair of primers (rabbit IgG (14-12)-e: 3' side primer and Aor13HI-rabbit IgV2: 5' side primer), PCR was performed. By also using the amplified fragment obtained as a template and a pair of primers (rabbit IgG (14-12)-e and Aor13HI-rabbit IgV2), PCR was performed. The amplified fragment obtained therefrom was cloned into plasmid pT7-Blue and then a fragment including a desired sequence was prepared by using the restriction enzyme Aor13HI. Furthermore, pTK-4273 (manufactured by our company) having a EF-1α promoter and a CMV enhancer, and further gene sequence comprising other parts other than rabbit IgG heavy chain variable region, which is a vector for transient expression in mammalian cells, was digested with restriction enzyme Aor13HI to prepare a vector fragment. The prepared fragment which contains the desired sequence was cloned into the vector fragment to prepare pTK-5793.

8-(3) Preparation of Plasmid for Preparing Light Chain Modified Product

A plasmid for a light chain modified product was prepared as follows. Although descriptions are given for plasmid pTK-5844, other plasmids were also constructed according to the same method. By using as a template the plasmid for transient expression of a light chain (pTK-5608) containing the entire length of the light chain of F1466-26 obtained from Example 2 and a pair of primers (pEF2ce-28: 3' side primer and pEF2ce-49: 5' side primer), PCR was performed. By also using the amplified fragment obtained as a template and a pair of primers (pEF2ce-28 and pEF2ce-49), PCR was performed. The amplified fragment obtained therefrom was cloned into plasmid pT7-Blue and then a fragment including a desired sequence was prepared by using the restriction enzymes BamHI and XbaI. Furthermore, pTK-2433 (manufactured by our company), which is a vector for transient expression in mammalian cells, was digested with restriction enzymes BamHI and XbaI to prepare a vector fragment. The prepared fragment which contains the desired sequence was cloned into the vector fragment to prepare pTK-5844.

Sequence of Primers

```
rabbit IgG (14-12)-e:
                                    (SEQ ID NO.: 85)
5'GGG GGT CCG GAG GTC GCC TGG TCA CGC CTG G3'

Aor13HI-Rabbit IgV2:
                                    (SEQ ID NO.: 86)
5'GGG TCC GGA GGA GAC GGT GAC CAG GGT GCC3' pEF2ce-28:
                                    (SEQ ID NO.: 87)
5' TTC ATT CTC AAG CCT CAG AC 3' pEF2ce-49:
                                    (SEQ ID NO.: 88)
5' TTT TCA CTG CAT TCT AGT TGT GGT 3'
```

8-(4) Preparation of Recombinant Antibody in Transient Expression System

Hereinbelow, the method for transient expression of an antibody using the plasmid pTK-5793 for preparing a heavy chain modified product is shown as a representative example. The plasmid (pTK-5793) for preparing the heavy chain modified product which has been prepared in Example 8-(2) and plasmid (pTK-5608) for transient expression of a light chain which has been described in Example 8-(3) were mixed in the same amount and COS-1 cells (ATCC: CRL-1650) were transfected with them by using a transfection reagent (FuGENE® 6, Promega® KK). Specifically, by using Opti-MEM® Reduced Serum Medium (manufactured by Life Technologies) as a liquid for dilution, a transfection reagent and the plasmid were prepared at 0.96 µL/25 µL and 0.48 µg/25 respectively. After mixing and addition to a medium, they were added to COS-1 cells, which were then cultured at 37° C. After culturing for 72 hours, the culture supernatant was collected.

Similar to above, the plasmid for preparing each heavy chain modified product was used after mixing with the plasmid (pTK-5608) for transient expression of a light chain. The plasmid for preparing each light chain modified product was used after mixing with the plasmid (pTK-5605) for transient expression of a heavy chain. The modified product including the entire length of the heavy chain of the F1466-26 antibody and the entire length of the light chain of F1466-5 antibody was prepared by mixing with the pTK-5605 and a plasmid for transient expression of a light chain which includes the entire length of the light chain of F1466-5.

Example 9: Evaluation of Variant (1)

Sixteen kinds of the variants (IgG antibodies) which were obtained by expression in COS-1 cells in Example 8 were purified and the reactivity with presepsin, specificity, and affinity (KD value) of each antibody were evaluated.

9-(1) Purification of Antibody

The culture supernatant of COS-1 cells obtained from 8-(4) was collected and filtered through a 0.22 µm filter (STERIVAC, MERCK MILLIPORE®). The obtained culture supernatant was purified by using ProsepPROSEP®-vA MERCK MILLIPORE®). An eluate containing the purified product was concentrated and subsequently dialyzed against D-PBS (pH 7.4). The protein concentration was obtained by Lowry method using IgG (BioRad Laboratories, Inc.) as a standard. The obtained antibody was analyzed by SDS-PAGE. As a result, a recombinant antibody showing a single band of about 150 kDa was determined.

9-(2) Preparation of rsCD14ST-Fc in Transient Expression System

First, by using as a template pTK356H (TB64) (a plasmid having a sequence encoding rsCD14 which is described in Example 13 of WO 2005/108429), a pair of primers (hCD14-a, hCD14-d) and a Taq polymerase (TAKARA BIO INC.), PCR reaction was performed. The amplified fragment obtained therefrom (containing a thrombin recognizing sequence (cleavage site) at downstream of the sequence of position 1 to position 64 of human sCD14 which includes a signal sequence, and a restriction enzyme site at both ends) was used for TA cloning in the pT7Blue™ vector (MERCK MILLIPORE®). After confirming the sequence, it was used as pTK-3047. Next, the fragment obtained by digesting the pTK-3047 with the restriction enzymes EcoRI and BamHI was inserted to a vector fragment which has been prepared in advance by restriction of pTK-2233 (a plasmid for mammalian cell expression containing a sequence encoding Fc region of the heavy chain of IgG1 antibody heavy chain derived from human) with EcoRI and BamHI, and the obtained clone was used as pTK-3053.

```
Sequence of hCD14-a
                                    (SEQ ID NO.: 89)
5'-GGGAATTCGCCGCCACCATGGAGCGCGCGTCCTGC-3'

Sequence of hCD14-d
                                    (SEQ ID NO.: 90)
5'-GGGATCCACGCGGAACCAGAGCATACTGCCGCGGG-3'
```

COS-1 cells (ATCC: CRL-1650) were transfected with the plasmid pTK-3053 for transient expression for expressing rsCD14ST-Fc. Specifically, a transfection reagent and the plasmid were admixed with each other at 2 µL/mL and 4 µg/mL, respectively. After mixing and addition to a medium, they were added to COS-1 cells, which were then cultured at 37° C. After culturing for 72 hours, the culture supernatant was collected and a fresh medium was further added thereto. After culturing for 96 hours, the culture supernatant was collected and fractions obtained from two collections were mixed and filtered through a 0.22 µm filter (STERIVAC™, MERCK MILLIPORE®). The obtained culture supernatant was purified by using ProsepPROSEP®-vA (MERCK MILLIPORE®). An eluate containing the purified product was concentrated and subsequently dialyzed against D-PBS (pH 7.4). The protein concentration was obtained by Lowry method using BSA (BioRad Laboratories, Inc.) as a standard. The obtained rsCD14ST-Fc was analyzed by SDS-PAGE. As a result, a single band with molecular weight of about 75 kDa was determined. The binding activity of the prepared rsCD14ST-Fc to an anti presepsin antibody was determined by ELISA in which an antigen is immobilized in a solid phase.

9-(3) Establishment of Sandwich ELISA

By using the variant which has been purified in 9-(1), sandwich ELISA was established. Specifically, each variant was immobilized onto IMMUNO PLATE (MAXISORP, C96, 430341) manufactured by Nunc followed by blocking. Next, by adding a standard product of presepsin (0 to 300 pg/mL), the plate was reacted for one hour at 25° C. Subsequently, the plate was washed five times with physiological saline containing 0.05% Tween 20. Next, a solution containing diluted F1106-13-3 F(ab')2-HRP was added to each well and the reaction was allowed to occur for 2 hours at 25° C. Similarly, after washing the plate five times, a TMB solution was added and the reaction was allowed to occur for 20 minutes at room temperature. When the reaction was completed, the reaction was terminated by using a 1 M sulfuric acid solution. The absorbance at 450/650 nm was measured by using a plate reader.

9-(4) Evaluation of Specificity (1)

In order to evaluate the specificity of the variant which has been purified in 9-(1), ELISA was performed by using a plate to which P03 peptide (SEQ ID NO: 1, prepared in Example 6) is immobilized. For the comparison, evaluation of F1466-26 was also performed.

Specifically, BSA or P03 peptide-BSA was immobilized onto IMMUNO PLATE (MAXISORP, C96, 430341) by Nunc followed by blocking.

Based on the result of protein concentration which has been obtained from 9-(1), dilution with D-PBS was made and preparation was made to have 500 ng/mL. Each diluted solution was added in an amount of 50 µL per well and the reaction was allowed to occur in the plate for one hour. Subsequently, the plate was washed five times with physiological saline containing 0.05% Tween 20. Next, a solution in which anti rabbit Igs-HRP (DAKO, P448) is diluted was added to each well and the reaction was allowed to occur for one hour at room temperature. Similarly, after washing the plate, a TMB solution was added and the reaction was allowed to occur for 3 to 5 minutes at room temperature. When the reaction is completed, the reaction was terminated by using a 1 M sulfuric acid solution. The absorbance at 450/650 nm was measured by using a plate reader (Molecular Devices). Together with the modified CDR sequence of the variant, the results are shown in Table 15 to Table 22—Entire length of light chain in modified region.

As a result, it was found that 87% of variants bind to the P03 peptide, and thus it was demonstrated that the P03 site is recognized as an epitope. Specifically, it was demonstrated that 5795, 5803, 5811, 5810, 5784, 5793, 5858, 5878, 5875, 5876, 5844, 5874, and 5684 recognized P03 site as an epitope among the obtained modified products.

9-(5) Evaluation of Affinity

Affinity (KD) of the variant to presepsin (rsCD14ST-FC prepared in 9-(2) was used), the P03 peptide, and the S68 peptide was evaluated.

The evaluation was also made similarly for the S68 antibody, a monoclonal antibody derived from rat (F1146-17-2), and the F1146-26.

Measurement of the affinity was performed by using BIACORE3000 (GE Healthcare). Onto a CM5 chip (GE Healthcare), each of the rsCD14ST-Fc, P03-BSA and S68-BSA was immobilized according to a common method and dilution series of each antibody (1.6 to 1000 nM) was added and the binding mode for each antigen was determined. A sensorgram was plotted, and by obtaining the association rate constant (Ka) and the dissociation rate constant (Kd), the equilibrium dissociation constant (KD) was calculated.

The result of measuring the affinity (KD) of the S68 antibody, the monoclonal antibody derived from rat (F1146-17-2), and F1146-26 for the rsCD14ST-FC is shown in Table 15.

As a result, it was found that, the F1146-26 (KD value of 1.48E-09) has an affinity for presepsin that is about ten times higher than that of S68 antibody (KD value of 1.08E-08) in terms of the KD value. It was also found that, the F1146-26 has an affinity for presepsin (KD value) that is about ten thousand times higher than that of a monoclonal antibody derived from rat (F1146-17-2: KD value of 1.08E-05).

The result of measuring the affinity (KD) of each variant for the rsCD14ST-FC is shown in Table 15 to Table 22—Entire length of light chain in modified region, together with the modified CDR sequence.

As a result, it was found that 80% of the variant have an affinity which is greater than or equal to that of the S68 antibody. According to the modification of the CDR sequence of the F1146-26, a variant (5810) having an affinity for presepsin (KD value) that is about one thousand times higher than that of the F1146-26 was obtained.

One preferred embodiment of the present invention is an antibody which has higher antibody affinity for presepsin compared to the affinity of S68 antibody for presepsin. When comparison is made in terms of KD value, examples of the preferred antibody include F1466-26, and 5795, 5803, 5810, 5784, 5793, 5858, 5844, and 5684 as a variant. Furthermore, an antibody exhibiting antibody KD value of less than $10^{-8}$ is also favorable and F1466-26, 5795, 5803, 5810, 5784, 5793, 5858, 5844, and 5684 were also noted. Furthermore, an antibody having excellent affinity for presepsin by presepsin showing KD value that is ½ or less than the KD value of the S68 antibody is also preferable and F1466-26, 5795, 5803, 5810, 5784, and 5793 were also noted. Those exhibiting a particularly excellent KD value were 5793 (7.3E-10) and 5810 (6.52E-12).

It was found that the variant 5684 in which the entire length of heavy chain of F1146-26 and the entire length of light chain of F1146-5 are combined maintains the P03 specificity and the binding activity for presepsin. Because F1146-26 and F1146-5 are the antibodies which recognize the same P03 site as an epitope site, it was demonstrated that the antibody activity can be possibly maintained even when sequence substitution is made between antibodies having the same specificity.

As shown in Example 2, any one of the heavy chain CDR3 sequence of F1146-5 and F1146-26 which recognizes P03 as an epitope is GDF and composed of a relatively short sequence, that is, three amino acids. As such, it is believed to be a characteristic of the present antibody.

Furthermore, because an increase in the affinity was observed in the variant 5793 according to the modification of the $3^{rd}$ of the heavy chain CDR3, it was demonstrated that the $3^{rd}$ of the heavy chain CDR3 sequence may possibly have an effect on the antibody activity.

TABLE 15

| Antibody | Epitope | rsCD14ST-Fc (KD) |
|---|---|---|
| S68 antibody | | 1.08E−08 |
| F1466-17-2 (rat) | P04-05 | 1.08E−05 |
| F1146-26 (rabbit) | P03 | 1.48E−09 |

TABLE 16

Heavy chain CDR1 of modified region
(SEQ ID NOS 167, 95, 96, and 98, respectively, in order of appearance)

| Antibody | VH CDR1 | | | | | P03(OD) | rsCD14ST-Fc(KD) |
|---|---|---|---|---|---|---|---|
| F1466-26 | R | Y | T | M | G | 0.822 | 1.48E−09 |
| 5795 | | | A | | | 2.480 | 1.71E−09 |
| 5803 | S | | | | | 1.631 | 4.20E−09 |
| 5811 | A | | | | | 1.030 | 1.13E−08 |

TABLE 17

Heavy chain CDR2 of modified region
(SEQ ID NOS 169 and 97, respectively, in order of appearance)

| Antibody | VH CDR2 |   |   |   |   |   |   |   |   |   |   |   | P03(OD) | rsCD14ST-Fc(KD) |
|---|---|---|---|---|---|---|---|---|---|---|---|---|---|---|
| F1466-26 | I | I | N | S | G | A | T | Y | Y | A | S | W | A | K | G | 0.822 | 1.48E−09 |
| 5810 |   |   | A |   |   |   |   |   |   |   |   |   |   |   |   | 2.048 | 6.52E−12 |

In 5810, A was inserted between I at the 2nd and N at the 3rd.

TABLE 18

Heavy chain CDR3 of modified region
(SEQ ID NOS 170, 93, 94 and 177, respectively, in order of appearance)

| Antibody | VH CDR3 |   |   | P03(OD) | rsCD14ST-Fc(KD) |
|---|---|---|---|---|---|
| F1466-26 | G | D | F | 0.822 | 1.48E−09 |
| 5784 | A |   |   | 1.018 | 3.73E−09 |
| 5793 |   |   | A | 0.881 | 7.30E−10 |
| 5794 | A | A | A | 0.582 | 4.06E−07 |

TABLE 22

Entire length of light chain in modified region

| Antibody | VL | P03 (OD) | rsCD14ST-FC (KD) |
|---|---|---|---|
| F1146-26 | — | 0.822 | 1.48E−09 |
| 5684 | — | 1.137 | 7.37E−09 |

TABLE 19

Light chain CDR1 of modified region
(SEQ ID NOS 172, 100, 103, and 178, respectively, in order of appearance)

| Antibody | VL CDR1 |   |   |   |   |   |   |   |   |   | P03(OD) | rsCD14ST-Fc(KD) |
|---|---|---|---|---|---|---|---|---|---|---|---|---|
| F1466-26 | Q | A | S | Q | S | I | G | S | N | L | A | 0.822 | 1.48E−09 |
| 5858 |   |   |   |   |   | A |   |   |   |   |   | 0.946 | 9.04E−09 |
| 5878 |   |   |   |   |   |   |   | S | N | Y |   | 2.327 | 1.43E−08 |
| 5879 |   |   |   |   |   |   |   | S | I | Y |   | 0.352 | 8.42E−07 |

TABLE 20

Light chain CDR2 of modified region
(SEQ ID NOS 172, 100, 103, and 178, respectively, in order of appearance)

| Antibody | VL CDR2 |   |   |   |   |   | P03(OD) | rsCD14ST-Fc(KD) |
|---|---|---|---|---|---|---|---|---|
| F1466-26 | K | A | S | K | L | A | S | 0.822 | 1.48E−09 |
| 5875 | T |   | T |   |   | E |   | 1.038 | 1.96E−08 |
| 5876 | T |   | T |   |   | D |   | 0.657 | 1.97E−06 |

TABLE 21

Light chain CDR3 of modified region
(SEQ ID NOS 174, 99, and 101, respectively, in order of appearance)

| Antibody | VL CDR3 |   |   |   |   |   |   |   |   |   | P03(OD) | rsCD14ST-Fc(KD) |
|---|---|---|---|---|---|---|---|---|---|---|---|---|
| F1466-26 | Q | C | S | Y | T | A | I | G | N | Y | G | H | V | 0.822 | 1.48E−09 |
| 5844 |   |   |   |   |   |   |   |   |   | A |   |   |   | 0.677 | 9.82E−09 |
| 5874 |   | S |   |   |   | E | S | T | T | F |   |   |   | 2.108 | 1.95E−08 |

In 5844, A was inserted between N at the 9th and Y at the 10th.

9-(6) Evaluation of Specificity (2)—Peptide Competitive Inhibition Reaction

According to Example 6, a test for the competitive inhibition reaction by P01 to P08 peptides for the reaction between each variant and presepsin was performed.

The test was performed by using ELISA in which the variant is immobilized in a solid state. Specifically, the variant was immobilized onto IMMUNO PLATE (MAXISORP, C96, 430341) by Nunc followed by blocking. Then, the standard presepsin (300 pg/mL) was added to each well in an amount of 25 µL per well. Subsequently, each peptide which has been diluted (0.01 to 10 μg/mL) was added in an amount of 25 μL. The reaction was allowed to occur in the plate for one hour at 25° C. Subsequently, the plate was washed five times with physiological saline containing 0.05% Tween 20. Next, a solution in which F1106-13-3 F(ab')2-HRP is diluted was added to each well in an amount of 50 μL per well and the reaction was allowed to occur for 2 hours at 25° C. Similarly, after washing the plate five times, a TMB solution was added and the reaction was allowed to occur for 30 to 40 minutes at room temperature. When the reaction is completed, the reaction was terminated by using a 1 M sulfuric acid solution. The absorbance at 450/650 nm was measured by using a plate reader. As a negative control, a sample without adding the peptide (described as PBS) was used. As a positive control, S68 peptide was used. By having the absorbance of PBS as 100%, the inhibition ratio of each peptide was calculated. As a result, all the variants which have been tested were confirmed to specifically recognize the P03 sequence.

TABLE 23

|     | 5793 | 5795 | 5803 | 5810 | 5811 | 5858 | 5874 |
|-----|------|------|------|------|------|------|------|
| P01 | –    | –    | –    | –    | –    | –    | –    |
| P02 | –    | –    | –    | –    | –    | –    | –    |
| P03 | ++   | ++   | ++   | ++   | ++   | ++   | ++   |
| P04 | –    | –    | –    | –    | –    | –    | –    |
| P05 | –    | –    | –    | –    | –    | –    | –    |
| P06 | –    | –    | –    | –    | –    | –    | –    |
| P07 | –    | –    | –    | –    | –    | –    | –    |
| P08 | –    | –    | –    | –    | –    | –    | –    |
| S68 | ++   | ++   | ++   | ++   | ++   | ++   | ++   |

Residual reactivity (%)
–: 80% or more, +: 50% or more and less than 80%, ++ less than 50%

Example 10: Evaluation of Variant (2)

Among the variants prepared in Example 8, the binding activity for presepsin and specificity were evaluated for the variant which has not been evaluated in Example 9.

10-(1) Measurement of Antibody Concentration by ELISA

In order to determine the IgG concentration in the culture supernatant obtained from Example 8-(4), IgG concentration was measured by using sandwich ELISA. Specifically, anti-rabbit antibody (DAKO, Z196) was immobilized onto IMMUNO PLATE (MAXISORP, C96, 430341) by Nunc followed by blocking. By using the purified rabbit monoclonal antibody as a standard, a standard solution at 100 to 1.56 ng/mL was prepared according to dilution with a diluting liquid (0.1% BSA/D-PBS). Next, the collected culture supernatant was diluted with the diluting liquid (0.1% BSA/D-PBS). The diluted solution of the culture supernatant or dilution series of the standard was added to a well, and the reaction was allowed to occur for one hour in a plate. Subsequently, the plate was washed five times with physiological saline containing 0.05% TWEEN®20. Next, a solution in which anti rabbit Igs-HRP (DAKO, P399) is diluted was added to each well and the reaction was allowed to occur for one hour at room temperature. Similarly, after washing the plate five times, a tetramethyl benzidine (TMB, BIOFIX®) solution was added and the reaction was allowed to occur for 10 minutes at room temperature. When the reaction is completed, the reaction was terminated by using a 1 M sulfuric acid solution. The absorbance at 450/650 nm was measured by using a plate reader (MOLECULAR DEVICES®). The antibody concentration in each culture supernatant was measured by using a standard curve which has been obtained from serial concentration dilution of the standard.

10-(2) Evaluation of Binding Activity and Specificity for Presepsin

In order to evaluate the biding activity and specificity for presepsin of the variant, ELISA was performed by using a plate in which an antigen is immobilized in a solid state.

Specifically, BSA, rsCD14ST-Fc, or P03 peptide-BSA was immobilized onto IMMUNO PLATE (MAXISORP, C96, 430341) by Nunc followed by blocking.

Based on the result of IgG concentration in the culture supernatant, dilution of the culture supernatant with D-PBS was made to have 500 ng/mL (for a sample with low antibody concentration, the original stock of the culture supernatant was used). Each diluted solution of a supernatant was added in an amount of 50 μL per well and the reaction was allowed to occur in the plate for one hour. Subsequently, the plate was washed five times with physiological saline containing 0.05% Tween20. Next, a solution in which anti rabbit Igs-HRP (DAKO, P448) is diluted was added to each well and the reaction was allowed to occur for one hour at room temperature. Similarly, after washing the plate, a TMB solution was added and the reaction was allowed to occur for 3 to 5 minutes at room temperature. When the reaction is completed, the reaction was terminated by using a 1 M sulfuric acid solution. The absorbance at 450/650 nm was measured by using a plate reader (Molecular Devices).

For the comparison, the evaluation of S68 antibody was also performed with the evaluation of the binding activity for presepsin. The binding activity for presepsin was shown as the ratio of absorbance at the time of reaction between each antibody and rsCD14ST-Fc, when the absorbance at the time of reaction between the S68 antibody and sCD14ST-Fc is set at 1.

Together with the modified sequence of each variant, the results are shown in Table 24 to Table 29.

As a result, it was found that most of the antibodies bind to the P03 peptides, and thus it was demonstrated that the P03 site is recognized by 76% of antibodies as an epitope.

Furthermore, it was found that F1466-26 and most of the variants exhibited the absorbance ratio which is higher by about 4 to 5 times compared to the S68 antibody, and thus they have an excellent binding activity for presepsin. Compared with the KD value and absorbance ratio of F1466-26 for presepsin, it is supposed that the KD value of these antibodies will be the same level as the favorable KD value of antibodies measured in example 9.

One preferred embodiment of the present invention is an antibody which has a binding activity for presepsin higher than that of the S68 antibody. For example, in terms of the absorbance as described in Examples, it is believed that an antibody showing absorbance higher than that of the S68 antibody, preferably an antibody showing absorbance higher by at least 2 times than that of the S68 antibody, is preferable.

An antibody which exhibits, as a binding activity for presepsin, the absorbance 5 fold or more than that of S68 antibody and has a particularly excellent binding property was 5934, 5935, 5939, 5944, 5808, 5809, 5824, 5979, 5980, 5983, 5984, 5987, 5988, 5860, 5864, and 5863 among the obtained antibodies, 5979, 5983, 5988, and 5864 exhibited the absorbance 5.5 fold or more than that of S68 antibody and had a particularly excellent binding activity for presepsin among them.

TABLE 10

Heavy chain CDR1 of modified region
(SEQ ID NOS 167, 129-139, and 180, respectively, in order of appearance)

| Antibody | VH CDR1 | | | | | P03(OD) | rsCD14ST-Fc(OD) |
|---|---|---|---|---|---|---|---|
| S68 Antibody | | | | | | | 1.0 |
| F1466-26 | R | Y | T | M | G | 2.314 | 4.9 |
| 5932 | M | | | | | 2.194 | 4.3 |
| 5933 | P | | | | | 2.244 | 4.8 |
| 5934 | V | | | | | 2.281 | 5.1 |
| 5935 | I | | | | | 2.237 | 5.0 |
| 5937 | D | | | | | 2.200 | 4.5 |
| 5938 | E | | | | | 2.221 | 4.5 |
| 5939 | H | | | | | 2.207 | 5.0 |
| 5940 | T | | | | | 2.199 | 4.8 |
| 5941 | Q | | | | | 2.257 | 4.0 |
| 5942 | Y | | | | | 2.252 | 4.9 |
| 5943 | G | | | | | 2.253 | 4.6 |
| 5944 | K | | | | | 2.258 | 5.0 |
| 5945 | N | | | | | 2.177 | 4.1 |
| 5946 | W | | | | | 2.214 | 4.5 |
| 5804 | D | | A | L | N | 0.033 | 1.1 |

TABLE 26

Heavy chain CDR3 of modified region
(SEQ ID NOS 170, 186-188, 124, 189-192, 125, 193-195, and 140-153, respectively, in order of appearance)

| Antibody | VH CDR3 | | | P03(OD) | rsCD14ST-Fc(OD) |
|---|---|---|---|---|---|
| S68 Antibody | | | | | 1.0 |
| F1466-26 | G | D | F | 2.314 | 4.9 |
| 5912 | T | | | 0.027 | 0.3 |
| 5914 | Q | | | 1.345 | 1.7 |
| 5918 | E | | | 0.023 | 0.2 |
| 5920 | L | | | 1.498 | 3.1 |
| 5921 | M | | | 0.853 | 3.8 |
| 5922 | P | | | 0.038 | 0.2 |
| 5923 | W | | | 1.235 | 0.4 |
| 5924 | Y | | | 0.204 | 2.7 |
| 5926 | S | | | 2.301 | 4.4 |
| 5927 | V | | | 0.036 | 0.2 |
| 5928 | D | | | 0.033 | 0.2 |
| 5929 | R | | | 2.130 | 0.9 |
| 5976 | | F | | 2.204 | 4.7 |
| 5977 | | S | | 2.241 | 4.7 |
| 5978 | | P | | 2.288 | 4.6 |
| 5979 | | H | | 2.309 | 5.5 |
| 5980 | | I | | 2.293 | 5.3 |
| 5981 | | N | | 2.289 | 4.4 |
| 5982 | | R | | 2.251 | 4.7 |
| 5983 | | | S | 2.287 | 5.5 |
| 5984 | | | P | 2.186 | 5.1 |
| 5985 | | | H | 2.317 | 4.9 |
| 5986 | | | D | 2.346 | 4.4 |
| 5987 | | | I | 2.357 | 5.2 |
| 5988 | | | N | 2.337 | 5.6 |
| 5989 | | | R | 2.342 | 4.5 |

TABLE 11

Heavy chain CDR2 of modified region
(SEQ ID NOS 169, 104-108, 181, and 109-111, respectively, in order of appearance)

| Antibody | VH CDR2 | | | | | | | | | | | | | P03(OD) | rsCD14ST-Fc(OD) |
|---|---|---|---|---|---|---|---|---|---|---|---|---|---|---|---|
| S68 Antibody | | | | | | | | | | | | | | | 1.0 |
| F1466-26 | I | I | N | S | G | A | T | Y | Y | A | S | W | A | K | G | 2.314 | 4.9 |
| 5807 | | | | | | | | | | A | | | | | | 2.253 | 4.3 |
| 5808 | | | | | | | | | | | A | | | | | 2.267 | 5.3 |
| 5809 | | | | | | | | | | | | | A | | | 2.296 | 5.1 |
| 5812 | | | | | | | | | | | | | | | G | 2.269 | 4.5 |
| 5824 | | | | VSSD | | | | G | I | | | | | | | 2.269 | 5.3 |
| 5825 | | | | YAGG | | | | S | | | | | | | | 0.028 | 0.5 |
| 5826 | | | | YRNIK | | | | | T | | | | | | | 2.277 | 4.4 |
| 5827 | | | | SDIDQIV | | | | | T | | | | | | | 1.849 | 4.2 |
| 5841 | | | | SDIDDLF | | | | | | | | | | | | 2.169 | 4.3 |

TABLE 13

Light chain CDR1 of modified region
(SEQ ID NOS 172, 114-115, 120, 119, 122, 196, and 123, respectively,
in order of appearance)

| Antibody | | | | VL CDR1 | | | | | | | P03(OD) | rsCD14ST-Fc(OD) |
|---|---|---|---|---|---|---|---|---|---|---|---|---|
| S68 | | | | | | | | | | | | 1.0 |
| Antibody F1466-26 | Q | A | S | Q | S | I | G | S | N | L | A | 2.314 | 4.9 |
| 5859 | | A | | | | | | | | | | 2.282 | 4.6 |
| 5860 | | | G | | | | | | | | | 2.248 | 5.2 |
| 5865 | A | | | | | | | | | | | 2.276 | 4.7 |
| 5864 | | | | | | | | | A | | | 2.253 | 5.7 |
| 5884 | | | | | E | D | I | | | | | 2.221 | 4.7 |
| 5885 | | | | | E | R | | R | N | W | S | 1.549 | 3.8 |
| 5910 | | | | | | N | | | D | | S | 2.129 | 4.2 |

TABLE 14

Light chain CDR2 of modified region
(SEQ ID NOS 173, 117-118, and 121, respectively,
in order of appearance)

| Antibody | | | VL CDR2 | | | | P03(OD) | rsCD14ST-Fc(OD) |
|---|---|---|---|---|---|---|---|---|
| S68 | | | | | | | | 1.0 |
| Antibody F1466-26 | K | A | S | K | L | A | S | 2.314 | 4.9 |
| 5862 | | | | | A | | | 2.211 | 4.4 |
| 5863 | | | A | | | | | 2.241 | 5.2 |
| 5877 | | | | | T | | | 2.210 | 4.6 |

TABLE 15

Light chain CDR3 of modified region
(SEQ ID NOS 174, 112-113, 116, and 197-200, respectively,
in order of appearance)

| Antibody | | | | | VL CDR3 | | | | | | | | | P03(OD) | rsCD14ST-Fc(OD) |
|---|---|---|---|---|---|---|---|---|---|---|---|---|---|---|---|
| S68 | | | | | | | | | | | | | | | 1.0 |
| Antibody F1466-26 | Q | C | S | Y | T | A | I | G | N | Y | G | H | V | 2.314 | 4.9 |
| 5842 | | | | | | | | | | | | A | | 2.313 | 4.7 |
| 5843 | | | | | | | | | | | A | | | 2.290 | 4.7 |
| 5861 | A | | | | | | | | | | | | | 2.235 | 4.5 |
| 5880 | | S | Y | | G | G | | S | S | L | Y | N | I | 0.036 | 0.2 |
| 5882 | | | | | | G | | | | A | | N | A | 0.023 | 0.2 |
| 5905 | | S | T | | YRSTTT | | | | | | | N | | 0.031 | 0.2 |
| 5907 | L | G | V | V | G | S | T | S | D | D | | F | A | 0.019 | 0.2 |

Example 11: Preparation of Monoclonal Antibody Using Phage Display Method which Uses Synthetic Peptide as Antigen With regard to Example 1-(1), by using lymphocytes which are collected from a rabbit immunized with the S68 peptide-KLH as an antigen for administration, a monoclonal antibody is prepared according to a phage display method.

11-(1) Establishment of Immuno F(Ab) Phage Library

According to the method described by CARLOS F. BARBAS III, et. al, Phage Display A Laboratory Manual (Cold Spring Harbor Laboratory Press), total RNA is extracted from the lymphocytes derived from spleen which have been collected from Example 1-(1) by using TRIZOL® Reagent (Life Technologies). Then, by using SuperScript SUPERSCRIPT™ III First-Strand Synthesis System for RT-PCR (Life Technologies), a single stranded cDNA is synthesized. From this cDNA, by using a primer specific to rabbit antibody gene reported by BARBAS III, et al., a fragment containing the heavy chain variable region and a fragment containing the light chain variable region are prepared. By using amplified fragments of the obtained rabbit heavy chain variable region and human heavy chain CH1 as a template, rabbit/human chimeric heavy chain fragment is amplified by PCR. Further, by using amplified fragments of the rabbit light chain variable region (kappa type or lambda type) and human light chain constant region as a template, the rabbit/human chimeric light chain fragment is amplified. By using these fragments obtained rabbit/human chimeric heavy chain and rabbit/human chimeric light chain as a template, the rabbit/human chimeric Fab fragment is finally prepared.

Next, according to digestion of pCDisplay-4 (Creative Biogene), which is a phagemid for antibody expression, with restriction enzymes SacI and SpeI, a phagemid is prepared. Similarly, according to digestion of the rabbit/human chimeric Fab fragment with SacI and SpeI and insertion of the cDNA fragment into the thus-prepared phagemid fragment, a plasmid for expressing phage library is prepared.

11-(2) Preparation of Phage Solution for Phage Display

By following a common method, E. Coli TG1 strain (Alient Technologies) is transformed with the plasmid which has been prepared in 11-(1), and the solution containing the E. Coli is inoculated to an LB medium plate added with ampicillin. After culture at 37° C., the formed colonies are collected to prepare the E. Coli library. Part of the library is cultured and, after adding ampicillin and glucose to a suspension of E. Coli, it is cultured under shaking for one hour at 37° C. After that, it is transfected with the helper phage M13KO7 (Life Technologies) and culture under shaking is again continued for one hour. The cells are collected by centrifuge, and after removing the culture solution, they are suspended in 10 ml of 2×YT culture solution followed by culture under shaking at 37° C. On the next day, the culture supernatant is separated by centrifuge and 8 mL of the supernatant is transferred to another tube. After adding 2 mL of PEG/NaCl solution followed by mixing, it is kept on ice for one hour. Then, the precipitated phage is collected by centrifuge and used as a phage solution for phage display.

Selection of Target Antibody by Panning Method

From a phage solution prepared from 11-(2), an antibody is selected by a panning method. Panning is performed according to two kinds of method. The first method is performed according to the method by BARBAS et. al. Specifically, S68-BSA is immobilized in a solid state on IMMUNO PLATE (MAXISORP, C96, 430341) manufactured by Nunc, followed by blocking. After adding, in an amount of 50 μL per well, D-PBS containing 4% skim milk and 0.2% TRITON® X-100, 50 μL of the phage solution obtained from 11-(2) is added thereto. The reaction is allowed to occur in the plate for one hour. Subsequently, it is washed with D-PBS containing 0.1% TRITON® X-100. Next, the elution is made for 10 minutes by using 100 mM Glycine-HCl (pH 2.2) and the recovered solution is neutralized with 1 M Tris-HCl (pH 7.4). The eluate and the *E. Coli* TG1 strain are admixed with each other and reacted at 37° C. The TG1 strain is transfected again with the phage bound to S68 peptide antigen. To the culture solution, Ampicillin and M13K07 helper phage are added. After reacting them at 37° C., *E. Coli* is collected to add a medium and kanamycin thereto, and cultured overnight. From the culture solution, the supernatant is collected by centrifuge and the phage solution is prepared by a PEG treatment. By repeating three times the same procedure, a phage specifically binding to S68 peptide is concentrated. As the second method, the panning is also performed three times using the method described in Example 12-(2) to concentrate the phage specific to presepsin.

11-(4) Measurement of Binding Activity of Antibody and Interpretation of CDR Sequence The TG1 culture solution of 11-(3), which is transfected with the phage, is inoculated to an LB plate containing Ampicillin to form a colony. From each colony, a phage solution is prepared again and the reactivity is determined by ELISA. Specifically, each of BSA, S68-BSA, P03-BSA and sCD14ST-Fc is immobilized on IMMUNO PLATE (MAXISORP, C96, 430341) manufactured by Nunc, followed by blocking. After adding D-PBS containing 4% skim milk and 0.2% TRITON® X-100, collected phage solution is added thereto. The reaction is allowed to occur in the plate for one hour. Subsequently, the plate is washed five times with physiological saline containing 0.05% TWEEN®20. Next, a solution in which HRP/Anti-M13 Monoclonal Conjugate (GE Healthcare) is diluted, is added to each well and the reaction is allowed to occur for one hour at room temperature. Similarly, after washing the plate five times, a TMB solution is added and the reaction is allowed to occur for 10 to 20 minutes at room temperature. When the reaction is completed, the reaction is terminated by using a 1 M sulfuric acid solution. The absorbance at 450/650 nm is measured by using a plate reader (THERMOMAX™, Molecular Devices). As a result, the binding is confirmed from several kinds of the phage. From those colonies, the phagemid is isolated and the sequence is determined. According to the phage display method, an anti presepsin antibody which specifically binds to P03 and presepsin and is a sequence different from the CDR sequence obtained by a hybridoma method is obtained.

Example 12: Preparation of Variant of Heavy Chain CDR3 Sequence Using Phage Display Method Because the heavy chain CDR3 sequence is expected to have an effect on an enzyme activity, a variant of heavy chain CDR3 sequence was prepared by using a phage display method and evaluated.

12-(1) Preparation of Variant Modified of VH Chain CDR3 Sequence Using Phage Display Method To prepare VH CDR3 random mutation library, PCR was performed by using plasmid pTK-5956 containing the heavy chain and light chain of F1466-26 as a template, a pair of primers (p-nnk3-2s; 5' phosphorylated-GGT NNK NNK NNK TGG GGC CAA GGC ACC CTG GTC ACC GTC T-3'(SEQ ID NO:91), p-nnk3-2a; 5' phosphorylated-GCC ACA AAA ATA AGT GGC CGT GTC CTC GGT TGT CGG ACT G-3'(SEQ ID NO:92) (N represents any one of G, A, T, and C, and K represents G or T)), and a heat resistant DNA polymerase (TAKARA BIO INC.). The amplified fragment obtained therefrom was self-ligated by using DNA ligase. The resultant was transformed into *E. coli* XL1-BLUE® (Agilent Technologies) and cultured on an agar plate containing LB/Ampicillin/Tetracycline. On the next day, the generated colonies were collected by using 2×YT culture solution. To the *E. Coli* suspension, Ampicillin, tetracycline, and glucose were added and culture was performed for one hour at 37° C. under shaking. After that, it was transfected with the helper phage M13KO7 (Life Technologies) and culture under shaking was again continued for one hour. The cells were collected by centrifuge, and after removing the culture solution, they were suspended in 10 ml of 2×YT culture solution followed by culture under shaking at 32° C. On the next day, the culture supernatant was separated by centrifuge and 8 mL of the supernatant was transferred to another tube. After adding 2 mL of PEG/NaCl solution followed by mixing, it was kept on ice for one hour. Then, the precipitated phage was collected by centrifuge and used as a phage solution of VH CDR3 random mutation library.

12-(2) Selection of Target Antibody by Panning Method

With the library prepared in 12-(1), panning was performed to select an antibody. Specifically, the phage solution (2 mL) obtained from 12-(1) and 6 μg of sCD14ST-Fc were reacted at 37° C. Two hours later, 200 μL of protein A resin (PROSEP®-vA, MERCK MILLIPORE®) was added thereto followed by reaction for 20 minutes. After washing five times with PBS containing 0.05% TWEEN®20, the resin was added with an eluent (Tris-HCl, Glycine (pH 2.2)) and maintained for 8 minutes. Then, the eluted phage solution was collected and the solution was neutralized. The collected solution and the culture solution of *E. coli* XL1-BLUE® were admixed with each other and reacted at 37° C. One hour later, L-glutamine, Ampicillin and helper phage M13K07 (INVITROGEN®) were added thereto and the reaction was allowed to occur at 37° C. Again, one hour later, the medium was replaced with a 2×YT medium followed by culture overnight. Thus, phages specifically bound to rsCD14ST-Fc were collected. By repeating three times the same procedure, a target antibody was concentrated.

12-(3) Preparation of Phage Containing Presepsin-Specific Sequence and Determination of CDR Sequence XL1-BLUE® was transfected again with the phage solution finally obtained in 12-(2) and the culture supernatant was inoculated in a 2×YT medium to prepare a colony. The resulting colony was cultured again with XL1-BLUE® and, by adding a helper phage, a phage solution containing single phage was prepared. Next, by using the obtained phage solution, the reactivity was confirmed based on ELISA. Specifically, sCD14ST-Fc was immobilized on a plate, that is, IMMUNO PLATE (MAXISORP, C96, 430341) manufactured by Nunc, followed by blocking. The phage solution was diluted (×2) by using D-PBS containing 4% skim milk and 0.2% Triton®X-100 and the reaction was allowed to occur in the plate for one hour. Subsequently, the plate was washed five times with physiological saline containing 0.05% TWEEN®20. Next, a solution in which HRP/Anti-M13 Monoclonal Conjugate (GE Healthcare) is diluted was added in an amount of 50 µL per well and the reaction was allowed to occur for one hour at room temperature. Similarly, after washing the plate five times, a TMB solution was added and the reaction was allowed to occur at room temperature. When the reaction is completed, the reaction was terminated by using a 1 M sulfuric acid solution. The absorbance at 450/650 nm was measured by using a plate reader (THERMOMAX™, Molecular Devices). Then, *E. coli* was transfected with the phage solution with confirmed binding activity, and after collecting the plasmid according to a common method, the gene sequence was determined.

12-(4) Preparation of IgG Antibody

The phagemid was collected from the obtained candidate phages, and a fragment encoding the variable region of the heavy chain was prepared. According to the method described in Example 8, a plasmid for preparing a heavy chain variant was prepared. It was then used for transfection of COS-1 cells, together with the plasmid (pTK-5608) for transient expression of light chain containing the entire length of light chain of the F1466-26. The COS-1 cells were cultured at 37° C. Seventy-two hours later, the culture supernatant was collected.

12-(5) Evaluation of Variant of Heavy Chain CDR3 Sequence

The obtained variant was subjected to the same test as Example 10-(2) so as to evaluate the binding activity for presepsin (rsCD14ST-Fc) and P03 specificity. The results are shown in Table 30, together with the CDR sequence of the modified heavy chain CDR3.

As a result, the variant 6027 in which 3 amino acids of the heavy chain CDR3 have been substituted exhibited slightly lower reactivity for presepsin compared to other variants. However, when compared to the S68 antibody, it exhibited almost the same reactivity. The variants 6026, 6028, and 6029 exhibited excellent reactivity for presepsin even though two amino acids have been substituted. Based on these results, it was demonstrated that the antibody activity may be possibly maintained even when the heavy chain CDR3 is composed of three amino acids and the two amino acids thereof are substituted. Variant 6028 showed a particularly excellent binding activity for presepsin.

TABLE 30

Heavy chain CDR3 of modified region
(SEQ ID NOS 170, 154, 201, and 155-156, respectively, in order of appearance)

| Antibody | VH CDR3 | | | P03(OD) | rsCD14ST-Fc(OD) |
|---|---|---|---|---|---|
| S68 Antibody | | | | | 1.0 |
| F1466-26 | G | D | F | 1.516 | 4.9 |
| 6026 | | V | L | 1.542 | 4.6 |
| 6027 | S | N | C | 1.382 | 0.9 |
| 6028 | | G | E | 1.531 | 5.5 |
| 6029 | | L | H | 1.576 | 5.1 |

Example 13: Triglyceride (TG) interference test

According to Example 5 and Example 6, it has been demonstrated that the presepsin measurement using an antibody which recognizes P04-05 as an epitope is easily interfered by TG in a sample but the presepsin measurement using an antibody which recognizes P03 as an epitope is hardly interfered by TG.

13-(1) TG Interference Test (1) Using Blood Serum from Normal Human

For further confirmation, an influence of TG on a normal test sample was determined. TG interference test was performed for F1466-26 (specificity:P03), F1466-5 (P03), and F1466-19 (P04-05) by using blood serum from a normal human.

Figure 1B:
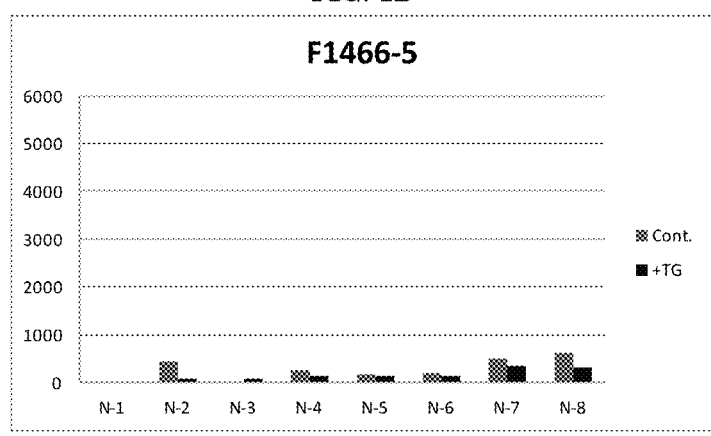
Figure 1C:
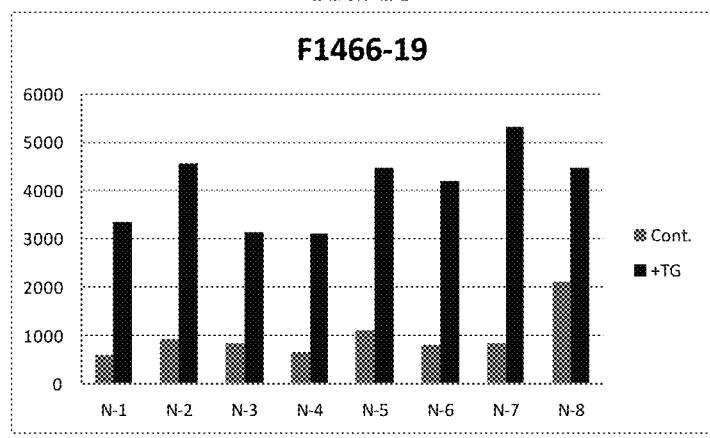

To the test sample from normal human (8 samples) (EDTA blood plasma, TENECEE BLOOD SERVICIES), TG was added to final concentration of 10 mg/mL and the presepsin measurement value was compared before and after the addition. With regard to the TG concentration at that time, the TG originally included in the test sample was not taken into consideration. Evaluation was made by using a plate in which each antibody is immobilized in a solid state and the sandwich ELISA system described in Example 9-(3). The results are shown in FIGS. 1A-1C.

As a result, the antibodies F1466-26 and F1466-5 which recognize P03 as an epitope exhibited almost no change in the measurement value before and after the addition of TG. However, the measurement value from the antibody F1466-19 which recognizes P04-05 as an epitope was significantly affected by the addition of TG. It is expected that, like F1466-19, the measurement using an antibody in which the presepsin measurement value is significantly affected by TG present in a test sample exhibits a high measurement value for a healthy person who normally shows a low value. In that case, it is difficult to have a difference between a normal value and an abnormal value. Thus, it can be said that such antibody is not suitable for measurement of presepsin in a test sample. Meanwhile, it was confirmed that the antibody which recognizes P03 as an epitope is hardly affected by TG present in a test sample, and thus it is an antibody suitable for measurement of presepsin present in a test sample.

In addition, a test using this normal person human serum supports that a cross reaction with high molecular weight sCD14 is negligible in an assay system using an antibody recognizing P03 as an epitope.

In normal person human serum, presepsin is a few hundreds of pg/mL, while high molecular weight sCD14 is present at around 5.6 to 11.2 μg/mL (WO 2005/108429, Example 12), and if the antibody reacts with high molecular weight sCD14, it is impossible to measure a minor amount of presepsin.

According to the present Example, it was confirmed that, in an assay system using an antibody recognizing P03 as an epitope, a cross reaction with high molecular weight sCD14 is not caused, and it is possible to measure presepsin at a minor amount of around a few hundreds of pg/mL.

13-(2) TG Interference Test (2) Using Variant

The TG interference test was performed in the same manner as Example 5 for the newly obtained variants and the influence of TG present in the test sample was determined. The variant was used after purification.

Specifically, the variant was immobilized on IMMUNO PLATE (MAXISORP, C96, 430341) manufactured by Nunc followed by blocking. Dilution of a presepsin standard was made by using a dilution solution to prepare presepsin concentration series (15.6 to 500 pg/mL). To three kinds of human test sample, triglyceride (INTRALIPID®, manufactured by Fresenius Kabi Japan) was added to have final concentration of 6.7, 13.3, or 20 mg/mL. As for the human test sample, one test sample of blood serum obtained from a patient with sepsis and two test samples of blood serum obtained from a normal person, which have been further added with a certain amount of presepsin, were used. Further, TG originally contained in a test sample was not considered for the TG concentration. The test sample was diluted (×20) by using a dilution solution, and a sample not added with TG or added with TG at each concentration or a dilution series of a standard were added to each well. The measurement was carried out by using sandwich ELISA like Example 9-(3). The ratio (%) of the test sample which exhibits dissociation rate of ±20% or less for presepsin measurement when TG concentration is 30 mg/mL in a test sample was shown in Table 31.

As a result, it was confirmed that the antibody recognizing P03 as an epitope is hardly affected by triglyceride.

TABLE 31

| Antibody | Epitope | Modified region | Ratio (%) of test sample with dissociation rate of ±20% or less |
|---|---|---|---|
| 5793 | P03 | CDR3 | 100 |
| 5795 | P03 | CDR1 | 100 |
| 5810 | P03 | CDR2 | 100 |
| 5803 | P03 | CDR1 | 100 |
| 5811 | P03 | CDR1 | 100 |
| 5826 | P03 | CDR2 | 100 |
| 5942 | P03 | CDR1 | 100 |
| 5945 | P03 | CDR1 | 100 |

Example 14: List of Modified Products with Desirable Properties

The CDR sequence of antibodies with desirable properties, which have been obtained from Examples 8 and 12 of the present invention, is shown in FIGS. 2A-2E (SEQ ID NO.: 93 to SEQ ID NO.:156). The total number of antibodies prepared in Examples 8 and 12 was 109 and the number of preferred antibodies was 65.

The antibodies having affinity for presepsin (KD value) of less than $10^{-8}$ M were evaluated as ○ and the antibodies having the affinity of less than $10^{-9}$ M was evaluated as ⊚. The antibodies having a KD value of less than $10^{-7}$ M but exhibiting the affinity almost equivalent to the affinity for S68 antibody presepsin were evaluated as Δ. According to the evaluation of KD value, the antibodies found to have particularly excellent binding activity for presepsin were variants 5793 and 5810.

The binding activity for presepsin was evaluated by the ratio of absorbance obtained in the reaction between each antibody and rsCD14ST-Fc against absorbance obtained in the reaction between S68 antibody and rsCD14ST-Fc, when the absorbance obtained in the reaction between S68 antibody and rsCD14ST-Fc is set at 1. The antibody with the absorbance ratio of 4 or more was evaluated as ○ and the antibody with the absorbance ratio of 5.5 or more was evaluated as ⊚. According to the evaluation based on the absorbance comparison, the antibody found to have a particularly excellent binding activity for presepsin was variant 5864, 5979, 5983, 5988, and 6028.

What we claimed is:

1. An anti-presepsin monoclonal antibody or an antigen-binding antibody fragment thereof, wherein the antibody or the fragment specifically binds to an epitope of presepsin consisting of SEQ ID NO: 1.

2. The antibody or the antigen-binding antibody fragment thereof according to claim 1, wherein the fragment is an antigen-binding antibody fragment selected from the group consisting of Fab, Fab', F (ab')2, single-stranded antibody (scFv), dimerized V region (diabody), disulfide-stabilized V region (dsFv), and sc (Fv)2.

* * * * *

SEQUENCE LISTING

```
<160> NUMBER OF SEQ ID NOS: 231

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Arg Val Asp Ala Asp Ala Asp Pro Arg
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2
```

Arg Val Asp Ala Asp Ala Asp Pro Arg Gln Tyr Ala Asp Thr Val Lys
1               5                   10                  15

<210> SEQ ID NO 3
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Thr Thr Pro Glu Pro Cys Glu Leu Asp Asp Glu Asp Phe Arg Cys Val
1               5                   10                  15

Cys Asn Phe Ser Glu Pro Gln Pro Asp Trp Ser Glu Ala Phe Gln Cys
                20                  25                  30

Val Ser Ala Val Glu Val Glu Ile His Ala Gly Gly Leu Asn Leu Glu
            35                  40                  45

Pro Phe Leu Lys Arg Val Asp Ala Asp Ala Asp Pro Arg Gln Tyr Ala
        50                  55                  60

Asp Thr Val Lys Ala Leu Arg Val Arg Arg Leu Thr Val Gly Ala Ala
65                  70                  75                  80

Gln Val Pro Ala Gln Leu Leu Val Gly Ala Leu Arg Val Leu Ala Tyr
                85                  90                  95

Ser Arg Leu Lys Glu Leu Thr Leu Glu Asp Leu Lys Ile Thr Gly Thr
            100                 105                 110

Met Pro Pro Leu Pro Leu Glu Ala Thr Gly Leu Ala Leu Ser Ser Leu
        115                 120                 125

Arg Leu Arg Asn Val Ser Trp Ala Thr Gly Arg Ser Trp Leu Ala Glu
130                 135                 140

Leu Gln Gln Trp Leu Lys Pro Gly Leu Lys Val Leu Ser Ile Ala Gln
145                 150                 155                 160

Ala His Ser Pro Ala Phe Ser Cys Glu Gln Val Arg Ala Phe Pro Ala
                165                 170                 175

Leu Thr Ser Leu Asp Leu Ser Asp Asn Pro Gly Leu Gly Glu Arg Gly
            180                 185                 190

Leu Met Ala Ala Leu Cys Pro His Lys Phe Pro Ala Ile Gln Asn Leu
        195                 200                 205

Ala Leu Arg Asn Thr Gly Ile Glu Thr Pro Thr Gly Val Cys Ala Ala
210                 215                 220

Leu Ala Ala Ala Gly Val Gln Pro His Ser Leu Asp Leu Ser His Asn
225                 230                 235                 240

Ser Leu Arg Ala Thr Val Asn Pro Ser Ala Pro Arg Cys Met Trp Ser
                245                 250                 255

Ser Ala Leu Asn Ser Leu Asn Leu Ser Phe Ala Gly Leu Glu Gln Val
            260                 265                 270

Pro Lys Gly Leu Pro Ala Lys Leu Arg Val Leu Asp Leu Ser Cys Asn
        275                 280                 285

Arg Leu Asn Arg Ala Pro Gln Pro Asp Glu Leu Pro Glu Val Asp Asn
290                 295                 300

Leu Thr Leu Asp Gly Asn Pro Phe Leu Val Pro Gly Thr Ala Leu Pro
305                 310                 315                 320

His Glu Gly Ser Met Asn Ser Gly Val Val Pro Ala Cys Ala Arg Ser
                325                 330                 335

Thr Leu Ser Val Gly Val Ser Gly Thr Leu Val Leu Leu Gln Gly Ala

```
                    340                 345                 350
Arg Gly Phe Ala
        355

<210> SEQ ID NO 4
<211> LENGTH: 5
<212> TYPE: PRT
<213> ORGANISM: Oryctolagus cuniculus

<400> SEQUENCE: 4

Arg Tyr Ala Met Gly
1               5

<210> SEQ ID NO 5
<211> LENGTH: 16
<212> TYPE: PRT
<213> ORGANISM: Oryctolagus cuniculus

<400> SEQUENCE: 5

Ile Ile Tyr Arg Asn Ile Lys Thr Tyr Tyr Ala Thr Trp Ala Lys Gly
1               5                   10                  15

<210> SEQ ID NO 6
<211> LENGTH: 3
<212> TYPE: PRT
<213> ORGANISM: Oryctolagus cuniculus

<400> SEQUENCE: 6

Gly Asp Phe
1

<210> SEQ ID NO 7
<211> LENGTH: 5
<212> TYPE: PRT
<213> ORGANISM: Oryctolagus cuniculus

<400> SEQUENCE: 7

Arg Tyr Thr Met Gly
1               5

<210> SEQ ID NO 8
<211> LENGTH: 15
<212> TYPE: PRT
<213> ORGANISM: Oryctolagus cuniculus

<400> SEQUENCE: 8

Ile Ile Asn Ser Gly Ala Thr Tyr Tyr Ala Ser Trp Ala Lys Gly
1               5                   10                  15

<210> SEQ ID NO 9
<211> LENGTH: 3
<212> TYPE: PRT
<213> ORGANISM: Oryctolagus cuniculus

<400> SEQUENCE: 9

Gly Asp Phe
1

<210> SEQ ID NO 10
<211> LENGTH: 5
<212> TYPE: PRT
<213> ORGANISM: Oryctolagus cuniculus

<400> SEQUENCE: 10
```

Ser Phe Trp Met Ser
1               5

<210> SEQ ID NO 11
<211> LENGTH: 16
<212> TYPE: PRT
<213> ORGANISM: Oryctolagus cuniculus

<400> SEQUENCE: 11

Ile Ile Ser Asp Ile Asp Asp Leu Phe Tyr Ala Ser Trp Ala Lys Gly
1               5                   10                  15

<210> SEQ ID NO 12
<211> LENGTH: 3
<212> TYPE: PRT
<213> ORGANISM: Oryctolagus cuniculus

<400> SEQUENCE: 12

Gly Gly Leu
1

<210> SEQ ID NO 13
<211> LENGTH: 5
<212> TYPE: PRT
<213> ORGANISM: Oryctolagus cuniculus

<400> SEQUENCE: 13

Ser Tyr Asp Met Ile
1               5

<210> SEQ ID NO 14
<211> LENGTH: 16
<212> TYPE: PRT
<213> ORGANISM: Oryctolagus cuniculus

<400> SEQUENCE: 14

Tyr Ile Gly Ser Pro Gly Thr Thr Tyr Tyr Gly Ser Trp Ala Lys Gly
1               5                   10                  15

<210> SEQ ID NO 15
<211> LENGTH: 10
<212> TYPE: PRT
<213> ORGANISM: Oryctolagus cuniculus

<400> SEQUENCE: 15

Ser Gly Asp Ile Thr Asn Arg Phe Asn Leu
1               5                   10

<210> SEQ ID NO 16
<211> LENGTH: 5
<212> TYPE: PRT
<213> ORGANISM: Oryctolagus cuniculus

<400> SEQUENCE: 16

Asn Tyr Asp Met Ile
1               5

<210> SEQ ID NO 17
<211> LENGTH: 16
<212> TYPE: PRT
<213> ORGANISM: Oryctolagus cuniculus

<400> SEQUENCE: 17

Tyr Ile Gly Ser Pro Gly Thr Thr Tyr Tyr Ala Ser Trp Ala Lys Gly
1               5                   10                  15

```
<210> SEQ ID NO 18
<211> LENGTH: 10
<212> TYPE: PRT
<213> ORGANISM: Oryctolagus cuniculus

<400> SEQUENCE: 18

Ser Gly Asp Ile Thr Asn Arg Phe Asn Leu
1               5                   10

<210> SEQ ID NO 19
<211> LENGTH: 11
<212> TYPE: PRT
<213> ORGANISM: Oryctolagus cuniculus

<400> SEQUENCE: 19

Gln Ala Ser Glu Asp Ile Ile Ser Asn Leu Ala
1               5                   10

<210> SEQ ID NO 20
<211> LENGTH: 7
<212> TYPE: PRT
<213> ORGANISM: Oryctolagus cuniculus

<400> SEQUENCE: 20

Lys Ala Ser Thr Leu Ala Ser
1               5

<210> SEQ ID NO 21
<211> LENGTH: 13
<212> TYPE: PRT
<213> ORGANISM: Oryctolagus cuniculus

<400> SEQUENCE: 21

Gln Ser Ser Tyr Thr Glu Ser Thr Thr Phe Gly His Val
1               5                   10

<210> SEQ ID NO 22
<211> LENGTH: 11
<212> TYPE: PRT
<213> ORGANISM: Oryctolagus cuniculus

<400> SEQUENCE: 22

Gln Ala Ser Gln Ser Ile Gly Ser Asn Leu Ala
1               5                   10

<210> SEQ ID NO 23
<211> LENGTH: 7
<212> TYPE: PRT
<213> ORGANISM: Oryctolagus cuniculus

<400> SEQUENCE: 23

Lys Ala Ser Lys Leu Ala Ser
1               5

<210> SEQ ID NO 24
<211> LENGTH: 13
<212> TYPE: PRT
<213> ORGANISM: Oryctolagus cuniculus

<400> SEQUENCE: 24

Gln Cys Ser Tyr Thr Ala Ile Gly Asn Tyr Gly His Val
1               5                   10
```

<210> SEQ ID NO 25
<211> LENGTH: 11
<212> TYPE: PRT
<213> ORGANISM: Oryctolagus cuniculus

<400> SEQUENCE: 25

Gln Ala Ser Gln Ser Ile Ser Asn Tyr Leu Ala
1               5                   10

<210> SEQ ID NO 26
<211> LENGTH: 7
<212> TYPE: PRT
<213> ORGANISM: Oryctolagus cuniculus

<400> SEQUENCE: 26

Lys Thr Ser Thr Leu Glu Ser
1               5

<210> SEQ ID NO 27
<211> LENGTH: 14
<212> TYPE: PRT
<213> ORGANISM: Oryctolagus cuniculus

<400> SEQUENCE: 27

Gln Ser Thr Tyr Tyr Arg Ser Thr Thr Thr Tyr Gly Asn Thr
1               5                   10

<210> SEQ ID NO 28
<211> LENGTH: 11
<212> TYPE: PRT
<213> ORGANISM: Oryctolagus cuniculus

<400> SEQUENCE: 28

Gln Ala Ser Glu Arg Ile Arg Asn Trp Leu Ser
1               5                   10

<210> SEQ ID NO 29
<211> LENGTH: 7
<212> TYPE: PRT
<213> ORGANISM: Oryctolagus cuniculus

<400> SEQUENCE: 29

Arg Ala Ser Thr Leu Glu Ser
1               5

<210> SEQ ID NO 30
<211> LENGTH: 11
<212> TYPE: PRT
<213> ORGANISM: Oryctolagus cuniculus

<400> SEQUENCE: 30

Gln Cys Ser Ala Gly Gly Asn Ala Gly Asn Ala
1               5                   10

<210> SEQ ID NO 31
<211> LENGTH: 11
<212> TYPE: PRT
<213> ORGANISM: Oryctolagus cuniculus

<400> SEQUENCE: 31

Gln Ala Ser Glu Arg Ile Arg Asn Trp Leu Ser
1               5                   10

<210> SEQ ID NO 32
<211> LENGTH: 7

```
<212> TYPE: PRT
<213> ORGANISM: Oryctolagus cuniculus

<400> SEQUENCE: 32

Arg Ala Ser Thr Leu Glu Ser
1               5

<210> SEQ ID NO 33
<211> LENGTH: 11
<212> TYPE: PRT
<213> ORGANISM: Oryctolagus cuniculus

<400> SEQUENCE: 33

Gln Cys Ser Ala Gly Gly Asn Ala Gly Asn Gly
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Cys Gly Asp Lys Thr Thr Ala Thr Asp Ile Lys Gly Lys Glu
1               5                   10

<210> SEQ ID NO 35
<211> LENGTH: 10
<212> TYPE: PRT
<213> ORGANISM: Homo sapiens

<400> SEQUENCE: 35

Asn Leu Glu Pro Phe Leu Lys Arg Val Asp
1               5                   10

<210> SEQ ID NO 36
<211> LENGTH: 10
<212> TYPE: PRT
<213> ORGANISM: Homo sapiens

<400> SEQUENCE: 36

Pro Phe Leu Lys Arg Val Asp Ala Asp Ala
1               5                   10

<210> SEQ ID NO 37
<211> LENGTH: 10
<212> TYPE: PRT
<213> ORGANISM: Homo sapiens

<400> SEQUENCE: 37

Asp Ala Asp Ala Asp Pro Arg Gln Tyr Ala
1               5                   10

<210> SEQ ID NO 38
<211> LENGTH: 10
<212> TYPE: PRT
<213> ORGANISM: Homo sapiens

<400> SEQUENCE: 38

Ala Asp Pro Arg Gln Tyr Ala Asp Thr Val
1               5                   10

<210> SEQ ID NO 39
```

```
<211> LENGTH: 10
<212> TYPE: PRT
<213> ORGANISM: Homo sapiens

<400> SEQUENCE: 39

Arg Gln Tyr Ala Asp Thr Val Lys Ala Leu
1               5                   10

<210> SEQ ID NO 40
<211> LENGTH: 10
<212> TYPE: PRT
<213> ORGANISM: Homo sapiens

<400> SEQUENCE: 40

Ala Asp Thr Val Lys Ala Leu Arg Val Arg
1               5                   10

<210> SEQ ID NO 41
<211> LENGTH: 10
<212> TYPE: PRT
<213> ORGANISM: Homo sapiens

<400> SEQUENCE: 41

Val Lys Ala Leu Arg Val Arg Arg Leu Thr
1               5                   10

<210> SEQ ID NO 42
<211> LENGTH: 5
<212> TYPE: PRT
<213> ORGANISM: Rattus norvegicus

<400> SEQUENCE: 42

Asp Tyr Phe Met Asn
1               5

<210> SEQ ID NO 43
<211> LENGTH: 19
<212> TYPE: PRT
<213> ORGANISM: Rattus norvegicus

<400> SEQUENCE: 43

Gln Ile Arg Asn Lys Asn Tyr Asn Tyr Ala Thr Tyr Tyr Ala Glu Ser
1               5                   10                  15

Leu Glu Gly

<210> SEQ ID NO 44
<211> LENGTH: 4
<212> TYPE: PRT
<213> ORGANISM: Rattus norvegicus

<400> SEQUENCE: 44

Thr Phe Asp Cys
1

<210> SEQ ID NO 45
<211> LENGTH: 16
<212> TYPE: PRT
<213> ORGANISM: Rattus norvegicus

<400> SEQUENCE: 45

Arg Ser Ser Gln Ser Leu Val His Asn Asn Gly Asn Thr Tyr Leu Ser
1               5                   10                  15

<210> SEQ ID NO 46
```

```
<211> LENGTH: 7
<212> TYPE: PRT
<213> ORGANISM: Rattus norvegicus

<400> SEQUENCE: 46

Lys Val Ser Asn Arg Phe Ser
1               5

<210> SEQ ID NO 47
<211> LENGTH: 9
<212> TYPE: PRT
<213> ORGANISM: Rattus norvegicus

<400> SEQUENCE: 47

Gly Gln Gly Thr Gln Tyr Pro Tyr Thr
1               5

<210> SEQ ID NO 48
<211> LENGTH: 29
<212> TYPE: PRT
<213> ORGANISM: Oryctolagus cuniculus

<400> SEQUENCE: 48

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser
            20                  25

<210> SEQ ID NO 49
<211> LENGTH: 14
<212> TYPE: PRT
<213> ORGANISM: Oryctolagus cuniculus

<400> SEQUENCE: 49

Trp Val Arg Gln Ala Pro Gly Lys Gly Leu Glu Tyr Ile Gly
1               5                   10

<210> SEQ ID NO 50
<211> LENGTH: 30
<212> TYPE: PRT
<213> ORGANISM: Oryctolagus cuniculus

<400> SEQUENCE: 50

Arg Phe Thr Ile Ser Lys Thr Ser Ser Thr Thr Val Asp Leu Lys Ile
1               5                   10                  15

Thr Ser Pro Thr Thr Glu Asp Thr Ala Thr Tyr Phe Cys Val
            20                  25                  30

<210> SEQ ID NO 51
<211> LENGTH: 11
<212> TYPE: PRT
<213> ORGANISM: Oryctolagus cuniculus

<400> SEQUENCE: 51

Trp Gly Gln Gly Thr Leu Val Thr Val Ser Ser
1               5                   10

<210> SEQ ID NO 52
<211> LENGTH: 29
<212> TYPE: PRT
<213> ORGANISM: Oryctolagus cuniculus

<400> SEQUENCE: 52

Gln Ser Val Glu Gly Ser Arg Gly Arg Leu Val Thr Pro Gly Thr Pro
```

```
                1               5                  10                  15
Leu Thr Leu Thr Cys Thr Val Ser Gly Ile Asp Leu Asn
                20                  25
```

<210> SEQ ID NO 53
<211> LENGTH: 14
<212> TYPE: PRT
<213> ORGANISM: Oryctolagus cuniculus

<400> SEQUENCE: 53

```
Trp Val Arg Gln Ala Pro Gly Lys Gly Leu Glu Tyr Ile Gly
1               5                   10
```

<210> SEQ ID NO 54
<211> LENGTH: 31
<212> TYPE: PRT
<213> ORGANISM: Oryctolagus cuniculus

<400> SEQUENCE: 54

```
Arg Tyr Thr Ile Ser Lys Thr Ser Ser Thr Val Asp Leu Lys Leu
1               5                   10                  15

Thr Ser Pro Thr Thr Glu Asp Thr Ala Thr Tyr Phe Cys Ala Arg
                20                  25                  30
```

<210> SEQ ID NO 55
<211> LENGTH: 11
<212> TYPE: PRT
<213> ORGANISM: Oryctolagus cuniculus

<400> SEQUENCE: 55

```
Trp Gly Gln Gly Thr Leu Val Thr Val Ser Ser
1               5                   10
```

<210> SEQ ID NO 56
<211> LENGTH: 43
<212> TYPE: PRT
<213> ORGANISM: Oryctolagus cuniculus

<400> SEQUENCE: 56

```
Met Arg Ala Pro Thr Gln Leu Leu Gly Leu Leu Leu Leu Trp Leu Pro
1               5                   10                  15

Gly Ala Arg Cys Asp Val Val Met Thr Gln Thr Pro Ala Ser Val Glu
                20                  25                  30

Ala Ala Val Gly Gly Thr Val Thr Ile Lys Cys
            35                  40
```

<210> SEQ ID NO 57
<211> LENGTH: 15
<212> TYPE: PRT
<213> ORGANISM: Oryctolagus cuniculus

<400> SEQUENCE: 57

```
Trp Tyr Gln Gln Lys Pro Gly Gln Pro Pro Lys Leu Leu Ile Tyr
1               5                   10                  15
```

<210> SEQ ID NO 58
<211> LENGTH: 32
<212> TYPE: PRT
<213> ORGANISM: Oryctolagus cuniculus

<400> SEQUENCE: 58

```
Gly Val Pro Ser Arg Phe Lys Gly Ser Gly Ser Gly Thr Glu Phe Thr
1               5                   10                  15
```

```
Leu Thr Ile Ser Asp Leu Glu Cys Ala Asp Ala Ala Thr Tyr Tyr Cys
            20                  25                  30

<210> SEQ ID NO 59
<211> LENGTH: 44
<212> TYPE: PRT
<213> ORGANISM: Oryctolagus cuniculus

<400> SEQUENCE: 59

Phe Gly Gly Gly Thr Glu Val Val Val Lys Gly Asp Pro Val Ala Pro
1               5                   10                  15

Thr Val Leu Ile Phe Pro Pro Ala Ala Asp Gln Val Ala Thr Gly Thr
            20                  25                  30

Val Thr Ile Val Cys Val Ala Asn Lys Tyr Phe Pro
        35                  40

<210> SEQ ID NO 60
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asp Leu Asp Met Thr Gln Thr Pro Ala Ser Val Ser Glu Pro Val Gly
1               5                   10                  15

Gly Thr Val Thr Ile Lys Cys
            20

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Trp Tyr Gln Gln Lys Pro Gly Gln Pro Pro Lys Leu Leu Ile Tyr
1               5                   10                  15

<210> SEQ ID NO 62
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gly Val Pro Ser Arg Phe Lys Gly Ser Arg Ser Gly Thr Glu Tyr Thr
1               5                   10                  15

Leu Thr Ile Ser Asp Leu Glu Cys Ala Asp Ala Ala Thr Tyr Tyr Cys
            20                  25                  30

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63
```

```
Phe Gly Gly Gly Thr Glu Val Val Lys Gly Lys
1               5                   10
```

<210> SEQ ID NO 64
<211> LENGTH: 48
<212> TYPE: PRT
<213> ORGANISM: Oryctolagus cuniculus
<220> FEATURE:
<221> NAME/KEY: MOD_RES
<222> LOCATION: (15)..(16)
<223> OTHER INFORMATION: Any naturally occurring amino acid
<220> FEATURE:
<221> NAME/KEY: MOD_RES
<222> LOCATION: (22)..(22)
<223> OTHER INFORMATION: Any naturally occurring amino acid
<220> FEATURE:
<221> NAME/KEY: MOD_RES
<222> LOCATION: (42)..(42)
<223> OTHER INFORMATION: Any naturally occurring amino acid
<220> FEATURE:
<221> NAME/KEY: MOD_RES
<222> LOCATION: (45)..(46)
<223> OTHER INFORMATION: Any naturally occurring amino acid

<400> SEQUENCE: 64

```
Met Glu Thr Gly Leu Arg Trp Leu Leu Leu Val Ala Val Leu Xaa Xaa
1               5                   10                  15

Val Gln Cys Gln Ser Xaa Glu Glu Ser Gly Gly Arg Leu Val Thr Pro
            20                  25                  30

Gly Thr Pro Leu Thr Leu Thr Cys Thr Xaa Ser Gly Xaa Xaa Leu Ser
        35                  40                  45
```

<210> SEQ ID NO 65
<211> LENGTH: 48
<212> TYPE: PRT
<213> ORGANISM: Oryctolagus cuniculus
<220> FEATURE:
<221> NAME/KEY: MOD_RES
<222> LOCATION: (22)..(22)
<223> OTHER INFORMATION: Any naturally occurring amino acid

<400> SEQUENCE: 65

```
Met Glu Thr Gly Leu Arg Trp Leu Leu Leu Val Ala Val Leu Lys Gly
1               5                   10                  15

Val Gln Cys Gln Ser Xaa Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45
```

<210> SEQ ID NO 66
<211> LENGTH: 48
<212> TYPE: PRT
<213> ORGANISM: Oryctolagus cuniculus
<220> FEATURE:
<221> NAME/KEY: MOD_RES
<222> LOCATION: (15)..(16)
<223> OTHER INFORMATION: Any naturally occurring amino acid

<400> SEQUENCE: 66

```
Met Glu Thr Gly Leu Arg Trp Leu Leu Leu Val Ala Val Leu Xaa Xaa
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Ile Asp Leu Ser
        35                  40                  45
```

-continued

<210> SEQ ID NO 67
<211> LENGTH: 14
<212> TYPE: PRT
<213> ORGANISM: Oryctolagus cuniculus
<220> FEATURE:
<221> NAME/KEY: MOD_RES
<222> LOCATION: (5)..(5)
<223> OTHER INFORMATION: Any naturally occurring amino acid
<220> FEATURE:
<221> NAME/KEY: MOD_RES
<222> LOCATION: (11)..(12)
<223> OTHER INFORMATION: Any naturally occurring amino acid

<400> SEQUENCE: 67

Trp Val Arg Gln Xaa Pro Gly Lys Gly Leu Xaa Xaa Ile Gly
1               5                   10

<210> SEQ ID NO 68
<211> LENGTH: 14
<212> TYPE: PRT
<213> ORGANISM: Oryctolagus cuniculus
<220> FEATURE:
<221> NAME/KEY: MOD_RES
<222> LOCATION: (5)..(5)
<223> OTHER INFORMATION: Any naturally occurring amino acid

<400> SEQUENCE: 68

Trp Val Arg Gln Xaa Pro Gly Lys Gly Leu Glu Tyr Ile Gly
1               5                   10

<210> SEQ ID NO 69
<211> LENGTH: 14
<212> TYPE: PRT
<213> ORGANISM: Oryctolagus cuniculus

<400> SEQUENCE: 69

Trp Val Arg Gln Ala Pro Gly Lys Gly Leu Gln Trp Ile Gly
1               5                   10

<210> SEQ ID NO 70
<211> LENGTH: 31
<212> TYPE: PRT
<213> ORGANISM: Oryctolagus cuniculus
<220> FEATURE:
<221> NAME/KEY: MOD_RES
<222> LOCATION: (6)..(8)
<223> OTHER INFORMATION: Any naturally occurring amino acid
<220> FEATURE:
<221> NAME/KEY: MOD_RES
<222> LOCATION: (12)..(12)
<223> OTHER INFORMATION: Any naturally occurring amino acid
<220> FEATURE:
<221> NAME/KEY: MOD_RES
<222> LOCATION: (16)..(16)
<223> OTHER INFORMATION: Any naturally occurring amino acid
<220> FEATURE:
<221> NAME/KEY: MOD_RES
<222> LOCATION: (19)..(19)
<223> OTHER INFORMATION: Any naturally occurring amino acid
<220> FEATURE:
<221> NAME/KEY: MOD_RES
<222> LOCATION: (22)..(22)
<223> OTHER INFORMATION: Any naturally occurring amino acid
<220> FEATURE:
<221> NAME/KEY: MOD_RES
<222> LOCATION: (30)..(31)
<223> OTHER INFORMATION: Any naturally occurring amino acid

<400> SEQUENCE: 70

Arg Phe Thr Ile Ser Xaa Xaa Xaa Ser Thr Thr Xaa Asp Leu Lys Xaa
1               5                   10                  15

Thr Ser Xaa Thr Thr Xaa Asp Thr Ala Thr Tyr Phe Cys Xaa Xaa
            20                  25                  30

<210> SEQ ID NO 71
<211> LENGTH: 31
<212> TYPE: PRT
<213> ORGANISM: Oryctolagus cuniculus
<220> FEATURE:
<221> NAME/KEY: MOD_RES
<222> LOCATION: (9)..(9)
<223> OTHER INFORMATION: Any naturally occurring amino acid
<220> FEATURE:
<221> NAME/KEY: MOD_RES
<222> LOCATION: (16)..(16)
<223> OTHER INFORMATION: Any naturally occurring amino acid
<220> FEATURE:
<221> NAME/KEY: MOD_RES
<222> LOCATION: (19)..(19)
<223> OTHER INFORMATION: Any naturally occurring amino acid
<220> FEATURE:
<221> NAME/KEY: MOD_RES
<222> LOCATION: (22)..(22)
<223> OTHER INFORMATION: Any naturally occurring amino acid
<220> FEATURE:
<221> NAME/KEY: MOD_RES
<222> LOCATION: (31)..(31)
<223> OTHER INFORMATION: Any naturally occurring amino acid

<400> SEQUENCE: 71

Arg Phe Thr Ile Ser Arg Thr Ser Xaa Thr Thr Val Asp Leu Lys Xaa
1               5                   10                  15
Thr Ser Xaa Thr Thr Xaa Asp Thr Ala Thr Tyr Phe Cys Ala Xaa
            20                  25                  30

<210> SEQ ID NO 72
<211> LENGTH: 31
<212> TYPE: PRT
<213> ORGANISM: Oryctolagus cuniculus
<220> FEATURE:
<221> NAME/KEY: MOD_RES
<222> LOCATION: (7)..(8)
<223> OTHER INFORMATION: Any naturally occurring amino acid
<220> FEATURE:
<221> NAME/KEY: MOD_RES
<222> LOCATION: (12)..(12)
<223> OTHER INFORMATION: Any naturally occurring amino acid

<400> SEQUENCE: 72

Arg Phe Thr Ile Ser Lys Xaa Xaa Ser Thr Thr Xaa Asp Leu Lys Met
1               5                   10                  15
Thr Ser Pro Thr Thr Glu Asp Thr Ala Thr Tyr Phe Cys Gly Gly
            20                  25                  30

<210> SEQ ID NO 73
<211> LENGTH: 37
<212> TYPE: PRT
<213> ORGANISM: Oryctolagus cuniculus

<400> SEQUENCE: 73

Trp Gly Gln Gly Thr Leu Val Thr Val Ser Ser Gly Gln Pro Lys Ala
1               5                   10                  15
Pro Ser Val Phe Pro Leu Ala Pro Cys Cys Gly Asp Thr Pro Ser Ser
            20                  25                  30
Thr Val Thr Leu Gly
        35

<210> SEQ ID NO 74

```
<211> LENGTH: 46
<212> TYPE: PRT
<213> ORGANISM: Oryctolagus cuniculus
<220> FEATURE:
<221> NAME/KEY: MOD_RES
<222> LOCATION: (23)..(25)
<223> OTHER INFORMATION: Any naturally occurring amino acid
<220> FEATURE:
<221> NAME/KEY: MOD_RES
<222> LOCATION: (35)..(37)
<223> OTHER INFORMATION: Any naturally occurring amino acid

<400> SEQUENCE: 74

Met Asp Thr Arg Ala Pro Thr Gln Leu Leu Gly Leu Leu Leu Leu Trp
1               5                   10                  15

Leu Pro Gly Ala Arg Cys Xaa Xaa Xaa Val Met Thr Gln Thr Pro Ala
                20                  25                  30

Ser Val Xaa Xaa Xaa Val Gly Gly Thr Val Thr Ile Lys Cys
            35                  40                  45

<210> SEQ ID NO 75
<211> LENGTH: 46
<212> TYPE: PRT
<213> ORGANISM: Oryctolagus cuniculus
<220> FEATURE:
<221> NAME/KEY: MOD_RES
<222> LOCATION: (25)..(25)
<223> OTHER INFORMATION: Any naturally occurring amino acid
<220> FEATURE:
<221> NAME/KEY: MOD_RES
<222> LOCATION: (35)..(37)
<223> OTHER INFORMATION: Any naturally occurring amino acid

<400> SEQUENCE: 75

Met Asp Thr Arg Ala Pro Thr Gln Leu Leu Gly Leu Leu Leu Leu Trp
1               5                   10                  15

Leu Pro Gly Ala Arg Cys Ala Asp Xaa Val Met Thr Gln Thr Pro Ala
                20                  25                  30

Ser Val Xaa Xaa Xaa Val Gly Gly Thr Val Thr Ile Lys Cys
            35                  40                  45

<210> SEQ ID NO 76
<211> LENGTH: 45
<212> TYPE: PRT
<213> ORGANISM: Oryctolagus cuniculus

<400> SEQUENCE: 76

Met Asp Thr Arg Ala Pro Thr Gln Leu Leu Gly Leu Leu Leu Leu Trp
1               5                   10                  15

Leu Pro Gly Ala Arg Cys Asp Val Val Met Thr Gln Thr Pro Ala Ser
                20                  25                  30

Val Ser Ala Ala Val Gly Gly Thr Val Thr Ile Lys Cys
            35                  40                  45

<210> SEQ ID NO 77
<211> LENGTH: 15
<212> TYPE: PRT
<213> ORGANISM: Oryctolagus cuniculus
<220> FEATURE:
<221> NAME/KEY: MOD_RES
<222> LOCATION: (2)..(2)
<223> OTHER INFORMATION: Any naturally occurring amino acid
<220> FEATURE:
<221> NAME/KEY: MOD_RES
<222> LOCATION: (6)..(6)
<223> OTHER INFORMATION: Any naturally occurring amino acid
<220> FEATURE:
```

```
<221> NAME/KEY: MOD_RES
<222> LOCATION: (12)..(12)
<223> OTHER INFORMATION: Any naturally occurring amino acid
<220> FEATURE:
<221> NAME/KEY: MOD_RES
<222> LOCATION: (15)..(15)
<223> OTHER INFORMATION: Any naturally occurring amino acid

<400> SEQUENCE: 77

Trp Xaa Gln Gln Lys Xaa Gly Gln Pro Pro Lys Xaa Leu Ile Xaa
1               5                   10                  15

<210> SEQ ID NO 78
<211> LENGTH: 15
<212> TYPE: PRT
<213> ORGANISM: Oryctolagus cuniculus
<220> FEATURE:
<221> NAME/KEY: MOD_RES
<222> LOCATION: (6)..(6)
<223> OTHER INFORMATION: Any naturally occurring amino acid

<400> SEQUENCE: 78

Trp Tyr Gln Gln Lys Xaa Gly Gln Pro Pro Lys Leu Leu Ile Tyr
1               5                   10                  15

<210> SEQ ID NO 79
<211> LENGTH: 15
<212> TYPE: PRT
<213> ORGANISM: Oryctolagus cuniculus
<220> FEATURE:
<221> NAME/KEY: MOD_RES
<222> LOCATION: (12)..(12)
<223> OTHER INFORMATION: Any naturally occurring amino acid
<220> FEATURE:
<221> NAME/KEY: MOD_RES
<222> LOCATION: (15)..(15)
<223> OTHER INFORMATION: Any naturally occurring amino acid

<400> SEQUENCE: 79

Trp Phe Gln Gln Lys Pro Gly Gln Pro Pro Lys Xaa Leu Ile Xaa
1               5                   10                  15

<210> SEQ ID NO 80
<211> LENGTH: 32
<212> TYPE: PRT
<213> ORGANISM: Oryctolagus cuniculus
<220> FEATURE:
<221> NAME/KEY: MOD_RES
<222> LOCATION: (1)..(3)
<223> OTHER INFORMATION: Any naturally occurring amino acid
<220> FEATURE:
<221> NAME/KEY: MOD_RES
<222> LOCATION: (6)..(7)
<223> OTHER INFORMATION: Any naturally occurring amino acid
<220> FEATURE:
<221> NAME/KEY: MOD_RES
<222> LOCATION: (14)..(14)
<223> OTHER INFORMATION: Any naturally occurring amino acid
<220> FEATURE:
<221> NAME/KEY: MOD_RES
<222> LOCATION: (16)..(16)
<223> OTHER INFORMATION: Any naturally occurring amino acid
<220> FEATURE:
<221> NAME/KEY: MOD_RES
<222> LOCATION: (19)..(19)
<223> OTHER INFORMATION: Any naturally occurring amino acid
<220> FEATURE:
<221> NAME/KEY: MOD_RES
<222> LOCATION: (21)..(23)
<223> OTHER INFORMATION: Any naturally occurring amino acid
<220> FEATURE:
<221> NAME/KEY: MOD_RES
<222> LOCATION: (28)..(29)
```

-continued

```
<223> OTHER INFORMATION: Any naturally occurring amino acid
<220> FEATURE:
<221> NAME/KEY: MOD_RES
<222> LOCATION: (31)..(31)
<223> OTHER INFORMATION: Any naturally occurring amino acid

<400> SEQUENCE: 80

Xaa Xaa Xaa Ser Arg Xaa Xaa Gly Ser Gly Ser Gly Thr Xaa Phe Xaa
1               5                   10                  15

Leu Thr Xaa Ser Xaa Xaa Xaa Cys Ala Asp Ala Xaa Xaa Tyr Xaa Cys
            20                  25                  30

<210> SEQ ID NO 81
<211> LENGTH: 32
<212> TYPE: PRT
<213> ORGANISM: Oryctolagus cuniculus
<220> FEATURE:
<221> NAME/KEY: MOD_RES
<222> LOCATION: (3)..(3)
<223> OTHER INFORMATION: Any naturally occurring amino acid
<220> FEATURE:
<221> NAME/KEY: MOD_RES
<222> LOCATION: (6)..(6)
<223> OTHER INFORMATION: Any naturally occurring amino acid
<220> FEATURE:
<221> NAME/KEY: MOD_RES
<222> LOCATION: (16)..(16)
<223> OTHER INFORMATION: Any naturally occurring amino acid
<220> FEATURE:
<221> NAME/KEY: MOD_RES
<222> LOCATION: (19)..(19)
<223> OTHER INFORMATION: Any naturally occurring amino acid
<220> FEATURE:
<221> NAME/KEY: MOD_RES
<222> LOCATION: (28)..(28)
<223> OTHER INFORMATION: Any naturally occurring amino acid

<400> SEQUENCE: 81

Gly Val Xaa Ser Arg Xaa Lys Gly Ser Gly Ser Gly Thr Glu Phe Xaa
1               5                   10                  15

Leu Thr Xaa Ser Asp Leu Glu Cys Ala Asp Ala Xaa Thr Tyr Tyr Cys
            20                  25                  30

<210> SEQ ID NO 82
<211> LENGTH: 32
<212> TYPE: PRT
<213> ORGANISM: Oryctolagus cuniculus

<400> SEQUENCE: 82

Val Phe Pro Ser Arg Phe Lys Gly Ser Gly Ser Gly Thr Glu Phe Thr
1               5                   10                  15

Leu Thr Ile Ser Asp Leu Glu Cys Ala Asp Ala Ala Thr Tyr Ser Cys
            20                  25                  30

<210> SEQ ID NO 83
<211> LENGTH: 32
<212> TYPE: PRT
<213> ORGANISM: Oryctolagus cuniculus
<220> FEATURE:
<221> NAME/KEY: MOD_RES
<222> LOCATION: (29)..(29)
<223> OTHER INFORMATION: Any naturally occurring amino acid

<400> SEQUENCE: 83

Gly Val Pro Ser Arg Phe Ser Gly Ser Gly Ser Gly Thr Gln Phe Thr
1               5                   10                  15

Leu Thr Ile Ser Gly Val Gln Cys Ala Asp Ala Ala Xaa Tyr Tyr Cys
            20                  25                  30
```

<210> SEQ ID NO 84
<211> LENGTH: 36
<212> TYPE: PRT
<213> ORGANISM: Oryctolagus cuniculus

<400> SEQUENCE: 84

Phe Gly Gly Gly Thr Glu Val Val Lys Gly Asp Pro Val Ala Pro
1               5                   10                  15

Thr Val Leu Ile Phe Pro Pro Ala Ala Asp Gln Val Ala Thr Gly Thr
            20                  25                  30

Val Thr Ile Val
        35

<210> SEQ ID NO 85
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gggggtccgg aggtcgcctg gtcacgcctg g                                31

<210> SEQ ID NO 86
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gggtccggag gagacggtga ccagggtgcc                                  30

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
ttcattctca agcctcagac                                             20

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
ttttcactgc attctagttg tggt                                        24

<210> SEQ ID NO 89
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 89
gggaattcgc cgccaccatg gagcgcgcgt cctgc                    35

<210> SEQ ID NO 90
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gggatccacg cggaaccaga gcatactgcc gcggg                    35

<210> SEQ ID NO 91
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, c, g, or t
<220> FEATURE:
<221> NAME/KEY: modified_base
<222> LOCATION: (7)..(8)
<223> OTHER INFORMATION: a, c, g, or t
<220> FEATURE:
<221> NAME/KEY: modified_base
<222> LOCATION: (10)..(11)
<223> OTHER INFORMATION: a, c, g, or t

<400> SEQUENCE: 91
ggtnnknnkn nktggggcca aggcaccctg gtcaccgtct               40

<210> SEQ ID NO 92
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gccacaaaaa taagtggccg tgtcctcggt tgtcggactg               40

<210> SEQ ID NO 93
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ala Asp Phe
1

<210> SEQ ID NO 94
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94
```

Gly Asp Ala
1

<210> SEQ ID NO 95
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Tyr Ala Met Gly
1               5

<210> SEQ ID NO 96
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ser Tyr Thr Met Gly
1               5

<210> SEQ ID NO 97
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ile Ile Ala Asn Ser Gly Ala Thr Tyr Tyr Ala Ser Trp Ala Lys Gly
1               5                   10                  15

<210> SEQ ID NO 98
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ala Tyr Thr Met Gly
1               5

<210> SEQ ID NO 99
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gln Cys Ser Tyr Thr Ala Ile Gly Asn Ala Tyr Gly His Val
1               5                   10

<210> SEQ ID NO 100
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 100

Gln Ala Ser Gln Ser Ala Gly Ser Asn Leu Ala
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gln Ser Ser Tyr Thr Glu Ser Thr Thr Phe Gly His Val
1               5                   10

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Lys Thr Ser Thr Leu Glu Ser
1               5

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gln Ala Ser Gln Ser Ile Ser Asn Tyr Leu Ala
1               5                   10

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ile Ile Asn Ser Gly Ala Thr Tyr Tyr Ala Ser Ala Ala Lys Gly
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ile Ile Asn Ser Gly Ala Thr Tyr Tyr Ala Ser Trp Ala Ala Gly
1               5                   10                  15
```

<210> SEQ ID NO 106
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ile Ile Asn Ser Gly Ala Thr Tyr Tyr Ala Ser Trp Ala Lys Ala
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ile Ile Asn Ser Gly Ala Thr Tyr Tyr Ala Ser Trp Gly Lys Gly
1               5                   10                  15

<210> SEQ ID NO 108
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ile Val Ser Ser Asp Gly Gly Ile Tyr Tyr Ala Ser Trp Ala Lys Gly
1               5                   10                  15

<210> SEQ ID NO 109
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ile Ile Tyr Arg Asn Ile Lys Thr Tyr Tyr Ala Thr Trp Ala Lys Gly
1               5                   10                  15

<210> SEQ ID NO 110
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ile Ile Ser Asp Ile Asp Gln Ile Val Tyr Ala Thr Trp Ala Lys Gly
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 111

Ile Ile Ser Asp Ile Asp Asp Leu Phe Tyr Ala Ser Trp Ala Lys Gly
1               5                   10                  15

<210> SEQ ID NO 112
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gln Cys Ser Tyr Thr Ala Ile Gly Asn Tyr Gly His Ala
1               5                   10

<210> SEQ ID NO 113
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gln Cys Ser Tyr Thr Ala Ile Gly Asn Tyr Ala His Val
1               5                   10

<210> SEQ ID NO 114
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gln Ala Ala Gln Ser Ile Gly Ser Asn Leu Ala
1               5                   10

<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gln Gly Ser Gln Ser Ile Gly Ser Asn Leu Ala
1               5                   10

<210> SEQ ID NO 116
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ala Cys Ser Tyr Thr Ala Ile Gly Asn Tyr Gly His Val
1               5                   10

<210> SEQ ID NO 117
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 117

Lys Ala Ser Lys Ala Ala Ser
1               5

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Lys Ala Ala Lys Leu Ala Ser
1               5

<210> SEQ ID NO 119
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gln Ala Ser Gln Ser Ile Gly Ser Asn Ala Ala
1               5                   10

<210> SEQ ID NO 120
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ala Ala Ser Gln Ser Ile Gly Ser Asn Leu Ala
1               5                   10

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Lys Ala Ser Thr Leu Ala Ser
1               5

<210> SEQ ID NO 122
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gln Ala Ser Glu Asp Ile Ile Ser Asn Leu Ala
1               5                   10
```

<210> SEQ ID NO 123
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gln Ala Ser Gln Asn Ile Gly Ser Asp Leu Ser
1               5                   10

<210> SEQ ID NO 124
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Leu Asp Phe
1

<210> SEQ ID NO 125
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ser Asp Phe
1

<210> SEQ ID NO 126
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Met Tyr Thr Met Gly
1               5

<210> SEQ ID NO 127
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Pro Tyr Thr Met Gly
1               5

<210> SEQ ID NO 128
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 128

Val Tyr Thr Met Gly
1               5

<210> SEQ ID NO 129
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ile Tyr Thr Met Gly
1               5

<210> SEQ ID NO 130
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Asp Tyr Thr Met Gly
1               5

<210> SEQ ID NO 131
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Glu Tyr Thr Met Gly
1               5

<210> SEQ ID NO 132
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

His Tyr Thr Met Gly
1               5

<210> SEQ ID NO 133
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Thr Tyr Thr Met Gly
1               5

<210> SEQ ID NO 134
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gln Tyr Thr Met Gly
1               5

<210> SEQ ID NO 135
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Tyr Tyr Thr Met Gly
1               5

<210> SEQ ID NO 136
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gly Tyr Thr Met Gly
1               5

<210> SEQ ID NO 137
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Lys Tyr Thr Met Gly
1               5

<210> SEQ ID NO 138
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Asn Tyr Thr Met Gly
1               5

<210> SEQ ID NO 139
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Trp Tyr Thr Met Gly
```

```
<210> SEQ ID NO 140
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gly Phe Phe
1

<210> SEQ ID NO 141
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Ser Phe
1

<210> SEQ ID NO 142
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gly Pro Phe
1

<210> SEQ ID NO 143
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly His Phe
1

<210> SEQ ID NO 144
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Ile Phe
1

<210> SEQ ID NO 145
<211> LENGTH: 3
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 145

Gly Asn Phe
1

<210> SEQ ID NO 146
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gly Arg Phe
1

<210> SEQ ID NO 147
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gly Asp Ser
1

<210> SEQ ID NO 148
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Asp Pro
1

<210> SEQ ID NO 149
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Asp His
1

<210> SEQ ID NO 150
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gly Asp Asp
1

<210> SEQ ID NO 151
```

```
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gly Asp Ile
1

<210> SEQ ID NO 152
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Asp Asn
1

<210> SEQ ID NO 153
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gly Asp Arg
1

<210> SEQ ID NO 154
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Gly Val Leu
1

<210> SEQ ID NO 155
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gly Gly Glu
1

<210> SEQ ID NO 156
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156
```

Gly Leu His
1

<210> SEQ ID NO 157
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Asn Ser Gly Ala
1

<210> SEQ ID NO 158
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Tyr Arg Asn Ile Lys
1               5

<210> SEQ ID NO 159
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ala Asn Ser Gly Ala
1               5

<210> SEQ ID NO 160
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ser Ser Asp Gly Gly
1               5

<210> SEQ ID NO 161
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ser Asp Ile Asp Gln
1               5

<210> SEQ ID NO 162
<211> LENGTH: 5
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 162

Ser Asp Ile Asp Asp
1               5

<210> SEQ ID NO 163
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ala Ile Gly Asn Tyr
1               5

<210> SEQ ID NO 164
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Glu Ser Thr Thr Phe
1               5

<210> SEQ ID NO 165
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ala Ile Gly Asn Ala Tyr
1               5

<210> SEQ ID NO 166
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Arg Ser Thr Thr Thr Tyr
1               5

<210> SEQ ID NO 167
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Arg Tyr Thr Met Gly
1               5

```
<210> SEQ ID NO 168
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ser Phe Trp Met Ser
1               5

<210> SEQ ID NO 169
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Ile Ile Asn Ser Gly Ala Thr Tyr Tyr Ala Ser Trp Ala Lys Gly
1               5                   10                  15

<210> SEQ ID NO 170
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Gly Asp Phe
1

<210> SEQ ID NO 171
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gly Gly Leu
1

<210> SEQ ID NO 172
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gln Ala Ser Gln Ser Ile Gly Ser Asn Leu Ala
1               5                   10

<210> SEQ ID NO 173
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173
```

Lys Ala Ser Lys Leu Ala Ser
1               5

<210> SEQ ID NO 174
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gln Cys Ser Tyr Thr Ala Ile Gly Asn Tyr Gly His Val
1               5                   10

<210> SEQ ID NO 175
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gln Ser Thr Tyr Tyr Arg Ser Thr Thr Thr Tyr Gly Asn Thr
1               5                   10

<210> SEQ ID NO 176
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 176

His His His His His His
1               5

<210> SEQ ID NO 177
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ala Ala Ala
1

<210> SEQ ID NO 178
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Gln Ala Ser Gln Ser Ile Ser Ile Tyr Leu Ala
1               5                   10

<210> SEQ ID NO 179
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 179

Lys Thr Ser Thr Leu Asp Ser
1               5

<210> SEQ ID NO 180
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Asp Tyr Ala Leu Asn
1               5

<210> SEQ ID NO 181
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Tyr Ala Gly Gly Ser Gly Ser Thr Tyr Tyr Ala Ser Trp Ala Lys Gly
1               5                   10                  15

<210> SEQ ID NO 182
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gly Ser Asn
1

<210> SEQ ID NO 183
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ile Ser Asn
1

<210> SEQ ID NO 184
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Gly Ser Asp
1
```

```
<210> SEQ ID NO 185
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ser Asn Tyr
1

<210> SEQ ID NO 186
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Thr Asp Phe
1

<210> SEQ ID NO 187
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Gln Asp Phe
1

<210> SEQ ID NO 188
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Glu Asp Phe
1

<210> SEQ ID NO 189
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Met Asp Phe
1

<210> SEQ ID NO 190
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 190

Pro Asp Phe
1

<210> SEQ ID NO 191
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Trp Asp Phe
1

<210> SEQ ID NO 192
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Tyr Asp Phe
1

<210> SEQ ID NO 193
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Val Asp Phe
1

<210> SEQ ID NO 194
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Asp Asp Phe
1

<210> SEQ ID NO 195
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Arg Asp Phe
1

<210> SEQ ID NO 196
<211> LENGTH: 11
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 196

Gln Ala Ser Glu Arg Ile Arg Asn Trp Leu Ser
1               5                   10

<210> SEQ ID NO 197
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Gln Ser Tyr Tyr Gly Gly Ile Ser Ser Leu Tyr Asn Ile
1               5                   10

<210> SEQ ID NO 198
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Gln Cys Ser Ala Gly Gly Asn Ala Gly Asn Ala
1               5                   10

<210> SEQ ID NO 199
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gln Ser Thr Tyr Tyr Arg Ser Thr Thr Thr Tyr Gly Asn
1               5                   10

<210> SEQ ID NO 200
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Leu Gly Val Val Gly Ser Thr Ser Asp Asp Gly Phe Ala
1               5                   10

<210> SEQ ID NO 201
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ser Asn Cys
1

-continued

<210> SEQ ID NO 202
<211> LENGTH: 15
<212> TYPE: DNA
<213> ORGANISM: Oryctolagus cuniculus
<220> FEATURE:
<223> OTHER INFORMATION: This sequence encodes SEQ ID NO: 4

<400> SEQUENCE: 202
taggtatgca atggg                                                    15

<210> SEQ ID NO 203
<211> LENGTH: 48
<212> TYPE: DNA
<213> ORGANISM: Oryctolagus cuniculus
<220> FEATURE:
<223> OTHER INFORMATION: This sequence encodes SEQ ID NO: 5

<400> SEQUENCE: 203
atcatttata gaaatattaa gacatactac gcgacctggg ccaaaggc                 48

<210> SEQ ID NO 204
<211> LENGTH: 9
<212> TYPE: DNA
<213> ORGANISM: Oryctolagus cuniculus
<220> FEATURE:
<223> OTHER INFORMATION: This sequence encodes SEQ ID NO: 6

<400> SEQUENCE: 204 ggggacttt                                                            9

<210> SEQ ID NO 205
<211> LENGTH: 15
<212> TYPE: DNA
<213> ORGANISM: Oryctolagus cuniculus
<220> FEATURE:
<223> OTHER INFORMATION: This sequence encodes SEQ ID NO: 7

<400> SEQUENCE: 205
taggtataca atggg                                                    15

<210> SEQ ID NO 206
<211> LENGTH: 45
<212> TYPE: DNA
<213> ORGANISM: Oryctolagus cuniculus
<220> FEATURE:
<223> OTHER INFORMATION: This sequence encodes SEQ ID NO: 8

<400> SEQUENCE: 206
atcattaata gtggtgccac atactacgcg agctgggcga aaggc                   45

<210> SEQ ID NO 207
<211> LENGTH: 9
<212> TYPE: DNA
<213> ORGANISM: Oryctolagus cuniculus
<220> FEATURE:
<223> OTHER INFORMATION: This sequence encodes SEQ ID NO: 9

<400> SEQUENCE: 207 ggggacttt                                                            9

<210> SEQ ID NO 208
<211> LENGTH: 15
<212> TYPE: DNA
<213> ORGANISM: Oryctolagus cuniculus
<220> FEATURE:

```
<223> OTHER INFORMATION: This sequence encodes SEQ ID NO: 10

<400> SEQUENCE: 208
tagcttctgg atgag                                                        15

<210> SEQ ID NO 209
<211> LENGTH: 48
<212> TYPE: DNA
<213> ORGANISM: Oryctolagus cuniculus
<220> FEATURE:
<223> OTHER INFORMATION: This sequence encodes SEQ ID NO: 11

<400> SEQUENCE: 209
attattagtg atattgatga cctattctac gcgagctggg cgaaaggc                    48

<210> SEQ ID NO 210
<211> LENGTH: 9
<212> TYPE: DNA
<213> ORGANISM: Oryctolagus cuniculus
<220> FEATURE:
<223> OTHER INFORMATION: This sequence encodes SEQ ID NO: 12

<400> SEQUENCE: 210 ggtggtttg                                                                9

<210> SEQ ID NO 211
<211> LENGTH: 15
<212> TYPE: DNA
<213> ORGANISM: Oryctolagus cuniculus
<220> FEATURE:
<223> OTHER INFORMATION: This sequence encodes SEQ ID NO: 13

<400> SEQUENCE: 211
agctacgaca tgatc                                                        15

<210> SEQ ID NO 212
<211> LENGTH: 48
<212> TYPE: DNA
<213> ORGANISM: Oryctolagus cuniculus
<220> FEATURE:
<223> OTHER INFORMATION: This sequence encodes SEQ ID NO: 14

<400> SEQUENCE: 212
tacattggga gtcccgggac cacatactac gggagctggg cgaaaggc                    48

<210> SEQ ID NO 213
<211> LENGTH: 30
<212> TYPE: DNA
<213> ORGANISM: Oryctolagus cuniculus
<220> FEATURE:
<223> OTHER INFORMATION: This sequence encodes SEQ ID NO: 15

<400> SEQUENCE: 213
tctggtgata ttactaatag atttaacttg                                        30

<210> SEQ ID NO 214
<211> LENGTH: 15
<212> TYPE: DNA
<213> ORGANISM: Oryctolagus cuniculus
<220> FEATURE:
<223> OTHER INFORMATION: This sequence encodes SEQ ID NO: 16

<400> SEQUENCE: 214
aactacgaca tgatc                                                        15
```

```
<210> SEQ ID NO 215
<211> LENGTH: 48
<212> TYPE: DNA
<213> ORGANISM: Oryctolagus cuniculus
<220> FEATURE:
<223> OTHER INFORMATION: This sequence encodes SEQ ID NO: 17

<400> SEQUENCE: 215
tacattggga gtcccgggac cacttactac gcgagctggg cgaaaggc                 48

<210> SEQ ID NO 216
<211> LENGTH: 30
<212> TYPE: DNA
<213> ORGANISM: Oryctolagus cuniculus
<220> FEATURE:
<223> OTHER INFORMATION: This sequence encodes SEQ ID NO: 18

<400> SEQUENCE: 216
tctggtgata tcacaaatag atttaatttg                                     30

<210> SEQ ID NO 217
<211> LENGTH: 33
<212> TYPE: DNA
<213> ORGANISM: Oryctolagus cuniculus
<220> FEATURE:
<223> OTHER INFORMATION: This sequence encodes SEQ ID NO: 19

<400> SEQUENCE: 217
caggccagtg aggatattat tagtaattta gcc                                 33

<210> SEQ ID NO 218
<211> LENGTH: 21
<212> TYPE: DNA
<213> ORGANISM: Oryctolagus cuniculus
<220> FEATURE:
<223> OTHER INFORMATION: This sequence encodes SEQ ID NO: 20

<400> SEQUENCE: 218
aaggcatcca ctctggcatc t                                              21

<210> SEQ ID NO 219
<211> LENGTH: 39
<212> TYPE: DNA
<213> ORGANISM: Oryctolagus cuniculus
<220> FEATURE:
<223> OTHER INFORMATION: This sequence encodes SEQ ID NO: 21

<400> SEQUENCE: 219
cagagcagtt atactgagag tactactttt ggacatgtt                           39

<210> SEQ ID NO 220
<211> LENGTH: 33
<212> TYPE: DNA
<213> ORGANISM: Oryctolagus cuniculus
<220> FEATURE:
<223> OTHER INFORMATION: This sequence encodes SEQ ID NO: 22

<400> SEQUENCE: 220
caggccagtc agagtattgg tagtaattta gcc                                 33

<210> SEQ ID NO 221
<211> LENGTH: 21
<212> TYPE: DNA
<213> ORGANISM: Oryctolagus cuniculus
<220> FEATURE:
<223> OTHER INFORMATION: This sequence encodes SEQ ID NO: 23
```

<400> SEQUENCE: 221
aaggcatcta aactggcatc t                                              21

<210> SEQ ID NO 222
<211> LENGTH: 39
<212> TYPE: DNA
<213> ORGANISM: Oryctolagus cuniculus
<220> FEATURE:
<223> OTHER INFORMATION: This sequence encodes SEQ ID NO: 24

<400> SEQUENCE: 222
caatgcagtt atactgcaat tggtaattat ggacatgtt                           39

<210> SEQ ID NO 223
<211> LENGTH: 33
<212> TYPE: DNA
<213> ORGANISM: Oryctolagus cuniculus
<220> FEATURE:
<223> OTHER INFORMATION: This sequence encodes SEQ ID NO: 25

<400> SEQUENCE: 223
caggccagtc agagcattag taactactta gcc                                 33

<210> SEQ ID NO 224
<211> LENGTH: 21
<212> TYPE: DNA
<213> ORGANISM: Oryctolagus cuniculus
<220> FEATURE:
<223> OTHER INFORMATION: This sequence encodes SEQ ID NO: 26

<400> SEQUENCE: 224
aagacatcca ctctggaatc t                                              21

<210> SEQ ID NO 225
<211> LENGTH: 42
<212> TYPE: DNA
<213> ORGANISM: Oryctolagus cuniculus
<220> FEATURE:
<223> OTHER INFORMATION: This sequence encodes SEQ ID NO: 27

<400> SEQUENCE: 225
caaagtactt attataggag tactacaact tatggtaata ct                       42

<210> SEQ ID NO 226
<211> LENGTH: 33
<212> TYPE: DNA
<213> ORGANISM: Oryctolagus cuniculus
<220> FEATURE:
<223> OTHER INFORMATION: This sequence encodes SEQ ID NO: 28

<400> SEQUENCE: 226
caggccagtg agaggattag gaattggtta tcc                                 33

<210> SEQ ID NO 227
<211> LENGTH: 21
<212> TYPE: DNA
<213> ORGANISM: Oryctolagus cuniculus
<220> FEATURE:
<223> OTHER INFORMATION: This sequence encodes SEQ ID NO: 29

<400> SEQUENCE: 227
agggcctcca ctctagaatc t                                              21

<210> SEQ ID NO 228
<211> LENGTH: 33

```
<212> TYPE: DNA
<213> ORGANISM: Oryctolagus cuniculus
<220> FEATURE:
<223> OTHER INFORMATION: This sequence encodes SEQ ID NO: 30

<400> SEQUENCE: 228
caatgtagtg ctggtggcaa tgctggtaat gct                              33

<210> SEQ ID NO 229
<211> LENGTH: 33
<212> TYPE: DNA
<213> ORGANISM: Oryctolagus cuniculus
<220> FEATURE:
<223> OTHER INFORMATION: This sequence encodes SEQ ID NO: 31

<400> SEQUENCE: 229
caggccagtg agaggattag gaattggtta tcc                              33

<210> SEQ ID NO 230
<211> LENGTH: 21
<212> TYPE: DNA
<213> ORGANISM: Oryctolagus cuniculus
<220> FEATURE:
<223> OTHER INFORMATION: This sequence encodes SEQ ID NO: 32

<400> SEQUENCE: 230
agggcctcca ctctagaatc t                                           21

<210> SEQ ID NO 231
<211> LENGTH: 33
<212> TYPE: DNA
<213> ORGANISM: Oryctolagus cuniculus
<220> FEATURE:
<223> OTHER INFORMATION: This sequence encodes SEQ ID NO: 33

<400> SEQUENCE: 231
caatgtagtg ctggtggcaa tgctggtaat ggt                              33
```